US010246450B2

(12) United States Patent
Muthuppalaniappan et al.

(10) Patent No.: US 10,246,450 B2
(45) Date of Patent: *Apr. 2, 2019

(54) MODULATORS OF CALCIUM RELEASE-ACTIVATED CALCIUM CHANNEL

(71) Applicant: Rhizen Pharmaceuticals SA, La Chaux-de-Fonds (CH)

(72) Inventors: Meyyappan Muthuppalaniappan, Hyderabad (IN); Srikant Viswanadha, Hyderabad (IN); Gayatri S. Merikapudi, Hyderabad (IN); Swaroop K. Vakkalanka, La Chaux-de-Fonds (CH)

(73) Assignee: RHIZEN PHARMACEUTICALS SA, La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,229

(22) Filed: Feb. 8, 2018

(65) Prior Publication Data

US 2018/0222898 A1    Aug. 9, 2018

Related U.S. Application Data

(63) Continuation of application No. 15/635,268, filed on Jun. 28, 2017, now Pat. No. 9,944,631, which is a continuation of application No. 14/539,470, filed on Nov. 12, 2014, now Pat. No. 9,758,514, which is a continuation of application No. 13/722,523, filed on Dec. 20, 2012, now Pat. No. 8,921,364, which is a continuation of application No. 12/899,416, filed on Oct. 6, 2010, now Pat. No. 8,377,970.

(Continued)

(30) Foreign Application Priority Data

Oct. 8, 2009   (IN) .......................... 2439/CHE/2009
Oct. 30, 2009  (IN) .......................... 2636/CHE/2009
Jan. 25, 2010  (IN) ............................ 158/CHE/2010
Jun. 2, 2010   (IN) .......................... 1513/CHE/2010
Jun. 2, 2010   (IN) .......................... 1514/CHE/2010

(51) Int. Cl.
| | | |
|---|---|---|
| C07D 417/10 | (2006.01) |
| A61K 31/415 | (2006.01) |
| A61K 31/422 | (2006.01) |
| A61K 31/433 | (2006.01) |
| A61K 31/4439 | (2006.01) |
| A61K 31/455 | (2006.01) |
| A61K 31/496 | (2006.01) |
| A61K 31/506 | (2006.01) |
| A61K 31/5377 | (2006.01) |
| A61K 45/06 | (2006.01) |
| C07D 207/327 | (2006.01) |
| C07D 207/337 | (2006.01) |
| C07D 231/12 | (2006.01) |
| C07D 295/195 | (2006.01) |
| C07D 401/04 | (2006.01) |
| C07D 401/10 | (2006.01) |

(Continued)

(52) U.S. Cl.
CPC .......... *C07D 417/10* (2013.01); *A61K 31/415* (2013.01); *A61K 31/422* (2013.01); *A61K 31/427* (2013.01); *A61K 31/433* (2013.01); *A61K 31/4439* (2013.01); *A61K 31/455* (2013.01); *A61K 31/496* (2013.01); *A61K 31/506* (2013.01); *A61K 31/5377* (2013.01); *A61K 45/06* (2013.01); *C07D 207/327* (2013.01); *C07D 207/337* (2013.01); *C07D 231/12* (2013.01); *C07D 295/195* (2013.01); *C07D 401/04* (2013.01); *C07D 401/10* (2013.01); *C07D 401/12* (2013.01); *C07D 401/14* (2013.01); *C07D 403/04* (2013.01); *C07D 403/10* (2013.01); *C07D 403/12* (2013.01); *C07D 403/14* (2013.01); *C07D 413/10* (2013.01); *C07D 413/12* (2013.01); *C07D 413/14* (2013.01); *C07D 417/12* (2013.01); *C07D 417/14* (2013.01); *C12N 5/0634* (2013.01); *C12N 2500/46* (2013.01); *Y02A 50/422* (2018.01)

(58) Field of Classification Search
None
See application file for complete search history.

(56) References Cited

U.S. PATENT DOCUMENTS

| | | |
|---|---|---|
| 6,348,480 B1 | 2/2002 | Kubota et al. |
| 6,506,747 B1 | 1/2003 | Betageri et al. |

(Continued)

FOREIGN PATENT DOCUMENTS

| | | |
|---|---|---|
| EP | 1875925 A1 | 1/2008 |
| WO | WO-9962885 A1 | 12/1999 |

(Continued)

OTHER PUBLICATIONS

Yonetoku, et al., Novel potent and selective calcium-release-activated calcium (CRAC) channel inhibitors. Part 1: Synthesis and inhibitory activity of 5-(1-methyl-3-trifluoromethyl-1H-pyrazol-5-yl)-2-thiophenecarboxamides, Bioorganic & Medicinal Chemistry 14 (2006) 4750-4760.

(Continued)

*Primary Examiner* — Kamal A Saeed
(74) *Attorney, Agent, or Firm* — Blank Rome LLP

(57) ABSTRACT

Disclosed are novel calcium release-activated calcium (CRAC) channel inhibitors, methods for preparing them, pharmaceutical compositions containing them, and methods of treatment using them. The present disclosure also relates to methods for treating non-small cell lung cancer (NSCLC) with CRAC inhibitors, and to methods for identifying therapeutics for treating and of diagnosing cancer.

19 Claims, No Drawings

Related U.S. Application Data

(60) Provisional application No. 61/265,540, filed on Dec. 1, 2009.

(51) Int. Cl.

| | | |
|---|---|---|
| *C07D 401/12* | (2006.01) | |
| *C07D 401/14* | (2006.01) | |
| *C07D 403/04* | (2006.01) | |
| *C07D 403/10* | (2006.01) | |
| *C07D 403/12* | (2006.01) | |
| *C07D 403/14* | (2006.01) | |
| *C07D 413/10* | (2006.01) | |
| *C07D 413/12* | (2006.01) | |
| *C07D 413/14* | (2006.01) | |
| *C07D 417/12* | (2006.01) | |
| *C07D 417/14* | (2006.01) | |
| *C12N 5/078* | (2010.01) | |
| *A61K 31/427* | (2006.01) | |

(56) References Cited

U.S. PATENT DOCUMENTS

| | | |
|---|---|---|
| 6,696,267 B2 | 2/2004 | Normant et al. |
| 7,452,675 B2 | 11/2008 | Penner et al. |
| 2001/0044445 A1 | 11/2001 | Bamaung et al. |
| 2006/0173006 A1 | 8/2006 | Sun et al. |
| 2007/0249051 A1 | 10/2007 | Bohnert et al. |
| 2008/0293092 A1 | 11/2008 | Stauderman et al. |
| 2009/0023177 A1 | 1/2009 | Penner et al. |
| 2009/0131484 A1 | 5/2009 | Ishikawa |
| 2009/0311720 A1 | 12/2009 | Roos et al. |
| 2010/0087415 A1 | 4/2010 | Whitten et al. |
| 2010/0152241 A1 | 6/2010 | Whitten |

FOREIGN PATENT DOCUMENTS

| | | |
|---|---|---|
| WO | WO-02089793 A1 | 11/2002 |
| WO | WO-03022852 A2 | 3/2003 |
| WO | WO-03045912 A1 | 6/2003 |
| WO | WO-2004078995 A2 | 9/2004 |
| WO | WO-2005009539 A2 | 2/2005 |
| WO | WO-2005009954 A2 | 2/2005 |
| WO | WO-2005095351 A1 | 10/2005 |
| WO | WO-2005113511 A1 | 12/2005 |
| WO | WO-2006034402 A2 | 3/2006 |
| WO | WO-2006050214 A2 | 5/2006 |
| WO | WO-2006081389 A1 | 8/2006 |
| WO | WO-2006081391 A2 | 8/2006 |
| WO | WO-2006115140 A1 | 11/2006 |
| WO | WO-2007004038 A1 | 1/2007 |
| WO | WO-2007087427 A2 | 8/2007 |
| WO | WO-2007087429 A2 | 8/2007 |
| WO | WO-2007087441 A2 | 8/2007 |
| WO | WO-2007087442 A2 | 8/2007 |
| WO | WO-2007087443 A2 | 8/2007 |
| WO | WO-2007089904 A2 | 8/2007 |
| WO | WO-2007109362 A2 | 9/2007 |
| WO | WO-2007112093 A2 | 10/2007 |
| WO | WO-2007121186 A2 | 10/2007 |
| WO | WO-2007139926 A2 | 12/2007 |
| WO | WO-2008016643 A2 | 2/2008 |
| WO | WO-2008039520 A2 | 4/2008 |
| WO | WO-2008063504 A2 | 5/2008 |
| WO | WO-2008103310 A1 | 8/2008 |
| WO | WO-2008106731 A1 | 9/2008 |
| WO | WO-2008148108 A1 | 12/2008 |
| WO | WO-2009017818 A1 | 2/2009 |
| WO | WO-2009017819 A1 | 2/2009 |
| WO | WO-2009017831 A1 | 2/2009 |
| WO | WO-2009035818 A1 | 3/2009 |
| WO | WO-2009038775 A1 | 3/2009 |
| WO | WO-2009076454 A2 | 6/2009 |
| WO | WO-2009089305 A1 | 7/2009 |
| WO | WO-2010025295 A2 | 3/2010 |
| WO | WO-2010027875 A2 | 3/2010 |
| WO | WO-2010034003 A2 | 3/2010 |
| WO | WO-2010034011 A2 | 3/2010 |
| WO | WO-2010039236 A1 | 4/2010 |
| WO | WO-2010039237 A1 | 4/2010 |
| WO | WO-2010039238 A1 | 4/2010 |
| WO | WO-2010048559 A2 | 4/2010 |

OTHER PUBLICATIONS

Yonetoku, et al., Novel potent and selective calcium-release-activated calcium (CRAC) channel inhibitors. Part 2: Synthesis and inhibitory activity of aryl-3-trifluoromethylpyrazoles, Bioorganic & Medicinal Chemistry 14 (2006) 5370-5383.

Yonetoku, et al., Novel Potent and Selective Ca2+ release-activated Ca2+ (CRAC) channel inhibitors. Part 3: Synthesis and CRAC channel inhibitory activity of 4'-[trifluoromethyl)pyrazol-1-yl]carboxanilides, Bioorganic & Medicinal Chemistry 16 (2008) 9457-9466.

Isabella Derler et al., *Expert Opinion in Drug Discovery*, 3(7), 787-800, 2008.

Taiji et al. (*European Journal of Pharmacology* 560, 225-233, 2007).

Yasuhiro Yonetoku et al. (*Bio. & Med. Chem.*, 16, 9457-9466, 2008).

Yasurio Yonetoky et.al., *Bio. & Med. Chem.*, 14, 4750-4760, 2006.

Yasurio Yonetoky et.al., *Bio. & Med. Chem.*, 14, 5370-5383, 2006. asthma.

Yousang G et al., Cell Calcium, 42, 145-156, 2007.

International Search Report for PCT/IB2010/002535.

U.S. Appl. No. 12/899,410, filed Oct. 6, 2010.

International Search Report for PCT/IB2010/002539.

International Preliminary Report on Patentability issued in PCT/IB2010/002535 dated Apr. 11, 2012.

Gudermann, et al., Calcium-dependent Growth Regulation of Small Cell Lung Cancer Cells by Neuropeptides, Endocrine-related Cancer, 2006, 13:1069-1084.

Soliman, et al., The Scope of the Reactions of Hydrazines and Hydrazones, Pharmazie, 1978, 33:4:184-185.

Database Registry [online] Chemical Abstracts Service, Columbus, Ohio, USA, Retrieved from STN, Registry 1174838-72-2 (Entered STN: Aug. 21, 2009).

MODULATORS OF CALCIUM RELEASE-ACTIVATED CALCIUM CHANNEL

This application is a continuation of U.S. patent application Ser. No. 15/635,268, filed Jun. 28, 2017, which is a continuation U.S. patent application Ser. No. 14/539,470, filed Nov. 12, 2014, now U.S. Pat. No. 9,758,514, which is a continuation of U.S. patent application Ser. No. 13/722,523, filed Dec. 20, 2012, now U.S. Pat. No. 8,921,364, which is a continuation of U.S. patent application Ser. No. 12/899,416, filed Oct. 6, 2010, now U.S. Pat. No. 8,377,970, which claims the benefit of Indian Provisional Patent Application Nos. 2439/CHE/2009 dated 8 Oct. 2009; 2636/CHE/2009 dated 30 Oct. 2009; 158/CHE/2010 dated 25 Jan. 2010; 1513/CHE/2010 dated 2 Jun. 2010; and 1514/CHE/2010 dated 2 Jun. 2010; and U.S. Provisional Patent Application No. 61/265,540 dated 1 Dec. 2009, each of which is hereby incorporated by reference.

FIELD OF THE INVENTION

The present invention relates to calcium release-activated calcium (CRAC) channel inhibitors of formula I and pharmaceutically acceptable salts thereof, methods for preparing them, pharmaceutical compositions containing them, and methods of treatment with them.

BACKGROUND OF THE INVENTION

The regulation of intracellular calcium is a key element in the transduction of signals into and within cells. Cellular responses to growth factors, neurotransmitters, hormones and a variety of other signal molecules are initiated through calcium-dependent processes. The importance of calcium ion as a second messenger is emphasised by many different mechanisms which work together to maintain calcium homeostasis. Changes in intracellular free calcium ion concentration represent the most wide-spread and important signalling event for regulating a plethora of cellular responses. A widespread route for calcium ion entry into the cell is through store-operated channels (SOCs), i.e. many cell types employ store-operated calcium ion entry as their principal pathway for calcium ion influx. This mechanism is engaged following calcium ion release from stores, where the depleted stores lead to activation of calcium release-activated calcium (CRAC) channels.

CRAC channels, a subfamily of store-operated channels, are activated by the release of calcium from intracellular stores, particularly from the endoplasmic reticulum (ER). These channels are key factors in the regulation of a wide range of cellular function, including muscle contraction, protein and fluid secretion and control over cell growth and proliferation and hence play an essential role in various diseases such as immune disorders and allergic responses. Among several biophysically distinct store-operated currents the best characterized and most calcium ion selective one is the CRAC current. Thus, CRAC channels mediate essential functions from secretion to gene expression and cell growth and form a network essential for the activation of immune cells that establish the adaptive immune response. Recently two proteins, stromal interaction molecule (STIM1) and CRAC Modulator 1 (CRACM1 or Orai1), have been identified as the essential components that fully reconstitute and amplify CRAC currents in heterologous expression systems with a similar biophysical fingerprint. In mammals, there exist several homologs of these proteins: STIM1 and STIM2 in the endoplasmic reticulum and CRACM1, CRACM2, and CRACM3 in the plasma membrane.

CRAC currents were initially discovered in lymphocytes and mast cells, and at the same time have been characterized in various cell lines such as S2 drosophila, DT40 B cells, hepatocytes, dendritic, megakaryotic, and Madin-Darby canine kidney cells. In lymphocytes and in mast cells, activation through antigen or Fc receptors initiates the release of calcium ion from intracellular stores caused by the second messenger inositol (1,4,5)-triphosphate (Ins(1,4,5)$P_3$), which in turn leads to calcium ion influx through CRAC channels in the plasma membrane. Store-operated $Ca^{2+}$ currents characterized in smooth muscle, A431 epidermal cells, endothelial cells from various tissues, and prostate cancer cell lines show altered biophysical characteristics suggesting a distinct molecular origin.

For example, calcium ion influx across the cell membrane is important in lymphocyte activation and adaptive immune responses. $[Ca^{2+}]$-oscillations triggered through stimulation of the TCR (T-cell antigen receptor) have been demonstrated to be prominent, and appear to involve only a single calcium ion influx pathway, the store-operated CRAC channel. See, e.g., Lewis "Calcium signalling mechanisms in T lymphocytes," Annu. Rev. Immunol. 19, (2001), 497-521; Feske et al. "$Ca^{++}$ calcineurin signalling in cells of the immune system," Biochem. Biophys. Res. Commun. 311, (2003), 1117-1132; Hogan et al. "Transcriptional regulation by calcium, calcineurin, and NFAT," Genes Dev. 17, (2003) 2205-2232.

It is well established now that intracellular calcium plays an important role in various cellular functions, and that its concentration is regulated by calcium ion influx through calcium channels on the cell membrane. Calcium ion channels, which are located in the nervous, endocrine, cardiovascular, and skeletal systems and are modulated by membrane potential, are called voltage-operated $Ca^{2+}$ (VOC) channels. These channels are classified into L, N, P, Q, R, and T subtypes. Excessive $Ca^{2+}$ influx through the VOC channels causes hypertension and brain dysfunction. In contrast, calcium ion channels on inflammatory cells, including lymphocytes, mast cells, and neutrophils, can be activated regardless of their membrane potential. This type of calcium ion channel has been reported to act in the crisis and exacerbation of inflammation and autoimmune diseases. In the T cells, it has been reported that the early stages of activation consist of pre- and post-$Ca^{2+}$ events. The stimulation of T cell receptors induces pre-$Ca^{2+}$ events, including the generation of IP3, followed by the release of $Ca^{2+}$ from the endoplasmic reticulum (ER). In post-$Ca^{2+}$ events, depletion of $Ca^{2+}$ in the ER induces the activation of CRAC channels, and capacitative $Ca^{2+}$ influx through the CRAC channel sustains high intracellular $Ca^{2+}$ concentration ($[Ca^{2+}]i$). This prolonged high $[Ca^{2+}]i$ activates cytosolic signal transduction to produce lipid mediators (e.g., $LTD_4$), cytokines [e.g., interleukin-2 (IL-2)], and matrix metalloproteinases, which participate in the pathogenesis of inflammation and autoimmune diseases.

These facts suggest that CRAC channel modulators can be useful for the treatment of diseases caused by the activation of inflammatory cells without side effects observed in steroids. Since VOC channel modulators would cause adverse events in the nervous and cardiovascular systems, it may be necessary for CRAC channel modulators to exhibit sufficient selectivity over VOC channels if they are to be used as anti-inflammatory drugs.

Accordingly, CRAC channel modulators have been said to be useful in treatment, prevention and/or amelioration of diseases or disorders associated with calcium release-activated calcium channel including, but not limited to, inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma, Sjogren's syndrome, cancer and other proliferative diseases, and autoimmune diseases or disorders, See, e.g., International Publication Nos. WO 2005/009954, WO 2005/009539, WO 2005/009954, WO 2006/034402, WO 2006/081389, WO 2006/081391, WO 2007/087429, WO 2007/087427, WO 2007087441, WO 200/7087442, WO 2007/087443, WO 2007/089904, WO 2007109362, WO 2007/112093, WO 2008/039520, WO 2008/063504, WO 2008/103310, WO 2009/017818, WO 2009/017819, WO 2009/017831, WO 2010/039238, WO 2010/039237, WO 2010/039236, WO 2009/089305 and WO 2009/038775, and US Publication Nos.: US 2006/0173006 and US 2007/0249051.

CRAC channel inhibitors which have been identified include SK&F 96365 (1), Econazole (2) and L-651582 (3).

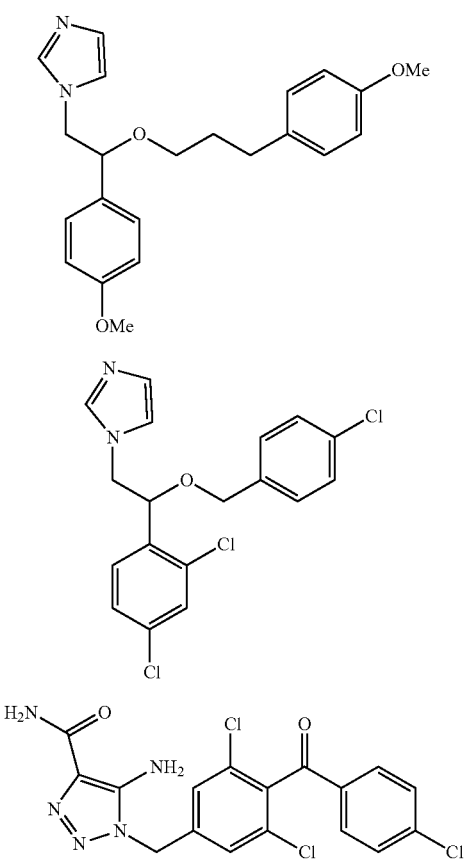

However, these molecules lack sufficient potency and selectivity over VOC channels and hence are not suitable for therapeutic use.

Recent publications by Taiji et al. (*European Journal of Pharmacology*, 560, 225-233, 2007) and Yasurio Yonetoky et al. (*Bio. & Med. Chem.*, 16, 9457-9466, 2008) describe a selective CRAC channel inhibitor coded YM-58483 that is capable of inhibiting T cell function and proposed to be of some benefit in the treatment of inflammatory diseases including bronchial asthma.

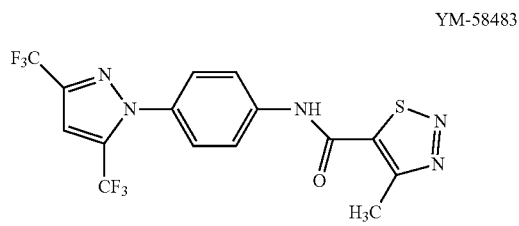 [SMILES: Cc1nnsc1C(=O)Nc1ccc(-n2nc(C(F)(F)F)cc2C(F)(F)F)cc1]

Yasurio Yonetoky et al. disclose YM-58483 to be selective for CRAC channels over the voltage operated channels (VOC) with a selective index of 31.

Other CRAC channel modulators disclosed include various biaryl and/or heterocyclic carboxanilide compounds including for example PCT or US patent applications assigned to Synta Pharmaceuticals viz. WO 2005/009954, WO 2005/009539, WO 2005/009954, WO 2006/034402, WO 2006/081389, WO 2006/081391, WO 2007/087429, WO 2007/087427, WO 2007087441, WO 200/7087442, WO 2007/087443, WO 2007/089904, WO 2007109362, WO 2007/112093, WO 2008/039520, WO 2008/063504, WO 2008/103310, WO 2009/017818, WO 2009/017819, WO 2009/017831, WO 2010/039238, WO 2010/039237, WO 2010/039236, WO 2009/089305 and WO 2009/038775, US 2006/0173006 and US 2007/0249051.

Other patent publications relating to CRAC channel modulators include applications by Astellas, Queens Medical Centre, Calcimedica and others viz., WO 2007/121186, WO 2006/050214, WO 2007/139926, WO 2008/148108, U.S. Pat. No. 7,452,675, US 2009/023177, WO 2007/139926, U.S. Pat. No. 6,696,267, U.S. Pat. No. 6,348,480, WO 2008/106731, US 2008/0293092, WO 2010/048559, WO 2010/027875, WO2010/025295, WO 2010/034011, WO2010/034003, WO 2009/076454, WO 2009/035818, US 2010/0152241, US 2010/0087415, US 2009/0311720 and WO 2004/078995.

Further review and literature disclosure in the area of CRAC channels includes Isabella Derler et al., *Expert Opinion in Drug Discovery*, 3(7), 787-800, 2008; Yousang G et al., Cell Calcium, 42, 145-156, 2007; Yasurio Yonetoky et. al., *Bio. & Med. Chem.*, 14, 4750-4760, 2006; and Yasurio Yonetoky et. al., *Bio. & Med. Chem.*, 14, 5370-5383, 2006. All of these patents and/or patent applications and literature disclosures are incorporated herein by reference in their entirety for all purposes.

Cancer is a major public health problem in India, the U.S. and many other parts of the world. Currently, 1 in 4 deaths in India is due to cancer. Lung cancer is the leading cause of cancer deaths worldwide because of its high incidence and mortality, with 5-year survival estimates of ~10% for non-small cell lung cancer (NSCLC). It has been reported that further investigations on the mechanisms of tumorigenesis and chemoresistance of lung cancer are needed to improve the survival rate (Jemal A, et al., *Cancer Statistics, CA*

Cancer. J. Clin., 56, 106-130, 2006). There are four major types of NSCLC, namely, adenocarcinoma, squamous cell carcinoma, bronchoalveolar carcinoma, and large cell carcinoma. Adenocarcinoma and squamous cell carcinoma are the most common types of NSCLC based on cellular morphology (Travis et al., Lung Cancer Principles and Practice, Lippincott-Raven, N.Y., 361-395, 1996). Adenocarcinomas are characterized by a more peripheral location in the lung and often have a mutation in the K-ras oncogene (Gazdar et al., Anticancer Res., 14, 261-267, 1994). Squamous cell carcinomas are typically more centrally located and frequently carry p53 gene mutations (Niklinska et al., Folia Histochem. Cytobiol., 39, 147-148, 2001).

The majority of NSCLCs are characterized by the presence of the ras mutation thereby rendering the patient relatively insensitive to treatment by known kinase inhibitors. As a result, current treatments of lung cancer are generally limited to cytotoxic drugs, surgery, and radiation therapy. There is a need for treatments which have fewer side effects and more specifically target the cancer cells, are less invasive, and improve the prognosis of patients.

The identification of lung tumor-initiating cells and associated markers may be useful for optimization of therapeutic approaches and for predictive and prognostic information in lung cancer patients. Accordingly, a need remains for new methods of predicting, evaluating and treating patients afflicted with lung cancer.

There still remains an unmet and dire need for small molecule modulators having specificity towards Stim1 and/or Orai1 in order to regulate and/or modulate activity of CRAC channels, particularly for the treatment of diseases and disorders associated with the CRAC.

SUMMARY OF THE INVENTION

The present invention relates to compounds of formula (I), methods for their preparation, pharmaceutical compositions containing them, and methods of treatment with them.

In particular, compounds of formula (I) and their pharmaceutically acceptable salts thereof are calcium release-activated calcium channel modulators useful in the treatment, prevention, inhibition and/or amelioration of diseases or disorders associated with calcium release-activated calcium channel.

In one aspect, the present invention relates to a compound of formula (I):

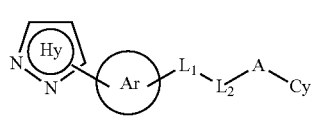

(I)

or a tautomer thereof, prodrug thereof, N-oxide thereof, pharmaceutically acceptable ester thereof or pharmaceutically acceptable salt thereof,
wherein
Ring Hy represents

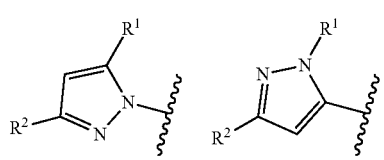

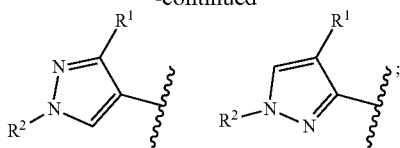

Ring Hy is optionally substituted with R'";
$R^1$ and $R^2$ are the same or different and are independently selected from $CH_3$, $CH_2F$, $CHF_2$, $CF_3$, substituted or unsubstituted $C_{(3-5)}$ cycloalkyl, $CH_2$—$OR^a$, $CH_2$—$NR^aR^b$, CN and COOH with the proviso that:
  a) both $R^1$ and $R^2$ at the same time do not represent $CF_3$,
  b) both $R^1$ and $R^2$ at the same time do not represent $CH_3$,
  c) when $R^1$ is $CF_3$ then $R^2$ is not $CH_3$ and
  d) when $R^1$ is $CH_3$ then $R^2$ is not $CF_3$;
Ring Ar represents:

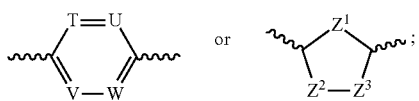

T, U, V and W are the same or different and are independently selected from $CR^a$ and N;
$Z^1$, $Z^2$ and $Z^3$ are the same or different and are independently selected from $CR^a$, $CR^aR^b$, O, S and —$NR^a$, with the proviso that at least one of $Z^1$, $Z^2$ and $Z^3$ represents O, S or —$NR^a$;
$L_1$ and $L_2$ together represent —NH—C(=X)—, —NH—S(=O)$_q$—, —C(=X)NH—, —NH—CR'R" or —S(=O)$_q$NH—;
A is absent or selected from —(CR'R")—, O, S(=O)$_q$, C(=X) and —$NR^a$;
each occurrence of R' and R" are the same or different and are independently selected from hydrogen, hydroxy, cyano, halogen, —$OR^a$, —$COOR^a$, —$S(=O)_q$—$R^a$, —$NR^aR^b$, —C(=X)—$R^a$, substituted or unsubstituted $C_{(1-6)}$ alkyl group, substituted or unsubstituted $C_{(1-6)}$ alkenyl, substituted or unsubstituted $C_{(1-6)}$ alkynyl, and substituted or unsubstituted $C_{(3-5)}$cycloalkyl, or R' and R", when directly bound to a common atom, may be joined to form a substituted or unsubstituted saturated or unsaturated 3-6 member ring, which may optionally include one or more heteroatoms which may be same or different and are selected from O, $NR^a$ and S;
R'" is selected from hydrogen, hydroxy, cyano, halogen, —$OR^a$, —$COOR^a$, —$S(=O)_q$—$R^a$, —$NR^aR^b$, —C(=X)—$R^a$, substituted or unsubstituted $C_{(1-6)}$ alkyl group, substituted or unsubstituted $C_{(1-6)}$ alkenyl, substituted or unsubstituted $C_{(1-6)}$ alkynyl, and substituted or unsubstituted $C_{(3-5)}$cycloalkyl;
each occurrence of X is independently selected from O, S and —$NR^a$;
Cy is selected from monocyclic substituted or unsubstituted cycloalkyl group, monocyclic substituted or unsubstituted heterocyclyl, monocyclic substituted or unsubstituted aryl, and monocyclic substituted or unsubstituted heteroaryl;
each occurrence of $R^a$ and $R^b$ are the same or different and are independently selected from hydrogen, nitro, hydroxy, cyano, halogen, —$OR^c$, —$S(=O)_q$—$R^c$, —$NR^cR^d$, —C(=Y)—R, —$CR^cR^d$—C(=Y)—R, —$CR^cR^d$—Y—$CR^cR^d$—, —C(=Y)—$NR^cR^d$, —$NR^cR^d$—C(=Y)—$NR^cR^d$—, —$S(=O)_q$—$NR^cR^d$, —$NR^cR^d$—$S(=O)_q$—$NR^cR^d$—, —$NR^cR^d$—$NR^cR^d$—, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocylyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when $R^a$ and $R^b$ are directly bound to the same atom, they may be joined to form a substituted or unsubstituted saturated or unsaturated 3-10 membered ring, which may optionally include one or more heteroatoms which may be same or different and are selected from O, $NR^c$ and S;

each occurrence of $R^c$ and $R^d$ may be same or different and are independently selected from hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic group, substituted or unsubstituted heterocyclylalkyl, or when two $R^c$ and/or $R^d$ substitutents are directly bound to the same atom, they may be joined to form a substituted or unsubstituted saturated or unsaturated 3-10 membered ring, which may optionally include one or more heteroatoms which are the same or different and are selected from O, NH and S;

each occurrence of Y is selected from O, S and $-NR^a$; and each occurrence of q independently represents an integer 0, 1 or 2;
with Proviso (e) that the compound of formula (I) is not:
N-[4-[5-cyclopropyl-3-(trifluoromethyl)-1H-pyrazol-1-yl]phenyl]-1-(difluoromethyl)-5-methyl-1H-pyrazole-3-carboxamide;
N-[4-[5-cyclopropyl-3-(trifluoromethyl)-1H-pyrazol-1-yl]phenyl]-1-methyl-4-nitro-1H-pyrazole-5-carboxamide;
N-[4-[5-cyclopropyl-3-(trifluoromethyl)-1H-pyrazol-1-yl]phenyl]-3-(1-ethyl-5-methyl-1H-pyrazol-4-yl)-5-isoxazolecarboxamide;
N-[4-[5-cyclopropyl-3-(trifluoromethyl)-1H-pyrazol-1-yl]phenyl]-4,5-dihydro-3-(2-methoxyphenyl)-5-isoxazolecarboxamide;
N-[4-[5-cyclopropyl-3-(trifluoromethyl)-1H-pyrazol-1-yl]phenyl]-2-[4-(1,1-dimethylethyl)phenyl]-cyclopropanecarboxamide;
N-[4-[5-cyclopropyl-3-(trifluoromethyl)-1H-pyrazol-1-yl]phenyl]-3-pyridine carboxamide;
N-[4-[3-cyclopropyl-5-(trifluoromethyl)-1H-pyrazol-1-yl]phenyl]-3-pyridine carboxamide; or
N-benzyl-6-(3,5-dicyclopropyl-1H-pyrazol-1-yl)pyridazin-3-amine.

In one preferred embodiment, $R^1$ is cyclopropyl.
In one preferred embodiment, $R^2$ is $CF_3$.
According to one preferred embodiment, Hy is

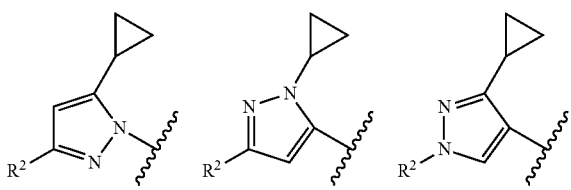

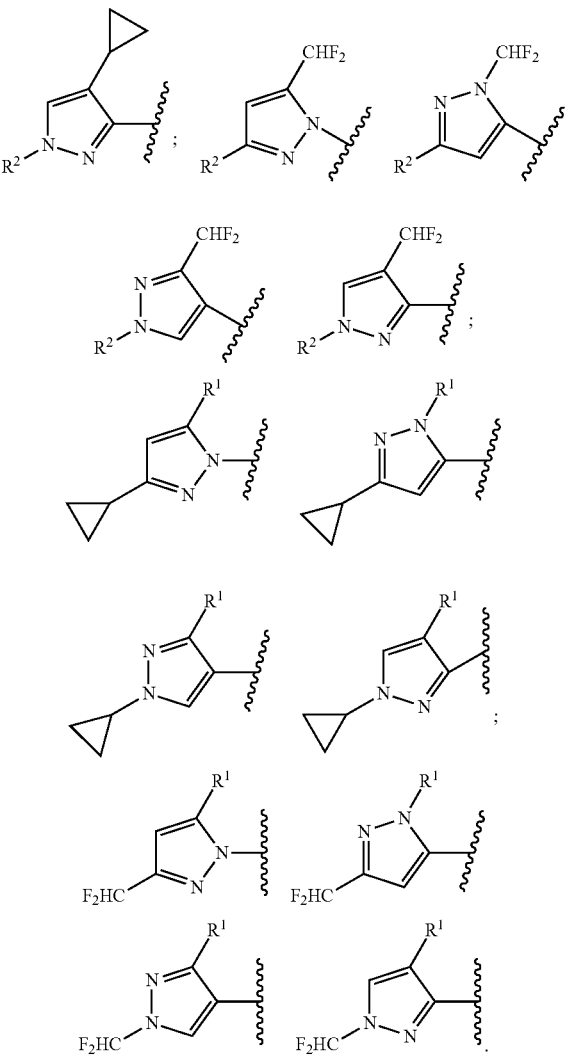

Further preferred is a compound of formula (I) wherein Hy is

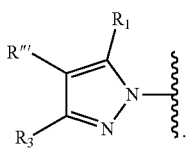

Further preferred is a compound of formula (I) wherein Hy is

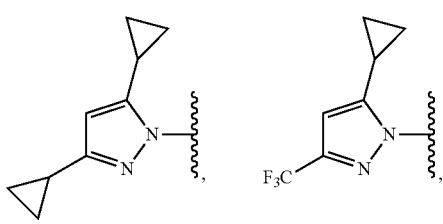

-continued

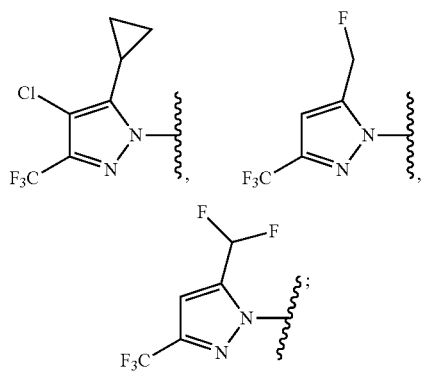

According to one preferred embodiment, Ar is

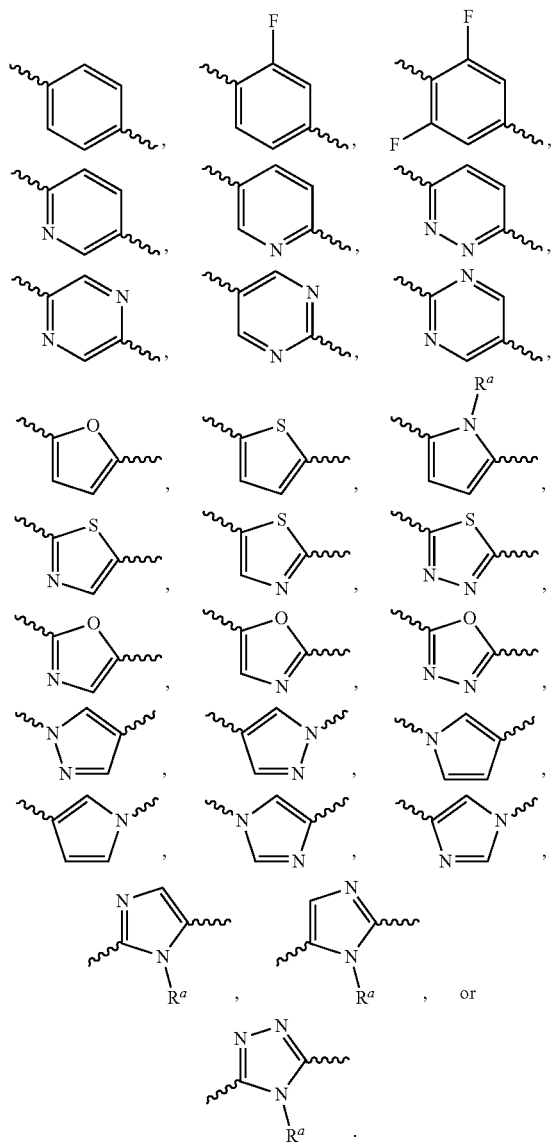

Further preferred is a compound of formula (I) wherein Ar is

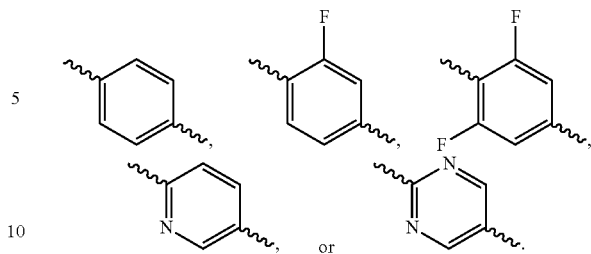

Further preferred is a compound of formula (I) wherein Ar is

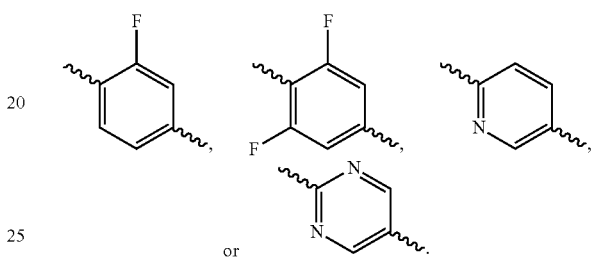

According to one preferred embodiment, $L_1$ and $L_2$ together represent —NH—C(═O)—, —NH—S(═O)$_q$—, —C(═O)NH— or —NH—CH$_2$—.

According to one preferred embodiment, A is absent or selected from —(CR'R")—, O, S(═O)$_q$, C(═X) and —NR$^a$. More preferably, A is —CH$_2$—, —CHMe- or —(CR'R")—, where R' and R" are joined to form a substituted or unsubstituted saturated or unsaturated 3-6 member ring, which may optionally include one or more heteroatoms which are the same or different and are selected from O, NR$^a$ (such as NH) and S;

Further preferred is a compound of formula (I) wherein A is

—CH$_2$—

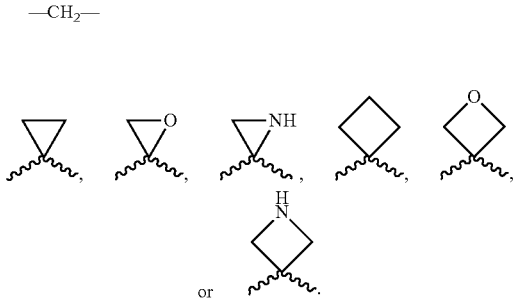

Further preferred is a compound of formula (I) wherein A is

—CH$_2$—, —CHMe—,

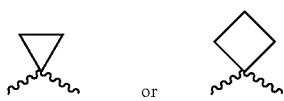

Further preferred is a compound of formula (I) wherein A is absent.

Further preferred is a compound of formula (I) wherein A is —CH$_2$—.
According to one preferred embodiment, Cy is
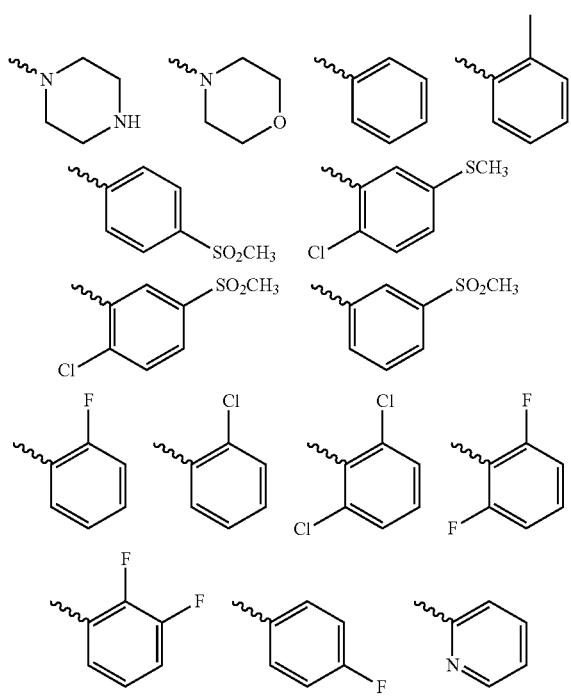
Further preferred is a compound of formula (I) wherein Cy is
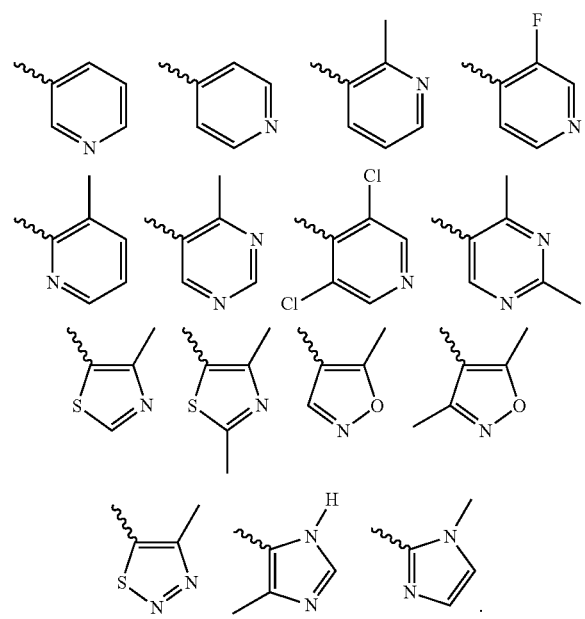
Further preferred is a compound of formula (I) wherein Cy is
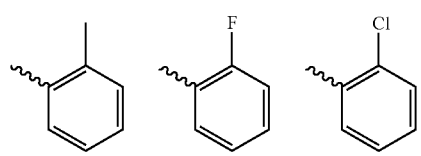
-continued
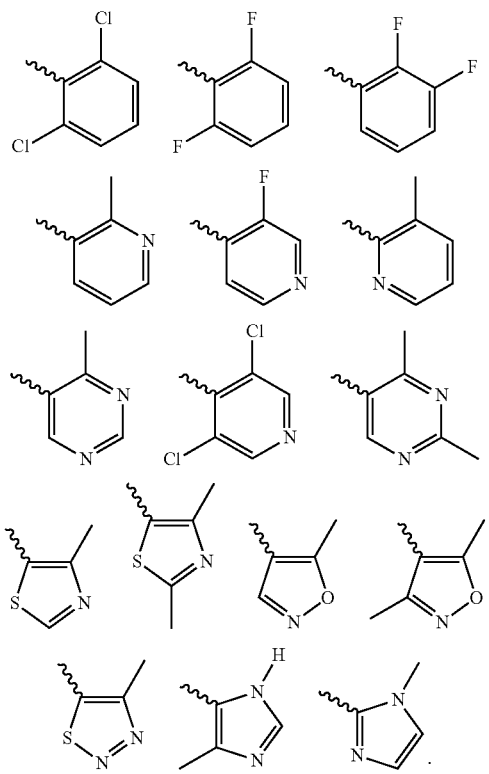
Further preferred is a compound of formula (I) wherein Cy is
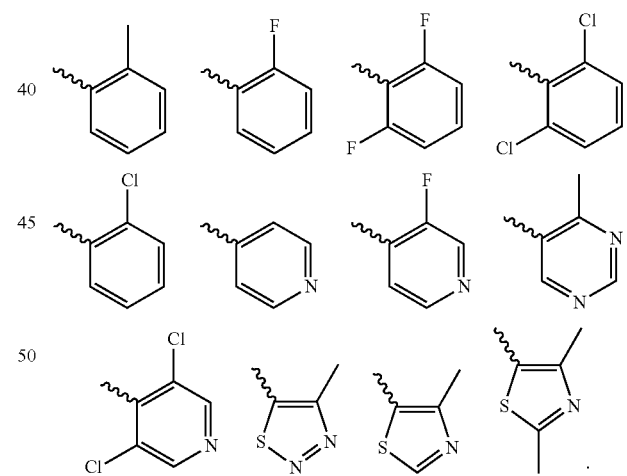
Further preferred is a compound of formula (I) wherein Cy is
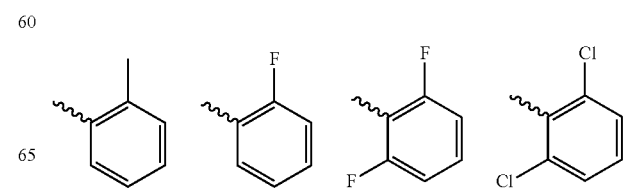

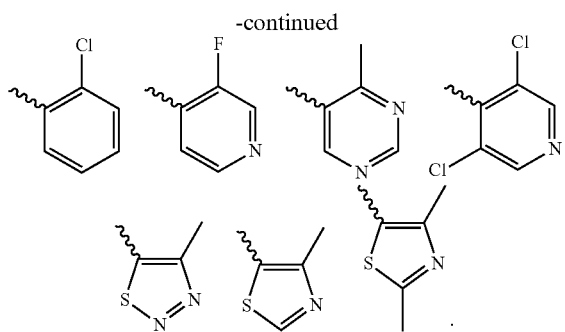

Yet another embodiment is a compound having the formula (IA):

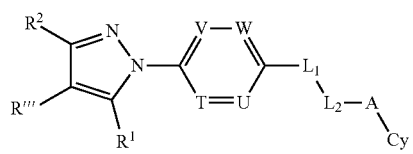

or a tautomer thereof, prodrug thereof, N-oxide thereof, pharmaceutically acceptable ester thereof, or pharmaceutically acceptable salt thereof, wherein the variables (e.g., R''', $R^1$, $R^2$, T, U, V, W, $L_1$, $L_2$, A and Cy) are defined as described above in relation to formula (I), with the proviso that the compound of formula (IA) is not any of the compounds in Proviso ((a-e) defined above.

Further preferred is a compound of formula (IA-I)

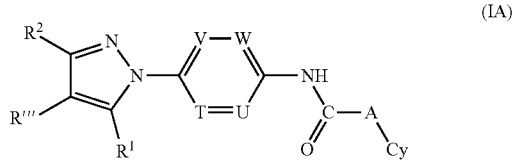

or a tautomer thereof, prodrug thereof, N-oxide thereof, pharmaceutically acceptable ester thereof, or pharmaceutically acceptable salt thereof, wherein the variables (e.g., R''', $R^1$, $R^2$ T, U, V, W, A and Cy) are defined as described above in relation to formula (I), with the proviso that the compound of formula (IA) is not any of the compounds in Proviso (a-e) defined above.

Further preferred is a compound of formula (IA-I)

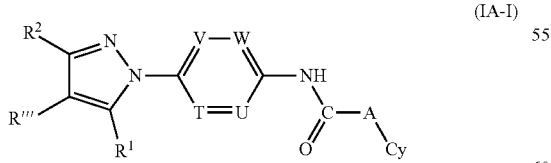

or a tautomer thereof, prodrug thereof, N-oxide thereof, pharmaceutically acceptable ester thereof, or pharmaceutically acceptable salt thereof, wherein $R^1$ and $R^2$ are the same or different and are independently selected from $CH_2F$, $CHF_2$, $CF_3$ and cyclopropyl; with the proviso that a) both $R^1$ and $R^2$ at the same time do not represent $CF_3$,;
R''' is hydrogen or halogen;
T, U, V, W are independently $CR^a$ or N;
$R^a$ is hydrogen or halogen;
A is absent; and
Cy is selected from monocyclic substituted or unsubstituted aryl or monocyclic substituted or unsubstituted heteroaryl,
with the proviso that the compound of formula (IA) is not any of the compounds in Proviso (e) defined above.

Further preferred is a compound of formula (IA-I) wherein both $R^1$ and $R^2$ represent cyclopropyl.

Further preferred is a compound of formula (IA-I) wherein one of $R^1$ and $R^2$ is $CF_3$ and the other is cyclopropyl.

Further preferred is a compound of formula (IA-I) wherein $R^1$ is cyclopropyl and $R^2$ is $CF_3$.

Further preferred is a compound of formula (IA-I) wherein T, U, V, W are CH, CF or N.

Further preferred is a compound of formula (IA-I) wherein T is CF or N and each of U, V and W is CH.

Further preferred is a compound of formula (IA-I) wherein each of T and V is CF or N and each of U and W is CH.

Further preferred is a compound of formula (IA-I) wherein A is absent

Further preferred is a compound of formula (IA-I) wherein Cy is selected from

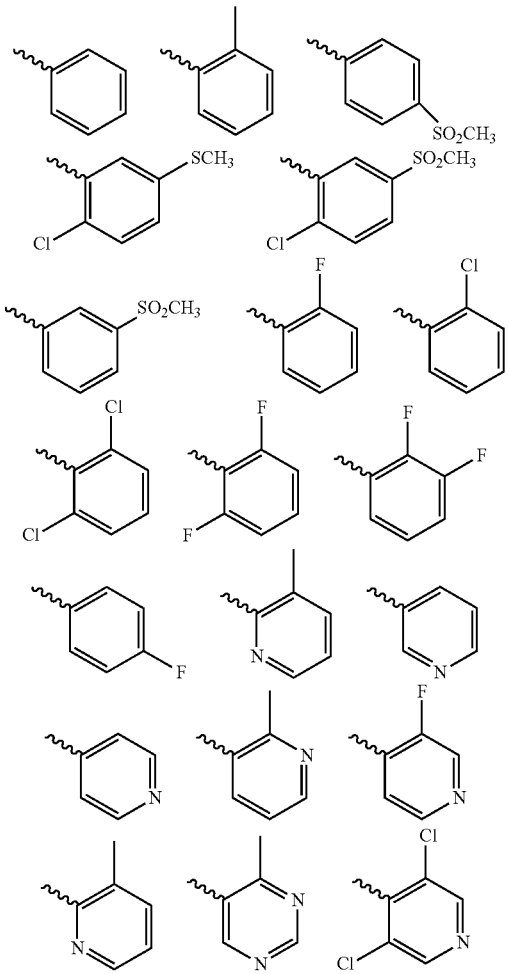

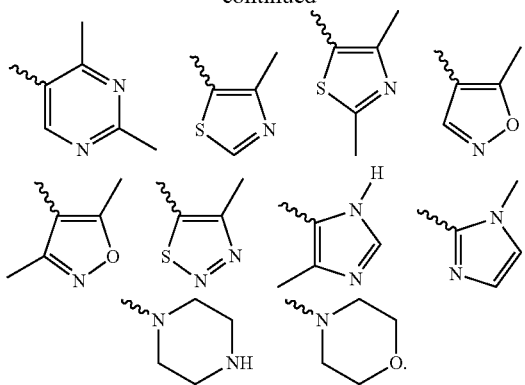

Further preferred is a compound of formula (IA-I) wherein Cy is

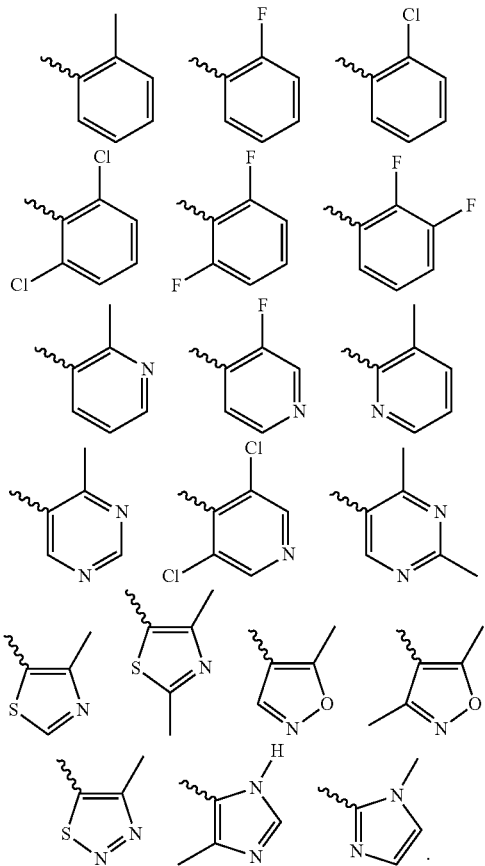

Yet another embodiment is a compound having the formula (IA-III)

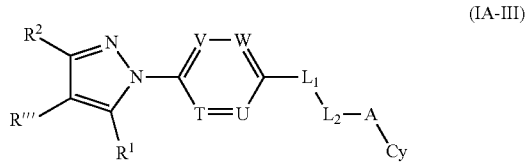

(IA-III)

or a tautomer, prodrug, N-oxide, pharmaceutically acceptable ester, or pharmaceutically acceptable salt thereof, wherein $R^1$ and $R^2$ are the same or different and are independently selected from $CH_2F$, $CHF_2$, $CF_3$, Cyclopropyl with the proviso that both $R^1$ and $R^2$ at the same time do not represent $CF_3$;

T and V are the same or different and are independently selected from CF and N;

Each of U and V is $CR^a$;

$L_1$ and $L_2$ together represent —NH—C(=X)—, —NH—S(=O)$_q$—, —C(=X)NH—, or —S(=O)$_q$NH— or —NH—CR'R"—;

A is absent or selected from —(CR'R")— and —$NR^a$;

each occurrence of R' and R" are the same or different and are independently selected from hydrogen or substituted or unsubstituted $C_{(1-6)}$ alkyl group or R' and R" may be joined to form a substituted or unsubstituted saturated or unsaturated 3-6 membered ring, which may optionally include one or more heteroatoms which may be same or different and are selected from O, $NR^a$ and S;

R''' is selected from the group consisting of hydrogen, or halogen each occurrence of X is independently selected from O, S and —$NR^a$;

Cy is selected from monocyclic substituted or unsubstituted heterocyclyl, monocyclic substituted or unsubstituted aryl, and monocyclic substituted or unsubstituted heteroaryl.

each occurrence of $R^a$ and $R^b$ are the same or different and are independently selected from hydrogen, nitro, hydroxy, cyano, halogen, —$OR^c$, —S(=O)$_q$—$R^c$, —$NR^cR^d$, —C(=Y)—R, —$CR^cR^d$—C(=Y)—$R^c$, —$CR^cR^d$—Y—$CR^cR^d$—, —C(=Y)—$NR^cR^d$—, —$NR^cR^d$—C(=Y)—$NR^cR^d$—, —S(=O), —$NR^cR^d$—, —$NR^cR^d$—S(=O)$_q$—$NR^cR^d$—, —$NR^cR^d$—$NR^cR^d$—, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocylyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when $R^a$ and $R^b$ substitutent are directly bound to the same atom, they may be joined to form a substituted or unsubstituted saturated or unsaturated 3-10 member ring, which may optionally include one or more heteroatoms which may be same or different and are selected from O, $NR^c$ and S;

each occurrence of $R^c$ and $R^d$ may be same or different and are independently selected from the group consisting of hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic group, substituted or unsubstituted heterocyclylalkyl, or when two $R^c$ and/or $R^d$ substitutents are directly bound to the same atom, they may be joined to form a substituted or unsubstituted saturated or unsaturated 3-10 member ring, which may optionally include one or more heteroatoms which are the same or different and are selected from O, NH and S;

each occurrence of Y is selected from O, S and —$NR^a$; and each occurrence of q independently represents 0, 1 or 2.

Further preferred is a compound of formula (IA-III) wherein both $R^1$ and $R^2$ represent cyclopropyl.

Further preferred is a compound of formula (IA-III) wherein one of $R^1$ and $R^2$ is $CF_3$ and the other is cyclopropyl.

Further preferred is a compound of formula (IA-III) wherein one of $R^1$ and $R^2$ is $CF_3$ and the other is $CH_2F$, $CHF_2$.

Further preferred is a compound of formula (IA-III) wherein $R^1$ is cyclopropyl and $R^2$ is $CF_3$.

Further preferred is a compound of formula (IA-III) wherein T is CF or N.

Further preferred is a compound of formula (IA-III) wherein U, V, W are CH, CF or N.

Further preferred is a compound of formula (IA-III) wherein $L_1$ and $L_2$ together represent —NH—C(=O)—, C(=O)NH— or —NH—CH$_2$—;

Further preferred is a compound of formula (IA-III) wherein A is absent, —NH— or —CH$_2$—.

Further preferred is a compound of formula (IA-III) wherein Cy is selected from

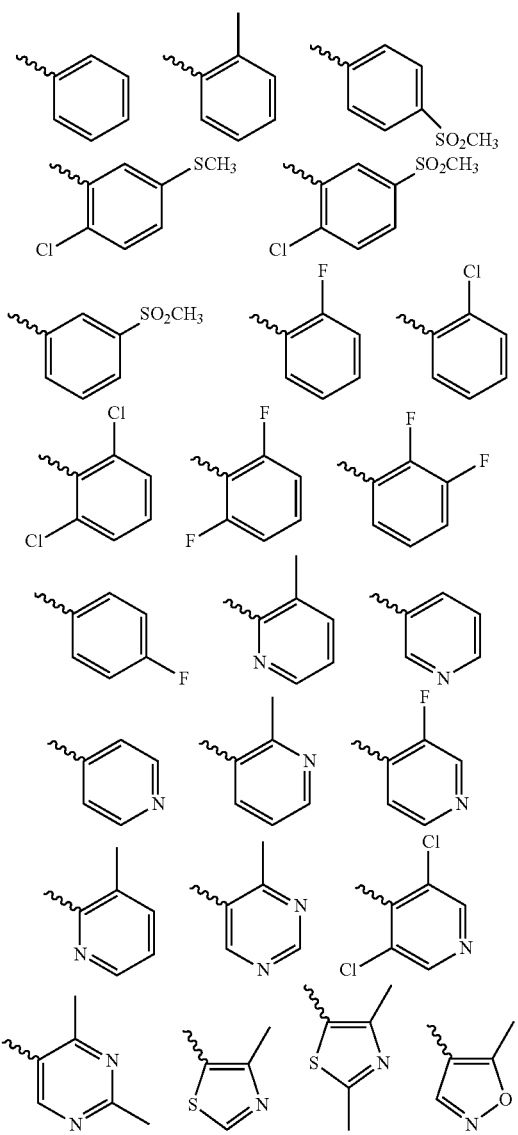

-continued

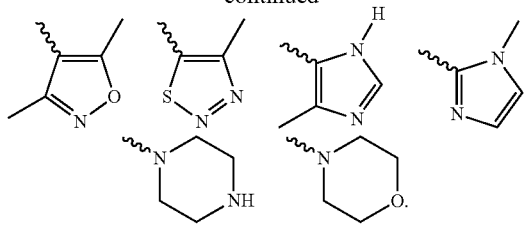

Further preferred is a compound of formula (IA-III) wherein Cy is selected from

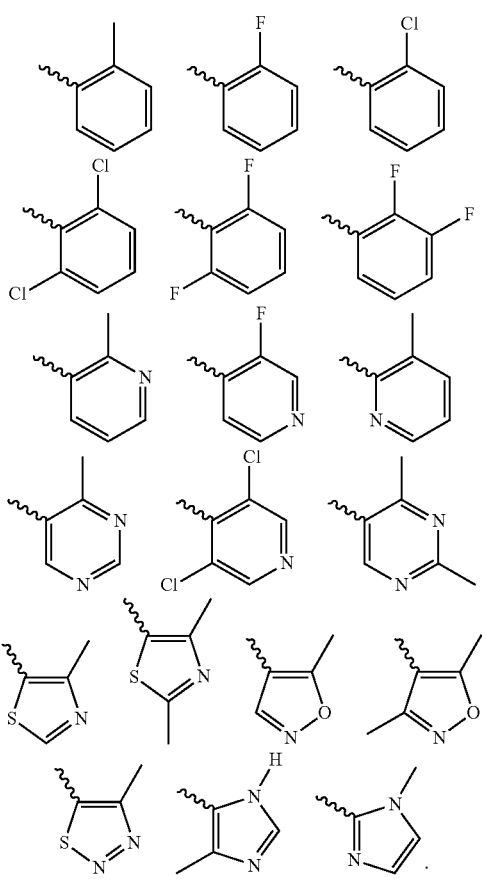

Representative compounds of the present invention include those specified below and in Table 1 and pharmaceutically acceptable salts thereof. The present invention should not be construed to be limited to them.

N-[4-(3,5-dicyclopropyl-1H-pyrazol-1-yl)phenyl]-4-methyl-1,2,3-thiadiazole-5-carboxamide N-[4-(3,5-dicyclopropyl-1H-pyrazol-1-yl)phenyl]-4-methylthiazole-5-carboxamide N-[4-(3,5-dicyclopropyl-1H-pyrazol-1-yl)phenyl]-2,4-dimethylthiazole-5-carboxamide N-[4-(3,5-dicyclopropyl-1H-pyrazol-1-yl)phenyl]-5-methylisoxazole-4-carboxamide N-[4-(3,5-dicyclopropyl-1H-pyrazol-1-yl)phenyl]-3,5-dimethylisoxazole-4-carboxamide N-[4-(3,5-dicyclopropyl-1H-pyrazol-1-yl)phenyl]benzamide N-[4-(3,5-dicyclopropyl-1H-pyrazol-1-yl)phenyl]-2-methylbenzamide N-[4-(3,5-dicyclopropyl-1H-pyrazol-1-yl)phenyl]-2,6-difluorobenzamide
N-[4-(3,5-dicyclopropyl-1H-pyrazol-1-yl)phenyl]-2,3-difluorobenzamide
N-[4-(3,5-dicyclopropyl-1H-pyrazol-1-yl)phenyl-3-(methylsulfonyl)benzamide
N-[4-(3,5-dicyclopropyl-1H-pyrazol-1-yl)phenyl]-4-(methylsulfonyl)benzamide
2-chloro-N-[4-(3,5-dicyclopropyl-1H-pyrazol-1-yl)phenyl]-5-(methylthio)benzamide
2-chloro-N-[4-(3,5-dicyclopropyl-1H-pyrazol-1-yl)phenyl)-5-(methylsulfonyl)benzamide
N-[4-(3,5-dicyclopropyl-1H-pyrazol-1-yl)phenyl]nicotinamide hydrochloride
N-[4-(3,5-dicyclopropyl-1H-pyrazol-1-yl)phenyl]isonicotinamide hydrochloride
N-[4-(3,5-dicyclopropyl-1H-pyrazol-1-yl)phenyl]-3-fluoroisonicotinamide
3,5-dichloro-N-(4-(3,5-dicyclopropyl-1H-pyrazol-1-yl)phenyl)isonicotinamide
N-[4-(3,5-dicyclopropyl-1H-pyrazol-1-yl)phenyl]-4-methylpyrimidine-5-carboxamide
N-[4-(3,5-dicyclopropyl-1H-pyrazol-1-yl)phenyl]-2-phenylacetamide
N-[4-(3,5-dicyclopropyl-1H-pyrazol-1-yl)phenyl]-2-(4-fluorophenyl)acetamide
N-[4-(3,5-dicyclopropyl-1H-pyrazol-1-yl)phenyl]-1-phenylcyclopropanecarboxamide
N-[4-(3,5-dicyclopropyl-1H-pyrazol-1-yl)phenyl]-2-(pyridin-2-yl) acetamide hydrochloride
N-[4-(3,5-dicyclopropyl-1H-pyrazol-1-yl)phenyl]-2-(pyridin-3-yl)acetamide hydrochloride
N-[4-(3,5-dicyclopropyl-1H-pyrazol-1-yl)phenyl]-2-(pyridin-4-yl)acetamide hydrochloride
N-[4-(3,5-dicyclopropyl-1H-pyrazol-1-yl)phenyl]-2-(piperazin-1-yl)acetamide hydrochloride
N-[4-(3,5-dicyclopropyl-1H-pyrazol-1-yl)phenyl]-2-morpholinoacetamide
N-[4-(3,5-dicyclopropyl-1H-pyrazol-1-yl)phenyl]benzenesulfonamide
N-[4-(3,5-dicyclopropyl-1H-pyrazol-1-yl)-3-fluorophenyl]-4-methyl-1,2,3-thiadiazole-5-carboxamide
N-[4-(3,5-dicyclopropyl-1H-pyrazol-1-yl)-3-fluorophenyl]-4-methylthiazole-5-carboxamide
N-[4-(3,5-dicyclopropyl-1H-pyrazol-1-yl)-3-fluorophenyl]-3,5-dimethylisoxazole-4-carboxamide
N-[4-(3,5-dicyclopropyl-1H-pyrazol-1-yl)-3-fluorophenyl]-2-methylbenzamide
N-[4-(3,5-dicyclopropyl-1H-pyrazol-1-yl)-3-fluorophenyl]-2,3-difluorobenzamide
N-[4-(3,5-dicyclopropyl-1H-pyrazol-1-yl)-3-fluorophenyl]-2,6-difluorobenzamide
N-[4-(3,5-dicyclopropyl-1H-pyrazol-1-yl)-3-fluorophenyl]nicotinamide hydrochloride
N-[4-(3,5-dicyclopropyl-1H-pyrazol-1-yl)-3-fluorophenyl]isonicotinamide hydrochloride
N-[4-(3,5-dicyclopropyl-1H-pyrazol-1-yl)-3-fluorophenyl]-4-methylpyrimidine-5-carboxamide
N-[4-(4-chloro-3,5-dicyclopropyl-1H-pyrazol-1-yl)-3-fluorophenyl]-4-methyl-1,2,3-thiadiazole-5-carboxamide
N-[6-(3,5-dicyclopropyl-1H-pyrazol-1-yl)pyridin-3-yl]-4-methyl-1,2,3-thiadiazole-5-carboxamide hydrochloride
N-[6-(3,5-dicyclopropyl-1H-pyrazol-1-yl)pyridin-3-yl]-4-methylthiazole-5-carboxamide hydrochloride
N-[6-(3,5-dicyclopropyl-1H-pyrazol-1-yl)pyridin-3-yl]-2,4-dimethylthiazole-5-carboxamide
N-[6-(3,5-dicyclopropyl-1H-pyrazol-1-yl)pyridin-3-yl]-3,5-dimethylisoxazole-4-carboxamide
6-(3,5-dicyclopropyl-1H-pyrazol-1-yl)-N-o-tolylnicotinamide
N-[6-(3,5-dicyclopropyl-1H-pyrazol-1-yl)pyridin-3-yl]-2-fluorobenzamide
N-[6-(3,5-dicyclopropyl-1H-pyrazol-1-yl)pyridin-3-yl]-2,3-difluorobenzamide hydrochloride
N-[6-(3,5-dicyclopropyl-1H-pyrazol-1-yl)pyridin-3-yl]-2,6-difluorobenzamide hydrochloride
N-[6-(3,5-dicyclopropyl-1H-pyrazol-1-yl)pyridin-3-yl]nicotinamide dihydrochloride
N-[6-(3,5-dicyclopropyl-1H-pyrazol-1-yl)pyridin-3-yl]isonicotinamide dihydrochloride
N-[6-(3,5-dicyclopropyl-1H-pyrazol-1-yl)pyridin-3-yl]-3-fluoroisonicotinamide
3,5-dichloro-N-{4-[5-cyclopropyl-3-(trifluoromethyl)-1H-pyrazol-1-yl]phenyl}isonicotinamide
3,5-dichloro-N-[6-(3,5-dicyclopropyl-1H-pyrazol-1-yl)pyridin-3-yl]isonicotinamide hydrochloride
N-[6-(3,5-dicyclopropyl-1H-pyrazol-1-yl)pyridin-3-yl]-4-methylpyrimidine-5-carboxamide hydrochloride
N-{4-[5-cyclopropyl-3-(trifluoromethyl)-1H-pyrazol-1-yl]phenyl}-4-methyl-1,2,3-thiadiazole-5-carboxamide
N-{4-[5-cyclopropyl-3-(trifluoromethyl)-1H-pyrazol-1-yl]phenyl}-4-methylthiazole-5-carboxamide
N-{4-[5-cyclopropyl-3-(trifluoromethyl)-1H-pyrazol-1-yl]phenyl}-N,4-dimethylthiazole-5-carboxamide
N-{4-[5-cyclopropyl-3-(trifluoromethyl)-1H-pyrazol-1-yl]phenyl}-2,4-dimethylthiazole-5-carboxamide
N-{4-[5-cyclopropyl-3-(trifluoromethyl)-1H-pyrazol-1-yl]phenyl}-5-methylisoxazole-4-carboxamide
N-{4-[5-cyclopropyl-3-(trifluoromethyl)-1H-pyrazol-1-yl]phenyl}-3,5-dimethylisoxazole-4-carboxamide
N-{4-[5-cyclopropyl-3-(trifluoromethyl)-1H-pyrazol-1-yl]phenyl}-1-methyl-1H-imidazole-2-carboxamide
N-{4-[3-cyclopropyl-5-(trifluoromethyl)-1H-pyrazol-1-yl]phenyl}-4-methyl-1H-imidazole-5-carboxamide
N-{4-[5-cyclopropyl-3-(trifluoromethyl)-1H-pyrazol-1-yl]phenyl}-2-methylbenzamide
N-{4-[5-cyclopropyl-3-(trifluoromethyl)-1H-pyrazol-1-yl]phenyl}-2,3-difluorobenzamide
N-{4-[5-cyclopropyl-3-(trifluoromethyl)-1H-pyrazol-1-yl]phenyl}-2,6-difluorobenzamide
N-{4-[5-cyclopropyl-3-(trifluoromethyl)-1H-pyrazol-1-yl]phenyl}-3-(methylsulfonyl)benzamide
2-chloro-N-{4-[5-cyclopropyl-3-(trifluoromethyl)-1H-pyrazol-1-yl]phenyl}-5-(methylthio)benzamide
2-chloro-N-{4-[5-cyclopropyl-3-(trifluoromethyl)-1H-pyrazol-1-yl]phenyl}-5-(methylsulfonyl)benzamide
N-{4-[5-cyclopropyl-3-(trifluoromethyl)-1H-pyrazol-1-yl]phenyl}pyridine-4-carboxamide hydrochloride
N-{4-[5-cyclopropyl-3-(trifluoromethyl)-1H-pyrazol-1-yl]phenyl}-3-fluoro isonicotinamide
N-{4-[5-cyclopropyl-3-(trifluoromethyl)-1H-pyrazol-1-yl]phenyl}-4-methylpyrimidine-5-carboxamide
N-{4-[5-cyclopropyl-3-(trifluoromethyl)-1H-pyrazol-1-yl]phenyl}-2,4-dimethyl pyrimidine-5-carboxamide
N-{4-[5-cyclopropyl-3-(trifluoromethyl)-1H-pyrazol-1-yl]phenyl}-2-(4-fluorophenyl)acetamide
N-{4-[5-cyclopropyl-3-(trifluoromethyl)-1H-pyrazol-1-yl]phenyl}-2-(pyridin-2-yl)acetamide hydrochloride
N-{4-[5-cyclopropyl-3-(trifluoromethyl)-1H-pyrazol-1-yl]phenyl}-2-(pyridin-3-yl)acetamide hydrochloride
N-{4-[5-cyclopropyl-3-(trifluoromethyl)-1H-pyrazol-1-yl]phenyl}-2-(pyridin-4-yl)acetamide hydrochloride 4-[5-cyclopropyl-3-(trifluoromethyl)-1H-pyrazol-1-yl]-N-[(4-methylthiazol-5-yl)methyl]aniline
1-{4-[5-cyclopropyl-3-(trifluoromethyl)-1H-pyrazol-1-yl]phenyl}-3-(4-methyl-1,2,3-thiadiazol-5-yl)urea
1-{4-[5-cyclopropyl-3-(trifluoromethyl)-1H-pyrazol-1-yl]phenyl}-3-(4-methylthiazol-5-yl)urea
1-{4-[5-cyclopropyl-3-(trifluoromethyl)-1H-pyrazo-1-yl]phenyl}-3-(4-methylpyrimidin-5-yl)urea
4-[5-cyclopropyl-3-(trifluoromethyl)-1H-pyrazol-1-yl]-N-(4-methylthiazol-5-yl)benzamide
4-[5-cyclopropyl-3-(trifluoromethyl)-1H-pyrazol-1-yl]-N-(2,6-difluorophenyl)benzamide
N-{4-[4-chloro-5-cyclopropyl-3-(trifluoromethyl)-1H-pyrazol-1-yl]phenyl}-4-methylthiazole-5-carboxamide
N-{4-[4-chloro-5-cyclopropyl-3-(trifluoromethyl)-1H-pyrazol-1-yl]phenyl}-2-(pyridin-2-yl)acetamide hydrochloride
N-{4-[5-cyclopropyl-3-(trifluoromethyl)-1H-pyrazol-1-yl]-3-fluorophenyl}-4-methyl-1,2,3-thiadiazole-5-carboxamide
N-{4-[5-cyclopropyl-3-(trifluoromethyl)-1H-pyrazol-1-yl]-3-fluorophenyl}-4-methylthiazole-5-carboxamide
N-{4-[5-cyclopropyl-3-(trifluoromethyl)-1H-pyrazol-1-yl]-3-fluorophenyl}-5-methylisoxazole-4-carboxamide
N-{4-[5-cyclopropyl-3-(trifluoromethyl)-1H-pyrazol-1-yl]-3-fluorophenyl}-3,5-dimethylisoxazole-4-carboxamide
N-{4-[5-cyclopropyl-3-(trifluoromethyl)-1H-pyrazol-1-yl]-3-fluorophenyl}-2-methylbenzamide
N-{4-[5-cyclopropyl-3-(trifluoromethyl)-1H-pyrazol-1-yl]-3-fluorophenyl}-2,3-difluorobenzamide
N-{4-[5-cyclopropyl-3-(trifluoromethyl)-1H-pyrazol-1-yl]-3-fluorophenyl}-2,6-difluorobenzamide
N-{4-[5-cyclopropyl-3-(trifluoromethyl)-1H-pyrazol-1-yl]-3-fluorophenyl}nicotinamide hydrochloride
N-{4-[5-cyclopropyl-3-(trifluoromethyl)-1H-pyrazol-1-yl]-3-fluorophenyl}isonicotinamide hydrochloride
N-{4-[5-cyclopropyl-3-(trifluoromethyl)-1H-pyrazol-1l-yl]-3-fluorophenyl}-3-fluoroisonicotinamide 3,5-dichloro-N-{4-[5-cyclopropyl-3-(trifluoromethyl)-1H-pyrazol-1-yl]-3-fluorophenyl}isonicotinamide
N-{4-[5-cyclopropyl-3-(trifluoromethyl)-1H-pyrazol-1-yl]-3-fluorophenyl}-4-methylpyrimidine-5-carboxamide
N-{4-[5-cyclopropyl-3-(trifluoromethyl)-1H-pyrazol-1-yl]-3-fluorophenyl}-N,4-dimethylpyrimidine-5-carboxamide
N-{4-[4-chloro-5-cyclopropyl-3-(trifluoromethyl)-1H-pyrazol-1-yl]-3-fluorophenyl}-4-methyl-1,2,3-thiadiazole-5-carboxamide
N-{4-[4-chloro-5-cyclopropyl-3-(trifluoromethyl)-1H-pyrazol-1-yl]-3-fluorophenyl}-2-(pyridin-2-yl)acetamide hydrochloride
1-{4-[5-cyclopropyl-3-(trifluoromethyl)-1H-pyrazol-1-yl]-3-fluorophenyl}-3-(4-methylpyrimidin-5-yl)urea
N-{4-[5)-cyclopropyl-3-(trifluromethyl)-1H-pyrazol-1-yl]3-flurophenyl}-2,6-dichloro benzamide
4-[5-cyclopropyl-3-(trifluoromethyl)-1H-pyrazol-1-yl]-N-(2,3-difluorophenyl)-3-fluorobenzamide
4-[5-cyclopropyl-3-(trifluoromethyl)-1H-pyrazol-1-yl]-N-(2,6-difluorophenyl)-3-fluorobenzamide
N-{6-[5-cyclopropyl-3-(trifluoromethyl)-1H-pyrazol-1-yl]pyridin-3-yl}-4-methyl-1,2,3-thiadiazole-5-carboxamide
N-{6-[5-cyclopropyl-3-(trifluoromethyl)-1H-pyrazol-1-yl]pyridin-3-yl}-4-methylthiazole-5-carboxamide hydrochloride
N-{6-[5-cyclopropyl-3-(trifluoromethyl)-1H-pyrazol-1-yl]pyridin-3-yl}-3,5-dimethylisoxazole-4-carboxamide
N-{6-[5-cyclopropyl-3-(trifluoromethyl)-1H-pyrazol-1-yl]pyridin-3-yl}-2-methylbenzamide
2-chloro-N-{6-[5-cyclopropyl-3-(trifluoromethyl)-1H-pyrazol-1-yl]pyridin-3-yl}benzamide hydrochloride
N-(6-(5-cyclopropyl-3-(trifluoromethyl)-1H-pyrazol-1-yl)pyridin-3-yl)-2-fluorobenzamide
N-{6-[5-cyclopropyl-3-(trifluoromethyl)-1H-pyrazol-1-yl]pyridin-3-yl}-2,3-difluorobenzamide
N-{6-[5-cyclopropyl-3-(trifluoromethyl)-1H-pyrazol-1-yl]pyridin-3-yl}-2,6-difluorobenzamide
N-{6-[5-cyclopropyl-3-(trifluoromethyl)-1H-pyrazol-1-yl]pyridin-3-yl}picolinamide
N-{6-[5-cyclopropyl-3-(trifluoromethyl)-1H-pyrazol-1-yl]pyridin-3-yl}-3-methylpicolinamide
N-{6-[5-cyclopropyl-3-(trifluoromethyl)-1H-pyrazol-1-yl]pyridin-3-yl}nicotinamide hydrochloride
N-{6-[5-cyclopropyl-3-(trifluoromethyl)-1H-pyrazol-1-yl]pyridin-3-yl}-2-methylnicotinamide hydrochloride
N-{6-[5-cyclopropyl-3-(trifluoromethyl)-1H-pyrazol-1-yl]pyridin-3-yl}isonicotinamide hydrochloride
N-{6-[5-cyclopropyl-3-(trifluoromethyl)-1H-pyrazol-1-yl]pyridin-3-yl}-3-fluoroisonicotinamide
3,5-dichloro-N-{6-[5-cyclopropyl-3-(trifluoromethyl)-1H-pyrazol-1-yl]pyridin-3-yl}isonicotinamide
N-{6-[5-cyclopropyl-3-(trifluoromethyl)-1H-pyrazol-1-yl]pyridin-3-yl}-4-methylpyrimidine-5-carboxamide
N-{6-[5-cyclopropyl-3-(trifluoromethyl)-1H-pyrazol-1-yl]pyridin-3-yl}-2-(pyridin-2-yl)acetamide hydrochloride
N-{6-[5-cyclopropyl-3-(trifluoromethyl)-1H-pyrazol-1-yl]pyridin-3-yl}-2-(pyridin-4-yl)acetamide hydrochloride
N-{4-[4-chloro-5-cyclopropyl-3-(trifluoromethyl)-1H-pyrazol-1-yl]-3-fluorophenyl}-4-methylpyrimidine-5-carboxamide
1-{6-[3-cyclopropyl-5-(trifluoromethyl)-1H-pyrazol-1-yl]pyridin-3-yl}-3-4 methylthiazol-5-yl)urea
6-[5-cyclopropyl-3-(trifluoromethyl)-1H-pyrazol-1-yl]-N-(2,3-difluorophenyl) nicotinamide
6-[5-cyclopropyl-3-(trifluoromethyl)-1H-pyrazol-1-yl]-N-(2,6-difluorophenyl) nicotinamide
N-{6-[4-chloro-5-cyclopropyl-3-trifluoromethyl-1H-pyrazol-1-yl]pyridin-3-yl}-4-methylthiazole-5-carboxamide
N-{2-[5-cyclopropyl-3-(trifluoromethyl)-1H-pyrazol-1-yl]pyrimidin-5-yl}-2,6-difluorobenzamide
N-{4-[5-(fluoromethyl)-3-(trifluoromethyl)-1H-pyrazol-1-yl]phenyl}-4-methylthiazole-5-carboxamide
N-{4-[5-(difluoromethyl)-3-(trifluoromethyl)-1H-pyrazol-1-yl]phenyl}-4-methylthiazole-5-carboxamide
3,5-dichloro-N-[4-(3,5-dicyclopropyl-1H-pyrazol-1-yl)-3-fluorophenyl]isonicotinamide
N-(2-chloro-6-fluorophenyl)-4-[5-cyclopropyl-3-(trifluoromethyl)-1H-pyrazol-1-yl]-3-fluorobenzamide
N-{2-[5-cyclopropyl-3-(trifluoromethyl)-1H-pyrazol-1-yl]pyrimidin-5-yl}-4-methylthiazole-5-carboxamide
N-{4-[5-cyclopropyl-3-(trifluoromethyl)-1H-pyrazol-1-yl]-3,5-difluorophenyl}-4-methylpyrimidine-5-carboxamide
{4-[5-cyclopropyl-3-(trifluoromethyl)-1H-pyrazol-1-yl]-3-fluorophenyl}-1-phenylcyclobutanecarboxamide
N-{4-[5-cyclopropyl-3-(trifluoromethyl)-1H-pyrazol-1-yl]-3-fluorophenyl}-4-methyloxazole-5-carboxamide
N-{2-[5-cyclopropyl-3-(trifluoromethyl)-1H-pyrazol-1-yl]pyrimidin-5-yl}-4-methylpyrimidine-5-carboxamide
4-[5-cyclopropyl-3-(trifluoromethyl)-1H-pyrazol-1-yl]-3-fluoro-N-(4-methylpyrimidin-5-yl)benzamide or
N-{4-[3-cyclopropyl-5-(difluoromethyl)-1H-pyrazo 1-yl]-3-fluorophenyl}-2,6-difluorobenzamide and N-{4-[5-cyclopropyl-3-(difluoromethyl)-1H-pyrazol-1-yl]-3-fluorophenyl}-2,6-difluorobenzamide
or a tautomer, prodrug, N-oxide, pharmaceutically acceptable ester, or pharmaceutically acceptable salt thereof.

TABLE 1
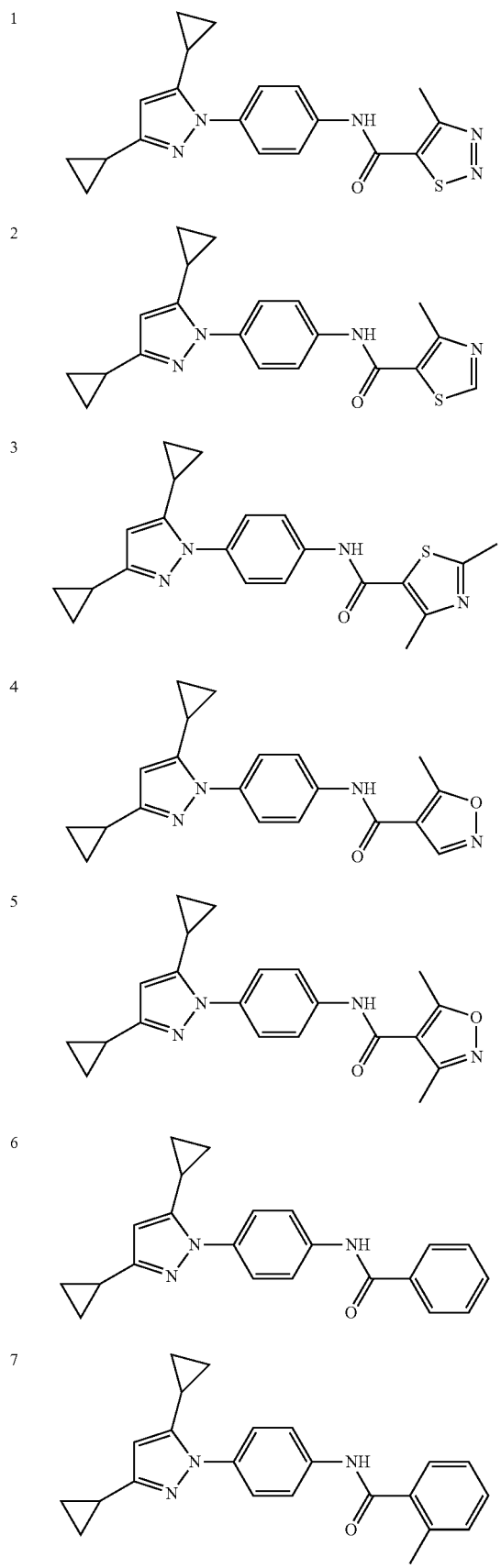
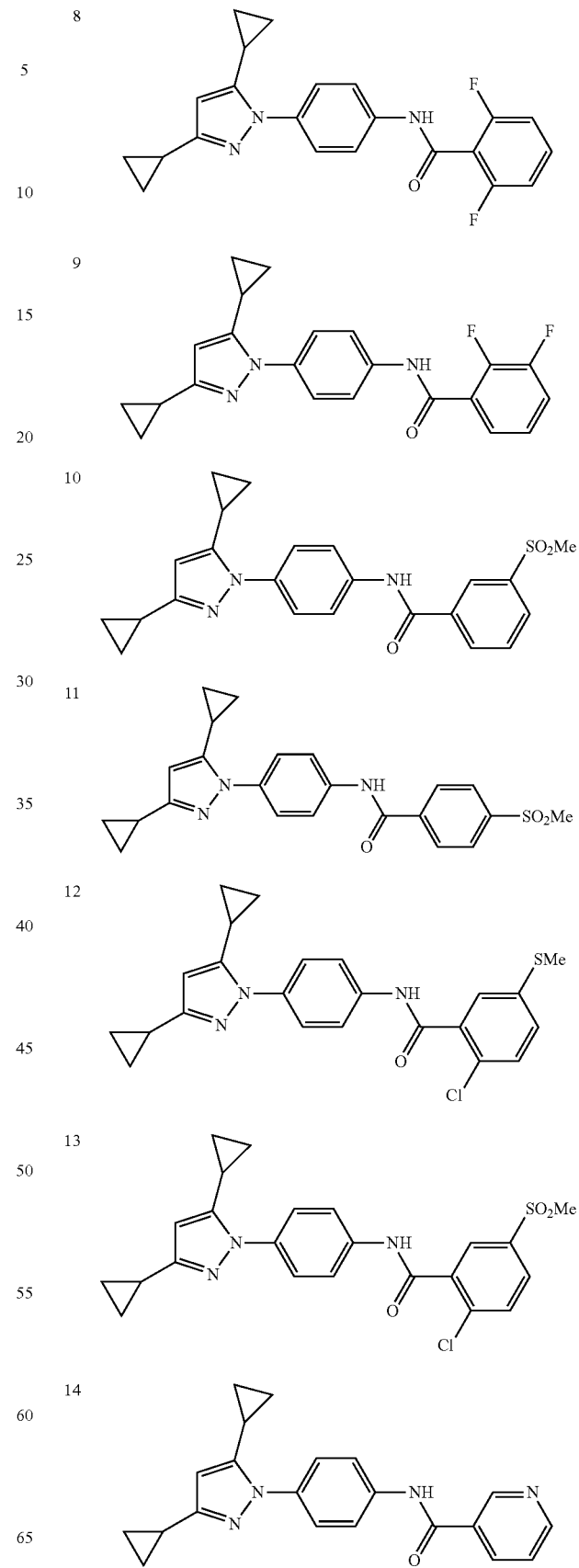

TABLE 1-continued
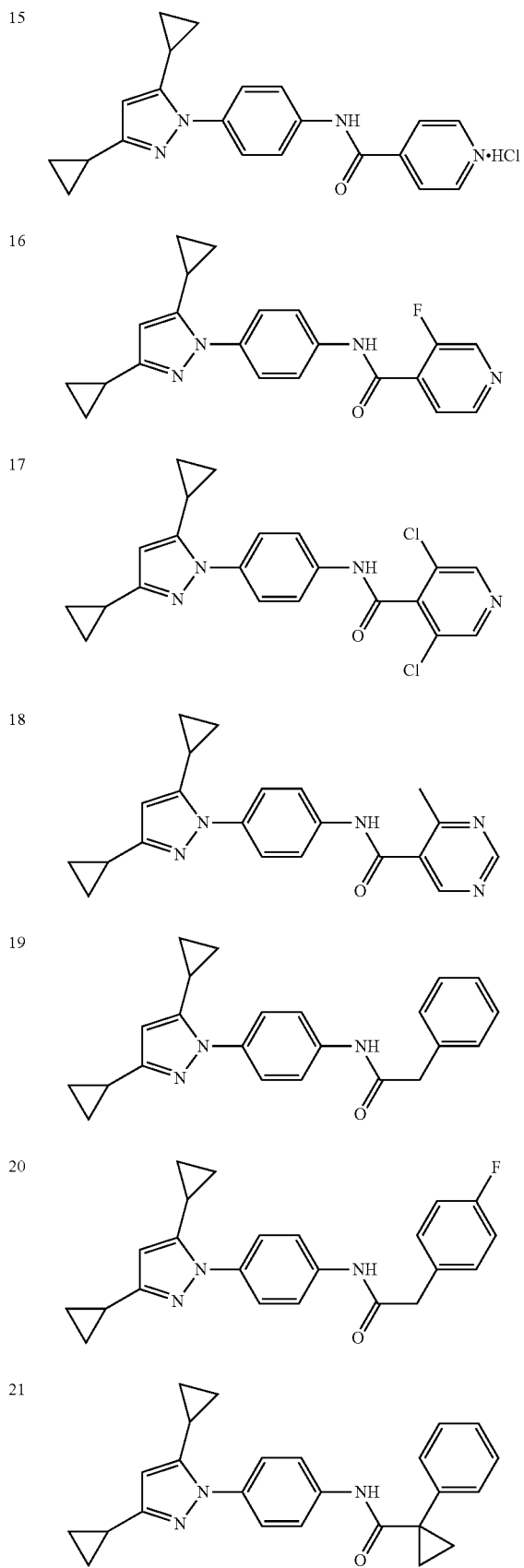
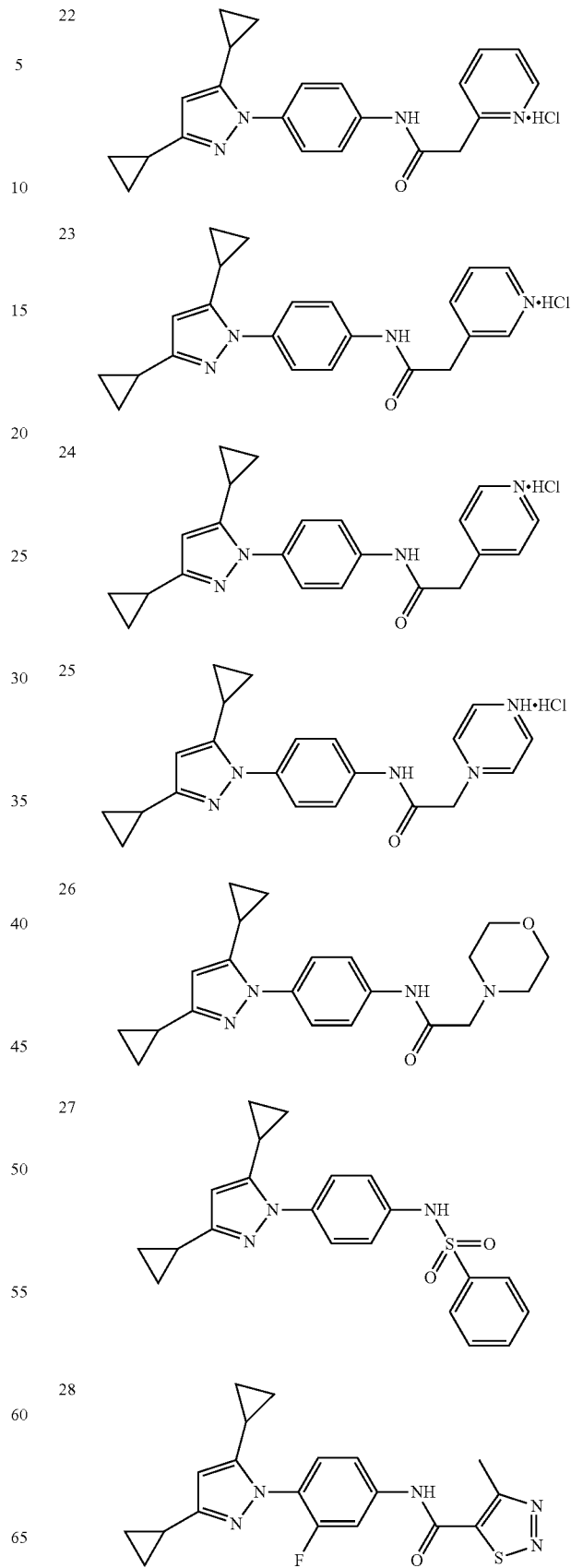

TABLE 1-continued
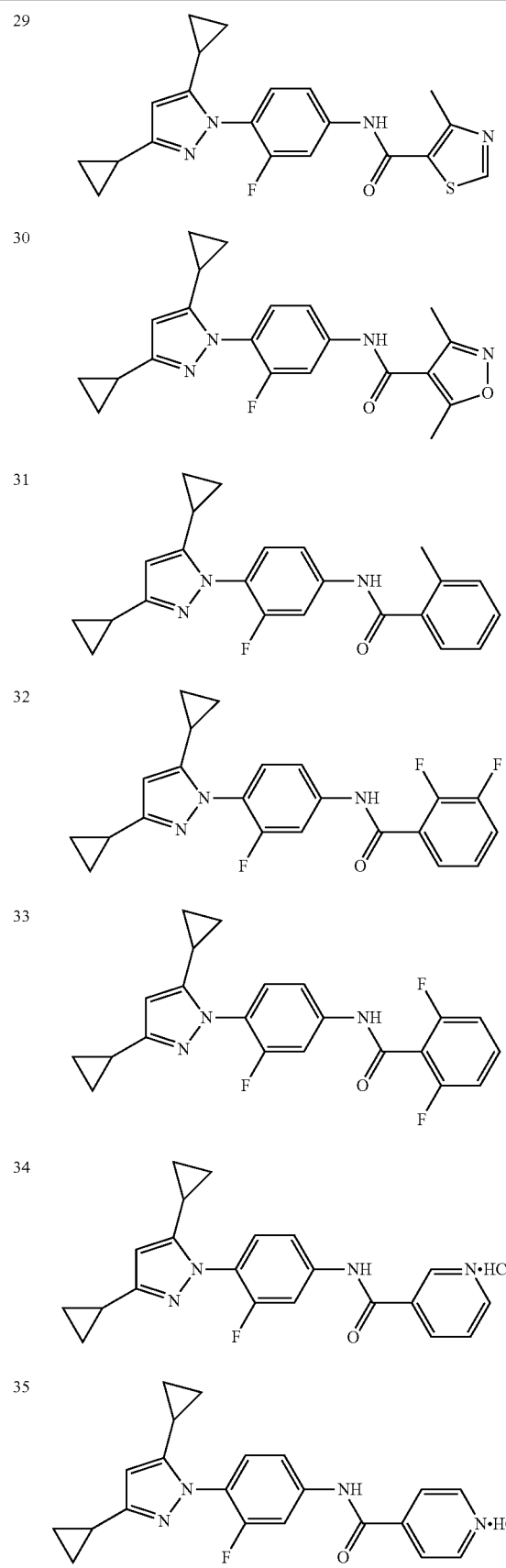
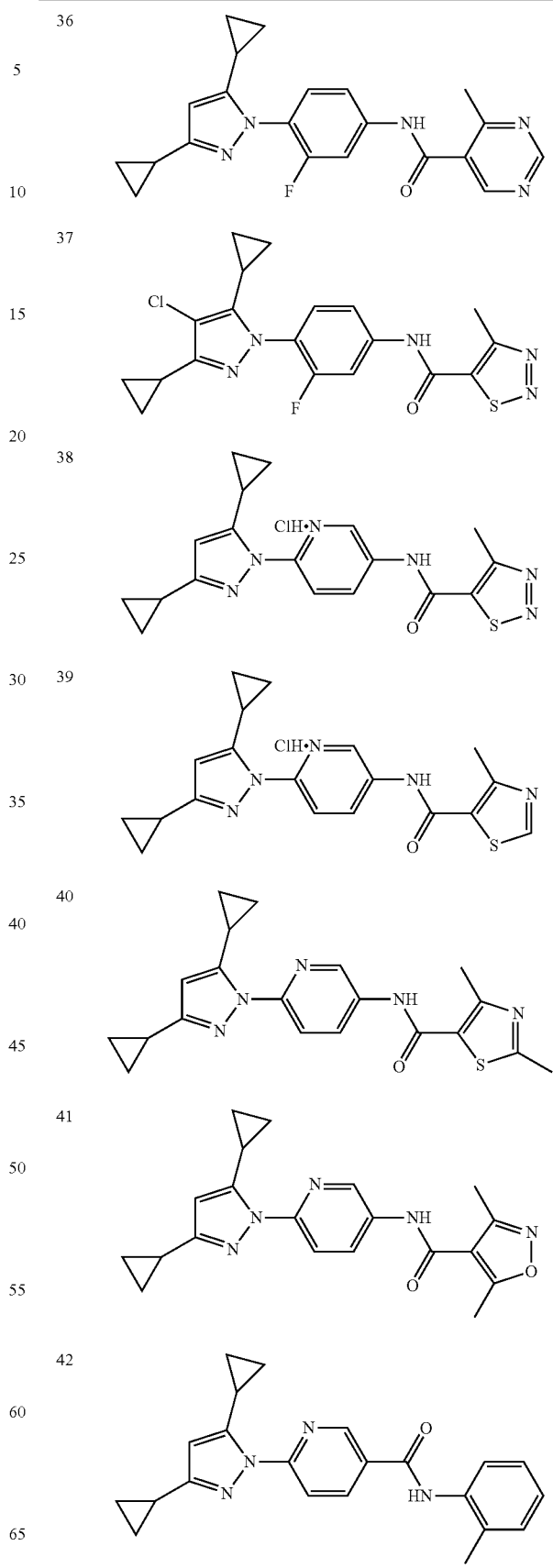

TABLE 1-continued
| | |
|---|---|
| 43 | 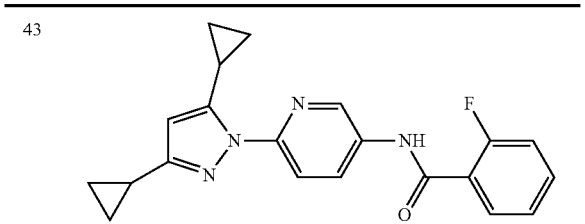 |
| 44 | 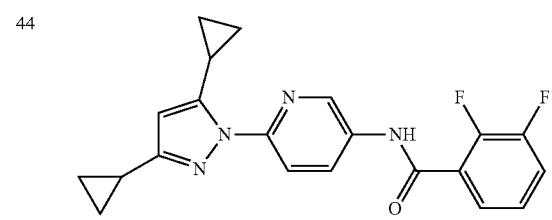 |
| 45 | 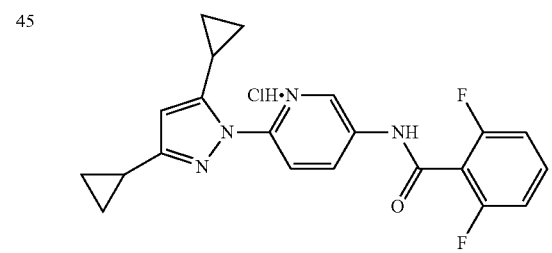 |
| 46 | 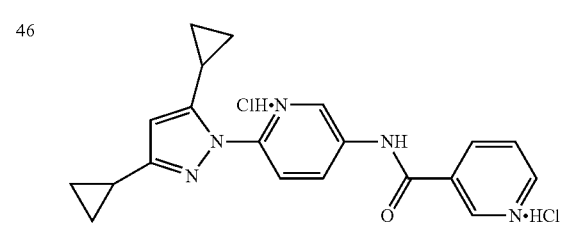 |
| 47 | 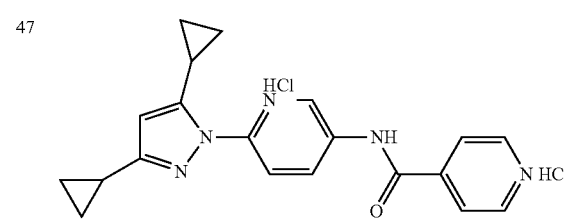 |
| 48 | 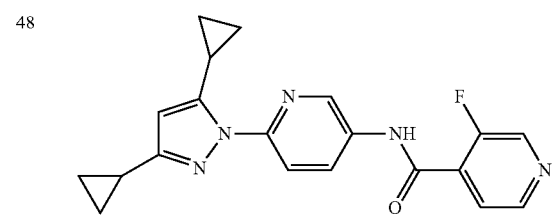 |
| 49 | 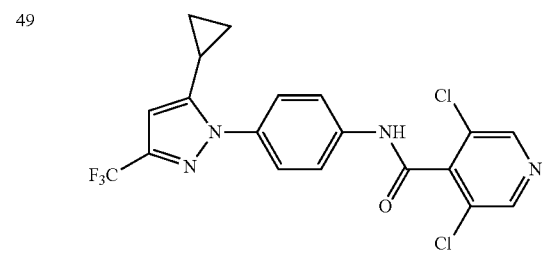 |
| 50 | 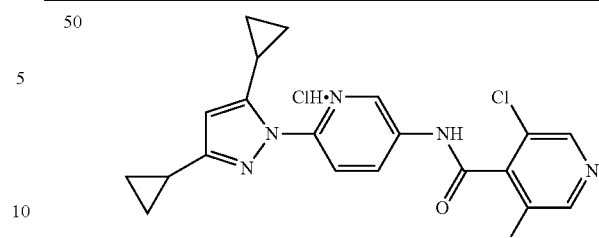 |
| 51 | 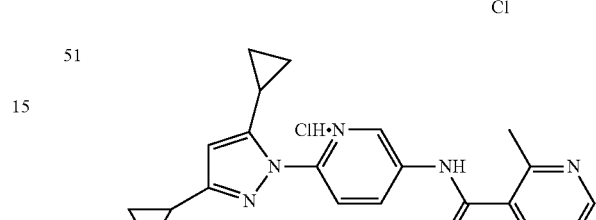 |
| 52 | 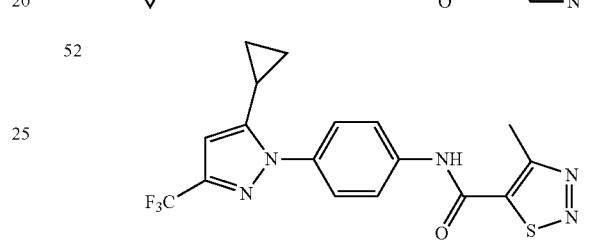 |
| 53 | 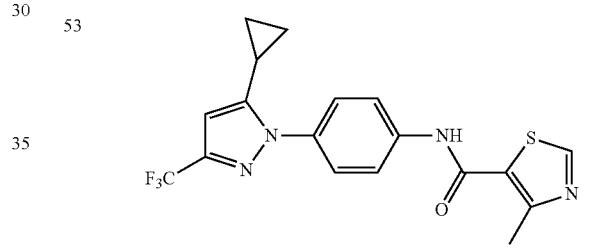 |
| 54 | 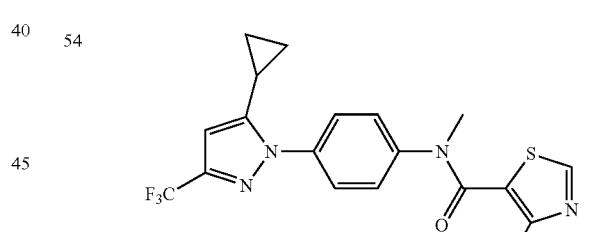 |
| 55 | 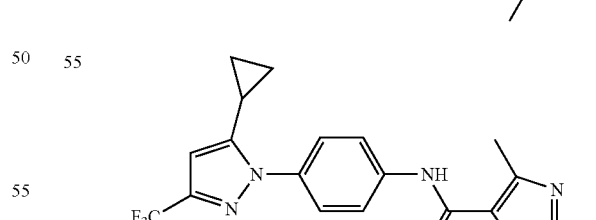 |
| 56 | 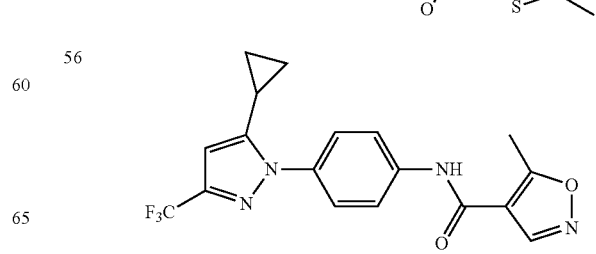 |

TABLE 1-continued
| 57 | 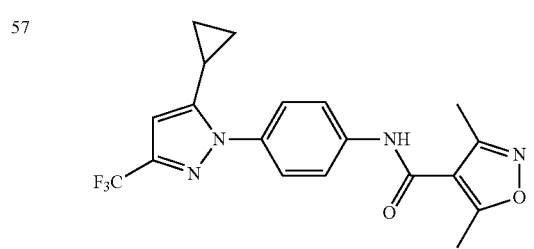 |
| 58 | 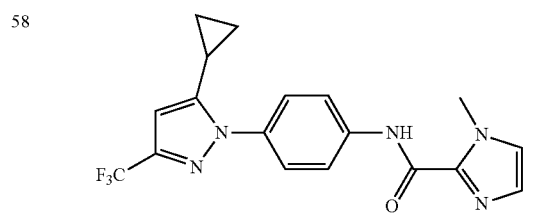 |
| 59 | 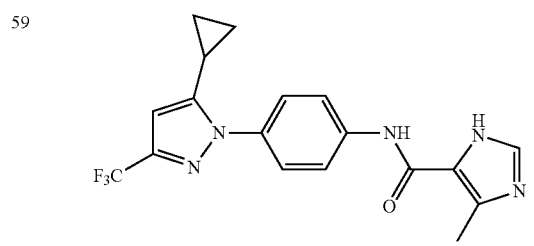 |
| 60 | 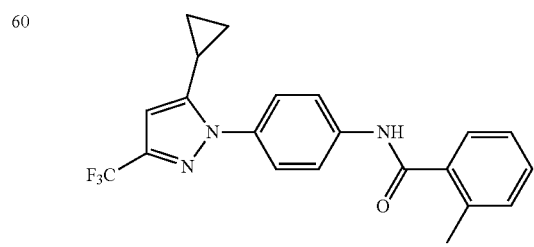 |
| 61 | 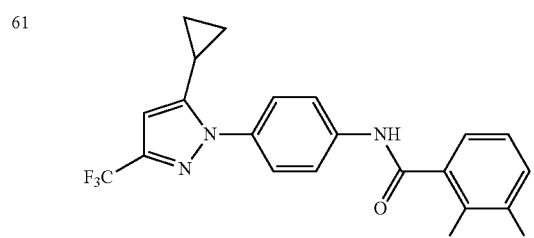 |
| 62 | 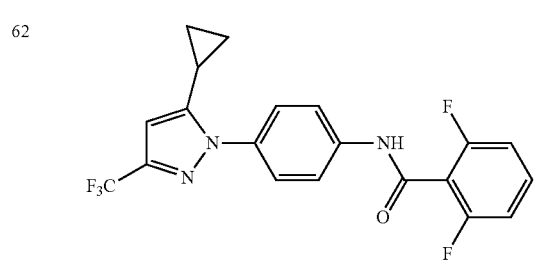 |
| 63 | 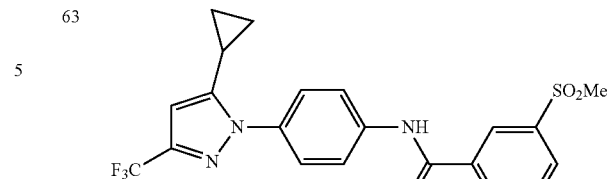 |
| 64 | 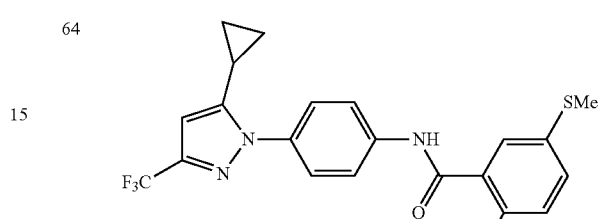 |
| 65 | 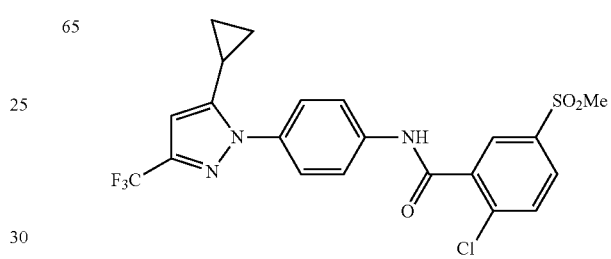 |
| 66 | 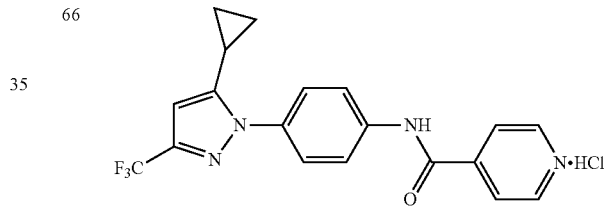 |
| 67 | 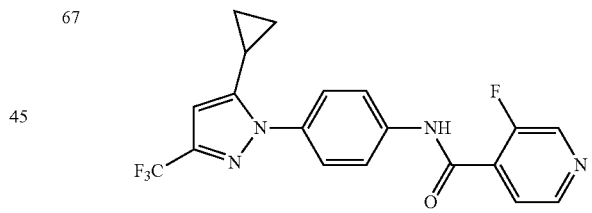 |
| 68 | 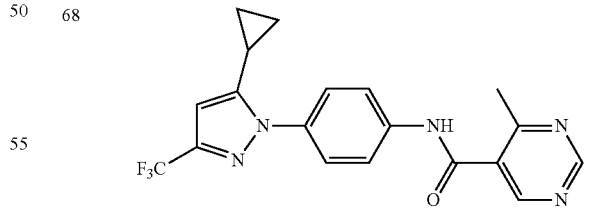 |
| 69 | 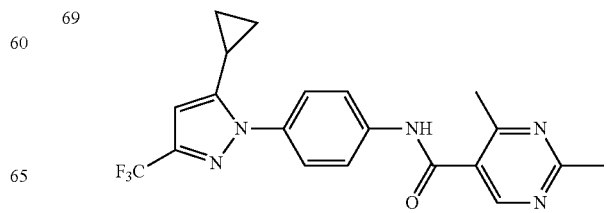 |

TABLE 1-continued
| 70 | 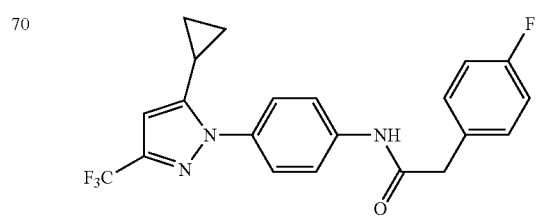 |
| --- | --- |
| 71 | 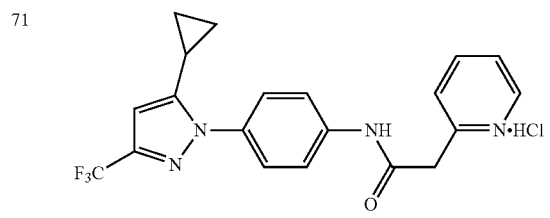 |
| 72 | 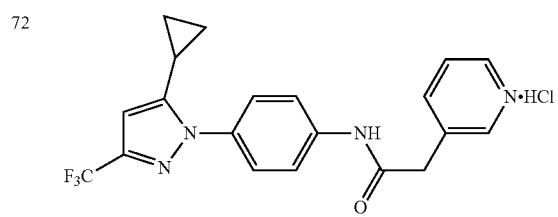 |
| 73 | 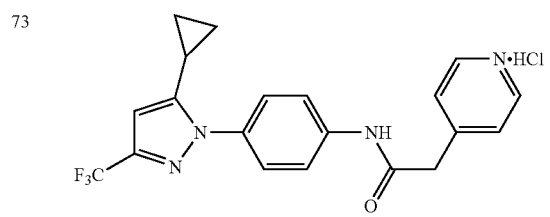 |
| 74 | 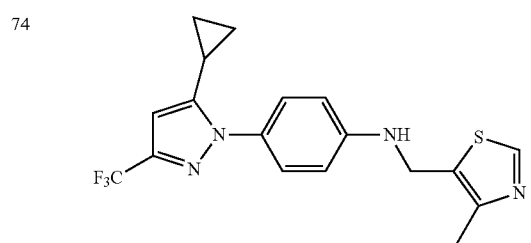 |
| 75 | 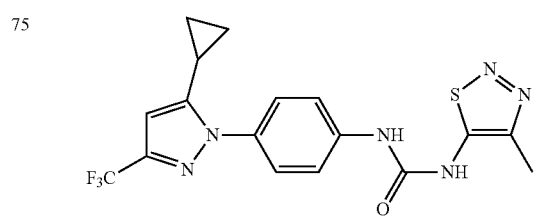 |
| 76 | 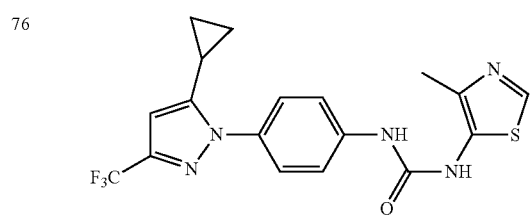 |
TABLE 1-continued
| 77 | 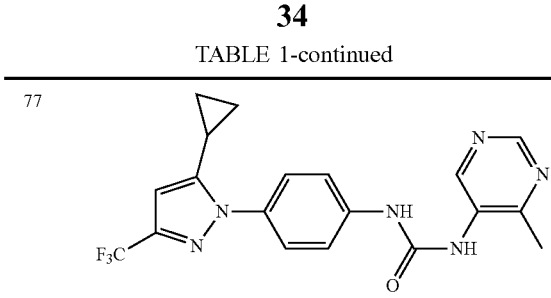 |
| --- | --- |
| 78 | 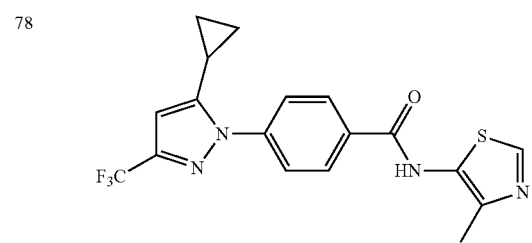 |
| 79 | 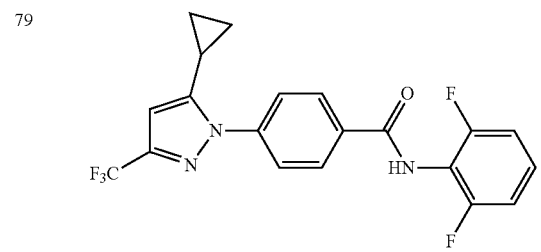 |
| 80 | 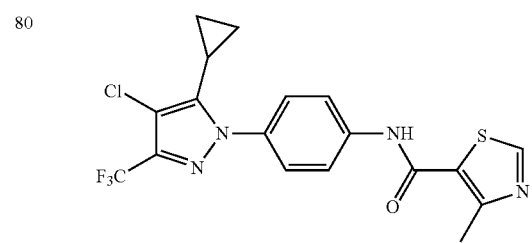 |
| 81 | 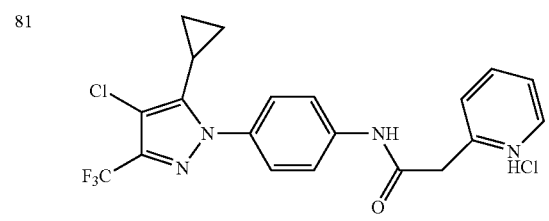 |
| 82 | 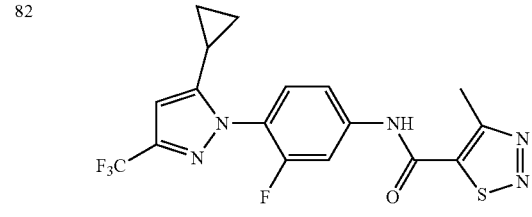 |
| 83 | 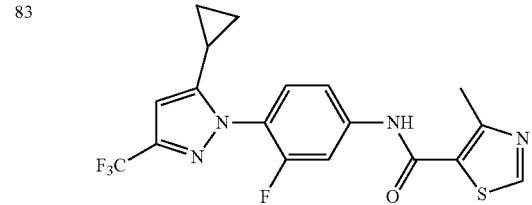 |

TABLE 1-continued

TABLE 1-continued
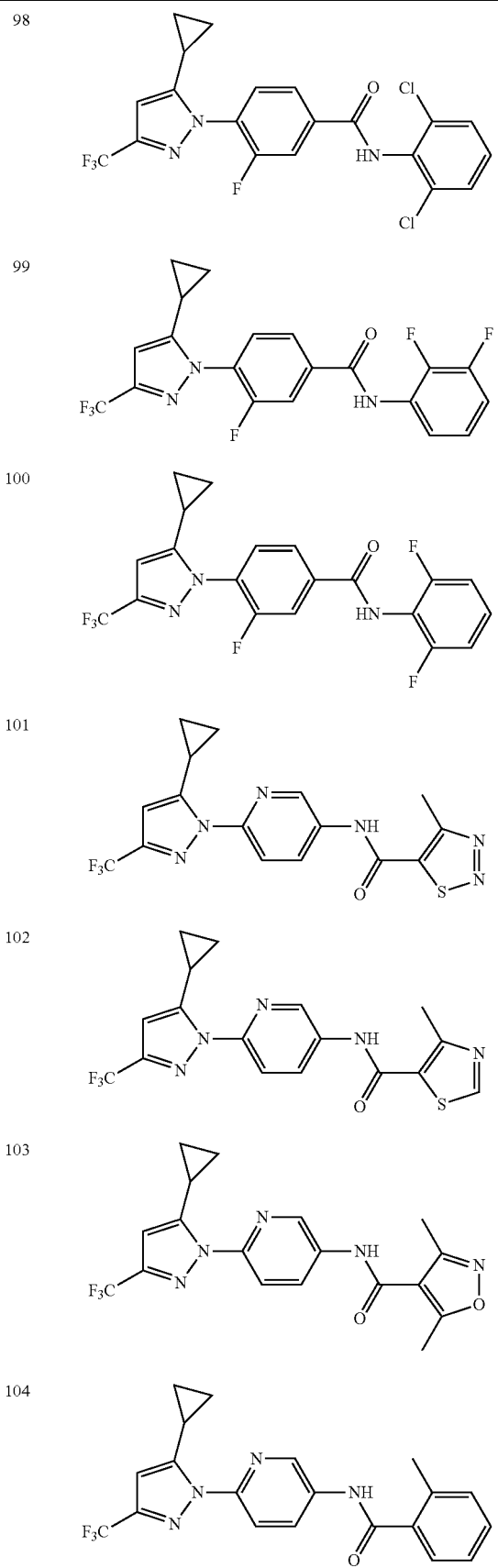
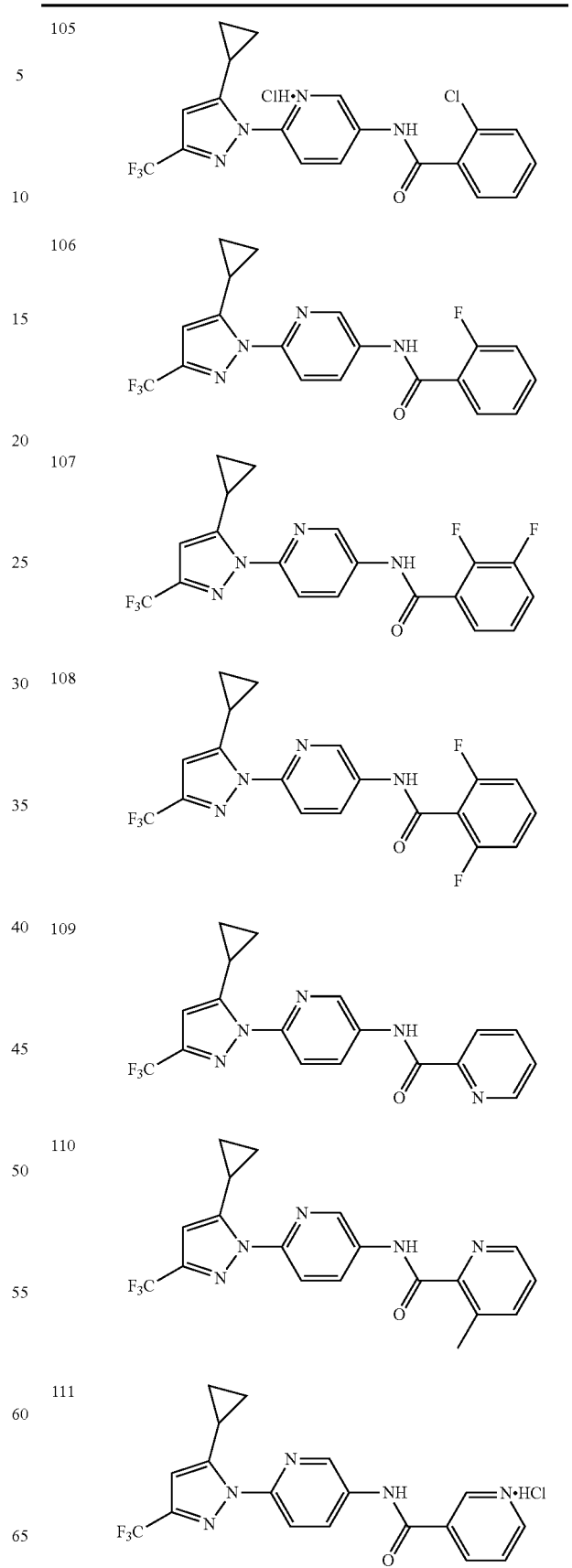

TABLE 1-continued

TABLE 1-continued

| | |
|---|---|
| 126 | 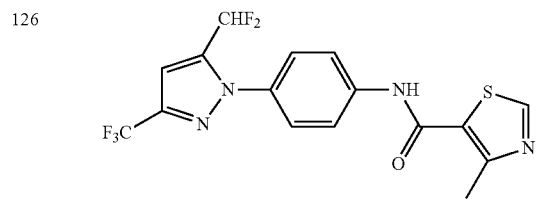 |
| 127 | 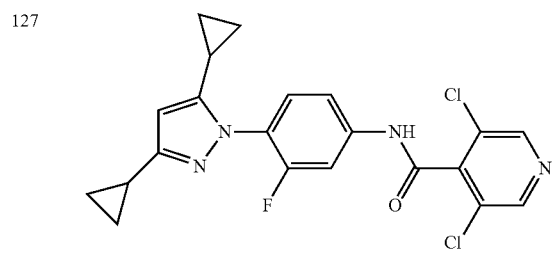 |
| 128 | 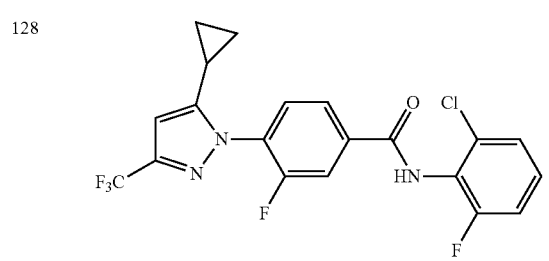 |
| 129 | 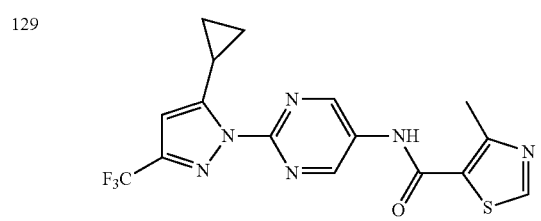 |
| 130 | 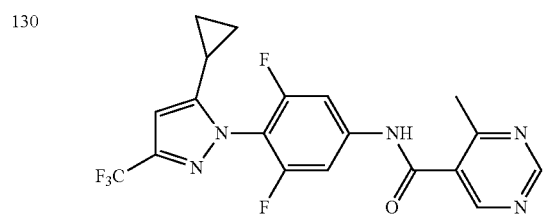 |
| 131 | 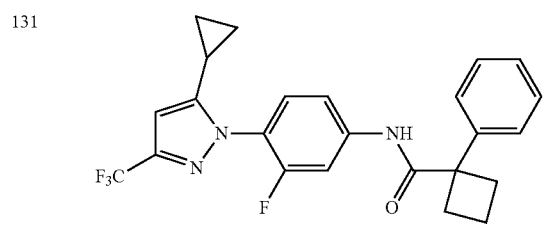 |
| 132 | 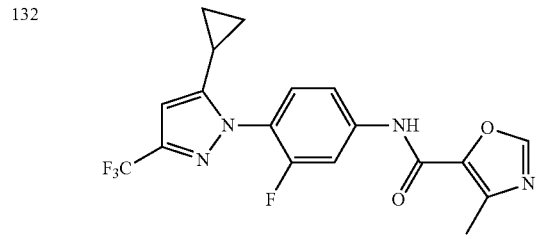 |

TABLE 1-continued

| | |
|---|---|
| 133 | 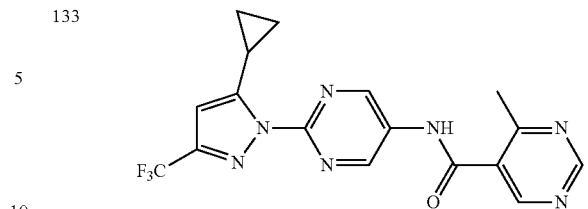 |
| 134 | 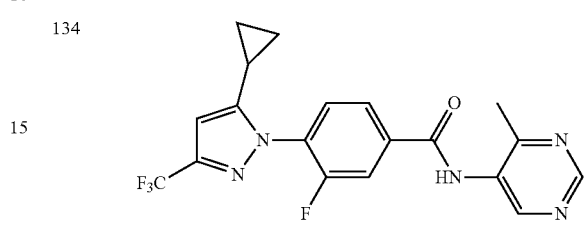 |
| 135 | 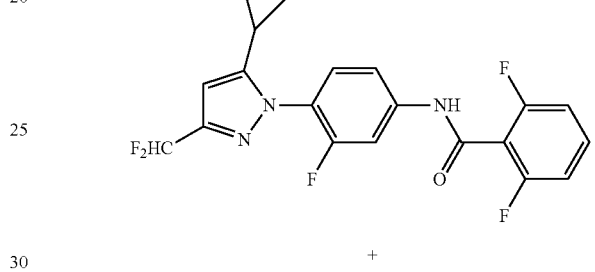 |
| | 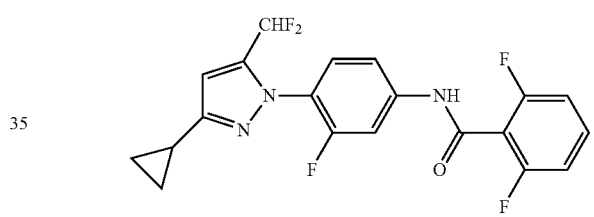 |

The compounds of the present invention (e.g., compounds of formulas I, IA, IA-I, and/or IA-III including their pharmaceutically acceptable esters and salts) are useful for the treatment, prevention, inhibition, and/or amelioration of diseases and disorders associated with calcium release-activated calcium (CRAC) channel.

Another embodiment of the present invention is a method for treating a disease or disorder via modulation of CRAC channels by administering to a patient in need of such treatment an effective amount of a compound of the present invention (e.g., a compound of formula I, IA, IA-I, and/or IA-III as defined above).

Yet another embodiment of the present invention is a method for treating a disease or disorder via modulation of CRAC channels by administering to a patient in need of such treatment an effective amount of a compound of the present invention (e.g., a compound of formula I, IA, IA-I, and/or IA-III as defined above), in combination (simultaneously or sequentially) with at least one other anti-inflammatory agent.

The compounds of the present invention may inhibit store operated calcium entry, interrupt the assembly of SOCE units, alter the functional interactions of proteins that form store operated calcium channel complexes, and alter the functional interactions of STIM1 with Orai1. These compounds are SOC channel pore blockers, and are CRAC channel pore blockers.

The compounds described herein modulate intracellular calcium and are used in the treatment of diseases, disorders or conditions where modulation of intracellular calcium has a beneficial effect. In one embodiment, the compounds described herein inhibit store operated calcium entry. In one embodiment, the compounds of the present invention capable of modulating intracellular calcium levels interrupt the assembly of SOCE units. In another embodiment, the compounds of the present invention capable of modulating intracellular calcium levels alter the functional interactions of proteins that form store operated calcium channel complexes. In one embodiment, the compounds of the present invention capable of modulating intracellular calcium levels alter the functional interactions of STIM1 with Orai1. In other embodiments, the compounds of the present invention capable of modulating intracellular calcium levels are SOC channel pore blockers. In other embodiments, the compounds of the present invention capable of modulating intracellular calcium levels are CRAC channel pore blockers.

In one aspect, the compounds of the present invention capable of modulating intracellular calcium levels inhibit the electrophysiological current ($I_{SOC}$) directly associated with activated SOC channels. In one aspect, compounds capable of modulating intracellular calcium levels inhibit the electrophysiological current ($I_{CRAC}$) directly associated with activated CRAC channels.

The compounds of the present invention are useful in the treatment of diseases, conditions or disorders that benefit from modulation of intracellular calcium, including, but not limited to, an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, hepatic diseases or disorders, and renal diseases or disorders. In one embodiment, the compounds described herein are used as immunosuppresants to prevent (or inhibit) transplant graft rejections, allogeneic or xenogeneic transplantation rejection (organ, bone marrow, stem cells, other cells and tissues), and/or graft-versus—host disease. For instance, the compounds of the present invention can be used to prevent (or inhibit) transplant graft rejections result from tissue or organ transplants. The compounds of the present invention can also be used to prevent (or inhibit) graft-versus-host disease resulting from bone marrow or stem cell transplantation.

More particularly, the compounds of formula I, IA, IA-I, and/or IA-III are useful in the treatment of a variety of inflammatory diseases including, but not limited to, inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma and Sjogren's syndrome The compounds described herein modulate an activity of, modulate an interaction of, or bind to, or interact with at least one portion of a protein in the store operated calcium channel complex. In one embodiment, the compounds described herein modulate an activity of, modulate an interaction of, or bind to, or interact with at least one portion of a protein in the calcium release activated calcium channel complex. In one embodiment, the compounds described herein reduce the level of functional store operated calcium channel complexes. In another embodiment, the compounds described herein reduce the level of activated store operated calcium channel complexes. In a further embodiment, the store operated calcium channel complexes are calcium release activated calcium channel complexes.

The compounds of the present invention which are capable of modulating intracellular calcium levels for treatment of a disease or disorder, when administered to a subject having a disease or disorder, effectively reduce, ameliorate or eliminate a symptom or manifestation of the disease, condition or disorder. In other embodiments, the compounds described herein are administered to a subject predisposed to a disease, condition or disorder that does not yet manifest a symptom of the disease, condition or disorder, and prevents or delays development of the symptoms. In further embodiments, the compound of the present invention has such effects alone or in combination with other agents, or functions to enhance a therapeutic effect of another agent.

Due to the key role of calcium in the regulation of cellular proliferation in general, calcium channel inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention, as modulators of apoptosis, are useful in the treatment of cancer (including, but not limited to, those types mentioned herein above), viral infections (including, but not limited to herpevirus, poxvirus, Epstein-Barr virus, Sindbis virus and adenovirus), prevention of AIDS development in HIV-infected individuals, autoimmune diseases (including, but not limited, to systemic lupus, erythematosus, autoimmune mediated glomerulonephritis, rheumatoid arthritis, psoriasis, inflammatory bowel disease, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including, but not limited to, osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. These agents are therefore useful in the treatment of viral infections (including, but not limited to, HIV, human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds are also useful in inhibiting tumor angiogenesis and metastasis.

The compounds of the present invention are also useful in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example, ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well.

The invention further provides a pharmaceutical composition comprising one or more compounds of formula I, IA, IA-I, and/or IA-III and a pharmaceutically acceptable carrier.

Yet another embodiment of the invention is a dosage form comprising one or more compounds of the present invention, optionally with a pharmaceutically acceptable carrier. The dosage form can be, for example, a solid oral dosage form such as a tablet or capsule.

DETAIL DESCRIPTION OF THE INVENTION

Unless defined otherwise, all technical and scientific terms used herein have the same meaning as is commonly understood in the field to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry and molecular biology terms are found in reference works, including but not limited to, Carey and Sundberg "ADVANCED ORGANIC CHEMISTRY $4^{th}$ edition" Vols. A (2000) and B (2001), Plenum Press, New York and "MOLECULAR BIOLOGY OF THE CELL $5^{th}$ edition" (2007), Garland Science, New York. Unless otherwise indicated, conventional methods of mass spectroscopy, NMR, HPLC, protein chemistry, biochemistry, recombinant DNA techniques and pharmacology, are contemplated within the scope of the embodiments disclosed herein.

Unless specific definitions are provided, the nomenclature employed in connection with, and the laboratory procedures and techniques of, analytical chemistry, and medicinal and pharmaceutical chemistry described herein are those generally used. In some embodiments, standard techniques are used for chemical analyses, pharmaceutical preparation, formulation, and delivery, and treatment of patients. In other embodiments, standard techniques are used for recombinant DNA, oligonucleotide synthesis, and tissue culture and transformation (e.g., electroporation, lipofection). In finer embodiments, reactions and purification techniques are performed e.g., using kits of manufacturer's specifications or as described herein. The foregoing techniques and procedures are generally performed by conventional methods and as described in various general and more specific references that are cited and discussed throughout the present specification.

As used herein the following definitions shall apply unless otherwise indicated. Further many of the groups defined herein can be optionally substituted. The listing of substituents in the definition is exemplary and is not to be construed to limit the substituents defined elsewhere in the specification.

The term 'alkyl' refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term substituted or unsubstituted ($C_{1-6}$) alkyl refers to an alkyl group as defined above having up to 6 carbon atoms.

The term "alkenyl" refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl.

The term substituted or unsubstituted ($C_{1-6}$)alkenyl refers to an alkeynl group as defined above having up to 6 carbon atoms.

The term "alkynyl" refers to a straight or branched chain hydrocarbyl radical having at least one carbon-carbon triple bond, and having in the range of about 2 up to 12 carbon atoms (with radicals having in the range of about 2 to 10 carbon atoms presently being preferred) e.g., ethynyl, propynyl, and butnyl.

The term substituted or unsubstituted ($C_{1-6}$) alkynyl refers to an alkynyl group as defined above having up to 6 carbon atoms.

The term "alkoxy" denotes an alkyl group as defined above attached via an oxygen linkage to the rest of the molecule. Representative examples of those groups are $—OCH_3$ and $—OC_2H_5$.

The term "cycloalkyl" denotes a non-aromatic mono or multicyclic ring system of about 3 to 12 carbon atoms such as cyclopropyl, cyclobutyl, cyclopentyl, and cyclohexyl. Non-limiting examples of multicyclic cycloalkyl groups include perhydronapththyl, adamantly, norbornyl groups (bridged cyclic group), or spirobicyclic groups e.g. spiro (4,4) non-2-yl.

The term "cycloalkylalkyl" refers to a cyclic ring-containing radical containing in the range of about 3 up to 8 carbon atoms directly attached to an alkyl group which is then attached to the main structure at any carbon in the alkyl group that results in the creation of a stable structure such as cyclopropylmethyl, cyclobuyylethyl, and cyclopentylethyl.

The term "cycloalkenyl" refers to a cyclic ring-containing radical containing in the range of about 3 up to 8 carbon atoms with at least one carbon-carbon double bond such as cyclopropenyl, cyclobutenyl, and cyclopentenyl.

The term "aryl" refers to an aromatic radical having in the range of 6 up to 20 carbon atoms such as phenyl, naphthyl, tetrahydronapthyl, indanyl, and biphenyl.

The term "arylalkyl" refers to an aryl group as defined above directly bonded to an alkyl group as defined above, e.g., —CH$_2$C$_6$H$_5$, and —C$_2$H$_5$C$_6$H$_5$.

The term "heterocyclic ring" refers to a non-aromatic 3 to 15 member ring radical which, consists of carbon atoms and at least one heteroatom selected from the group consisting of nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heteroaryl" refers to an optionally substituted 5-14 member aromatic ring having one or more heteroatoms selected from N, O, and S as ring atoms. The heteroaryl may be a mono-, bi- or tricyclic ring system. Examples of such heteroaryl ring radicals includes but are not limited to oxazolyl, thiazolyl imidazolyl, pyrrolyl, furanyl, pyridinyl, pyrimidinyl, pyrazinyl, benzofuranyl, indolyl, benzothiazolyl, benzoxazolyl, carbazolyl, quinolyl and isoquinolyl. The heteroaryl ring radical may be attached to the main structure at any heteroatom or carbon atom that results in the creation of a stable structure.

Examples of such "heterocyclic ring" or "heteroaryl" radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl oxadiazolyl, chromanyl, isochromanyl and the like.

The term "heteroarylalkyl" refers to a heteroaryl ring radical as defined above directly bonded to an alkyl group. The heteroarylalkyl radical may be attached to the main structure at any carbon atom from the alkyl group that results in the creation of a stable structure.

The term "heterocyclylalkyl" refers to a heterocyclic ring radical as defined above directly bonded to an alkyl group. The heterocyclylalkyl radical may be attached to the main structure at carbon atom in the alkyl group that results in the creation of a stable structure.

The term "substituted" unless otherwise specified refers to substitution with any one or any combination of the following substituents: hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted aryl, substituted or unsubstituted heteroaryl, substituted heterocyclylalkyl ring, substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)NR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$ NR$^x$R$^y$—, —OR$^x$, —OR$^x$C(O)NR$^y$R$^z$, —OR$^x$C(O) OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, substituted or unsubstituted heterocyclic ring, or any two of R$^x$, R$^y$ and R$^z$ may be joined to form a substituted or unsubstituted saturated or unsaturated 3-10 member ring, which may optionally include heteroatoms which may be same or different and are selected from O, NR$^x$ or S. The substituents in the aforementioned "substituted" groups cannot be further substituted. For example, when the substituent on "substituted alkyl" is "substituted aryl", the substituent on "substituted aryl" cannot be "substituted alkenyl". Substitution or the combination of substituents envisioned by this invention are preferably those resulting in the formation of a stable compound.

The term "halogen" or "halo" refers to radicals of fluorine, chlorine, bromine and iodine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —CH$_2$CH$_2$SO$_2$Ph, cyanoethyl, 2-(trimethylsilyl) ethyl, 2-(trimethyl silyl)ethoxymethyl, 2-toluenesulfonyl) ethyl, 2-(p-nitrophenylsulfenyl)ethyl, 2-dipheny-1-phosphino)-ethyl and nitroethyl. For a general description of protecting groups and their use, see T. W. Greene, Protective Groups in Organic Synthesis, John Wiley & Sons, New York, 1991.

The term "stereoisomer" refers to compounds, which have identical chemical composition, but differ with regard to arrangement of the atoms and the groups in space. These include enantiomers, diastereomers, geometrical isomers, atropisomer or conformational isomers.

All the stereoisomers of compounds described herein are within the scope of this invention. Racemic mixtures are also encompassed within the scope of this invention. Therefore, single stereochemical isomers as well enantiomeric, diastereoisomeric and geometric (or conformational) mixtures of the present compounds fall within the scope of the invention.

The term "tautomers" refers to compounds, which are characterized by relatively easy interconversion of isomeric forms in equilibrium. These isomers are intended to be covered by this invention.

The term "prodrug" refers to compounds, which are an inactive precursor of a compound, converted into its active form in the body by normal metabolic processes.

The term "ester" refers to compounds, which are formed by reaction between an acid and an alcohol with elimination of water. An ester can be represented by the formula RCOOR', where R is the base compound and R' is the ester moiety (e.g., an ethyl group).

Additionally the instant invention also includes the compounds which differ only in the presence of one or more isotopically enriched atoms for example replacement of hydrogen with deuterium and the like.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides or alkyl sulphates such as MeI and $(Me)_2SO_4$; non-natural amino acids such as D-isomers or substituted amino acids; guanidine or substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, and swine; domestic animals such as rabbits, dogs, and cats; and laboratory animals including rodents, such as rats, mice and guinea pigs. Examples of non-mammals include, but are not limited to, birds, and fish. In one embodiment of the methods and compositions provided herein, the mammal is a human.

The terms "treat," "treating" or "treatment," as used herein, include alleviating, abating or ameliorating a disease, disorder or condition symptoms, preventing additional symptoms, ameliorating or preventing the underlying causes of symptoms, inhibiting the disease, disorder or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition either prophylactically and/or therapeutically.

As used herein, the term "target protein" refers to a protein or a portion of a protein capable of being bound by, or interacting with a compound described herein, such as a compound capable of modulating a STIM protein and/or an Orai protein. In certain embodiments, a target protein is a STIM protein. In other embodiments, a target protein is an Orai protein, and in yet other embodiments, the compound targets both STIM and Orai proteins.

The term "STIM protein" refers to any protein situated in the endoplasmic reticular or plasma membrane which activates an increase in rate of calcium flow into a cell by a CRAC channel. (STIM refers to a stromal interaction molecule.) As used herein, "STIM protein" includes but is not limited to, mammalian STIM-1, such as human and rodent (e.g., mouse) STIM-1, *Drosophila melanogaster* D-STIM, *C. elegans* C-STIM, *Anopheles gambiae* STIM and mammalian STIM-2, such as human and rodent (e.g., mouse) STIM-2. As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

It will be appreciated by "activate" or "activation" it is meant the capacity of a STIM protein to up-regulate, stimulate, enhance or otherwise facilitate calcium flow into a cell by a CRAC channel. It is envisaged that cross-talk between the STIM protein and the CRAC channel may occur by either a direct or indirect molecular interaction. Suitably, the STIM protein is a transmembrane protein which is associated with, or in close proximity to, a CRAC channel.

The term "fragment" or "derivative" when referring to a protein (e.g. STIM, Orai) means proteins or polypeptides which retain essentially the same biological function or activity in at least one assay as the native protein(s). For example, the fragment or derivative of the referenced protein preferably maintains at least about 50% of the activity of the native protein, at least 75%, or at least about 95% of the activity of the native protein, as determined, e.g., by a calcium influx assay.

As used herein, "amelioration" refers to an improvement in a disease or condition or at least a partial relief of symptoms associated with a disease or condition. As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that are attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target (e.g., a target protein). For example, in some embodiments, a modulator causes an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

As used herein, "modulation" with reference to intracellular calcium refers to any alteration or adjustment in intracellular calcium including but not limited to alteration of calcium concentration in the cytoplasm and/or intracellular calcium storage organelles, e.g., endoplasmic reticulum, or alteration of the kinetics of calcium fluxes into, out of and within cells. In aspect, modulation refers to reduction.

The terms "inhibits", "inhibiting", or "inhibitor" of SOC channel activity or CRAC channel activity, as used herein, refer to inhibition of store operated calcium channel activity or calcium release activated calcium channel activity.

The term "acceptable" with respect to a formulation, composition or ingredient, as used herein, means having no persistent detrimental effect on the general health of the subject being treated.

The term "pharmaceutically acceptable," molecular entities and compositions that are physiologically tolerable and do not typically produce an allergic or similar untoward reaction, such as gastric upset, and dizziness, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

The term "pharmaceutical composition" refers to a mixture of a compound of the present invention with other chemical components, such as carriers, stabilizers, diluents, dispersing agents, suspending agents, thickening agents, and/or excipients.

The compounds and pharmaceutical compositions of the present invention can be administered by various routes of administration including, but not limited to, intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result is reduction and/or alleviation of the signs, symptoms, or causes of a disease, or any other desired alteration of a biological system. For example, an "effective amount" for therapeutic uses is the amount of a compound of the present invention required to provide a clinically significant decrease in disease symptoms. In some embodiments, an appropriate "effective" amount in any individual case is determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. In some embodiments, diluents are used to stabilize compounds because they provide a more stable environment. Salts dissolved in buffered solutions (which also provide pH control or maintenance) are utilized as diluents, including, but not limited to a phosphate buffered saline solution.

As used herein, "intracellular calcium" refers to calcium located in a cell without specification of a particular cellular location. In contrast, "cytosolic" or "cytoplasmic" with reference to calcium refers to calcium located in the cell cytoplasm.

As used herein, an effect on intracellular calcium is any alteration of any aspect of intracellular calcium, including but not limited to, an alteration in intracellular calcium levels and location and movement of calcium into, out of or within a cell or intracellular calcium store or organelle. For example, in some embodiments, an effect on intracellular calcium is an alteration of the properties, such as, for example, the kinetics, sensitivities, rate, amplitude, and electrophysiological characteristics, of calcium flux or movement that occurs in a cell or portion thereof. In some embodiments, an effect on intracellular calcium is an alteration in any intracellular calcium-modulating process, including, store-operated calcium entry, cytosolic calcium buffering, and calcium levels in or movement of calcium into, out of or within an intracellular calcium store. Any of these aspects are assessed in a variety of ways including, but not limited to, evaluation of calcium or other ion (particularly cation) levels, movement of calcium or other ion (particularly cation), fluctuations in calcium or other ion (particularly cation) levels, kinetics of calcium or other ion (particularly cation) fluxes and/or transport of calcium or other ion (particularly cation) through a membrane. An alteration is any such change that is statistically significant. Thus, for example, in some embodiments, if intracellular calcium in a test cell and a control cell is said to differ, such differences are a statistically significant difference.

Modulation of intracellular calcium is any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In some embodiments, intracellular calcium modulation involves alteration or adjustment, e.g. reduction or inhibition, of store-operated calcium entry, cytosolic calcium buffering, calcium levels in or movement of calcium into, out of or within an intracellular calcium store or organelle, and/or basal or resting cytosolic calcium levels. The modulation of intracellular calcium involves an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

As used herein, "involved in", with respect to the relationship between a protein and an aspect of intracellular calcium or intracellular calcium regulation means that when expression or activity of the protein in a cell is reduced, altered or eliminated, there is a concomitant or associated reduction, alteration or elimination of one or more aspects of intracellular calcium or intracellular calcium regulation. Such an alteration or reduction in expression or activity occurs by virtue of an alteration of expression of a gene encoding the protein or by altering the levels of the protein. A protein involved in an aspect of intracellular calcium, such as, for example, store-operated calcium entry, thus, are one that provides for or participates in an aspect of intracellular calcium or intracellular calcium regulation. For example, a protein that provides for store-operated calcium entry are a STIM protein and/or an Orai protein.

As used herein, a protein that is a component of a calcium channel is a protein that participates in multi-protein complex that forms the channel.

As used herein, "cation entry" or "calcium entry" into a cell refers to entry of cations, such as calcium, into an intracellular location, such as the cytoplasm of a cell or into the lumen of an intracellular organelle or storage site. Thus, in some embodiments, cation entry is, for example, the movement of cations into the cell cytoplasm from the extracellular medium or from an intracellular organelle or storage site, or the movement of cations into an intracellular organelle or storage site from the cytoplasm or extracellular medium. Movement of calcium into the cytoplasm from an intracellular organelle or storage site is also referred to as "calcium release" from the organelle or storage site.

As used herein, "cell response" refers to any cellular response that results from ion movement into or out of a cell or within a cell. In some embodiments, the cell response is associated with any cellular activity that is dependent, at least in part, on ions such as, for example, calcium. Such activities optionally include, for example, cellular activation, gene expression, endocytosis, exocytosis, cellular trafficking and apoptotic cell death.

As used herein, "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" or "cytokines" refers to small soluble proteins secreted by cells that in some embodiments, alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1.alpha., IL-1.beta., and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-.alpha., TNF-.beta., LT-.beta., CD40 ligand, Fas ligand, CD27 ligand, CD30 ligand, 4-1BBL, Trail), and MIF.

"Store operated calcium entry" or "SOCE" refers to the mechanism by which release of calcium ions from intracellular stores is coordinated with ion influx across the plasma membrane.

Cellular calcium homeostasis is a result of the summation of regulatory systems involved in the control of intracellular calcium levels and movements. Cellular calcium homeostasis is achieved, at least in part, by calcium binding and by movement of calcium into and out of the cell across the plasma membrane and within the cell by movement of calcium across membranes of intracellular organelles including, for example, the endoplasmic reticulum, sarcoplasmic reticulum, mitochondria and endocytic organelles including endosomes and lysosomes.

Movement of calcium across cellular membranes is carried out by specialized proteins. For example, calcium from the extracellular space enters the cell through various calcium channels and a sodium/calcium exchanger and is actively extruded from the cell by calcium pumps and sodium/calcium exchangers. Calcium is also released from internal stores through inositol trisphosphate or ryanodine receptors and is likely taken up by these organelles by means of calcium pumps.

Calcium enters cells by any of several general classes of channels, including but not limited to, voltage-operated calcium (VOC) channels, store-operated calcium (SOC) channels, and sodium/calcium exchangers operating in reverse mode. VOC channels are activated by membrane depolarization and are found in excitable cells like nerve and muscle and are for the most part not found in nonexcitable cells. Under some conditions, $Ca^{2+}$ also enters cells via $Na^+$—$Ca^{2+}$ exchangers operating in reverse mode.

Endocytosis provides another process by which cells take up calcium from the extracellular medium through endosomes. In addition, some cells, e.g., exocrine cells, release calcium via exocytosis.

Cytosolic calcium concentration is tightly regulated with resting levels usually estimated at approximately 0.1 .mu.M in mammalian cells, whereas the extracellular calcium concentration is typically about 2 mM. This tight regulation facilitates transduction of signals into and within cells through transient calcium flux across the plasma membrane and membranes of intracellular organelles. There is a multiplicity of intracellular calcium transport and buffer systems in cells that serve to shape intracellular calcium signals and maintain the low resting cytoplasmic calcium concentration. In cells at rest, the principal components involved in maintaining basal calcium levels are calcium pumps and leaks in the endoplasmic reticulum and plasma membrane. Disturbance of resting cytosolic calcium levels effects transmission of such signals and give rise to defects in a number of cellular processes. For example, cell proliferation involves a prolonged calcium signalling sequence. Other cellular processes include, but are not limited to, secretion, signalling, and fertilization, involve calcium signalling.

Cell-surface receptors that activate phospholipase C(PLC) create cytosolic $Ca^{2+}$ signals from intra- and extracellular sources. An initial transient rise of $[Ca^{2+}]i$ (intracellular calcium concentration) results from the release of $Ca^{2+}$ from the endoplasmic reticulum (ER), which is triggered by the PLC product, inositol-1,4,5-trisphosphate ($P_3$), opening $IP_3$ receptors in the ER (Streb et al. Nature, 306, 67-69, 1983). A subsequent phase of sustained $Ca^{2+}$ entry across the plasma membrane then ensues, through specialized store operated calcium (SOC) channels (in the case of immune cells the SOC channels are calcium release-activated calcium (CRAC) channels) in the plasma membrane. Store-operated $Ca^{2+}$ entry (SOCE) is the process in which the emptying of $Ca^{2+}$ stores itself activates $Ca^{2+}$ channels in the plasma membrane to help refill the stores (Putney, Cell Calcium, 7, 1-12, 1986; Parekh et al, Physiol. Rev. 757-810; 2005). SOCE does more than simply provide $Ca^{2+}$ for refilling stores, but itself generates sustained $Ca^{2+}$ signals that control such essential functions as gene expression, cell metabolism and exocytosis (Parekh and Putney, Physiol. Rev. 85, 757-810 (2005).

In lymphocytes and mast cells, activation of antigen or Fc receptors causes the release of $Ca^{2+}$ from intracellular stores, which in turn leads to $Ca^{2+}$ influx through CRAC channels in the plasma membrane. The subsequent rise in intracellular $Ca^{2+}$ activates calcineurin, a phosphatase that regulates the transcription factor NFAT. In resting cells, NFAT is phosphorylated and resides in the cytoplasm, but when dephosphorylated by calcineurin, NFAT translocates to the nucleus and activates different genetic programmes depending on stimulation conditions and cell type. In response to infections and during transplant rejection, NFAT partners with the transcription factor AP-1 (Fos-Jun) in the nucleus of "effector" T cells, thereby transactivating cytokine genes, genes that regulate T cell proliferation and other genes that orchestrate an active immune response (Rao et al., Annu Rev Immunol, 1997; 15:707-47). In contrast, in T cells recognizing self antigens, NFAT is activated in the absence of AP-1, and activates a transcriptional programme otherwise known as "anergy" that suppresses autoimmune responses (Macian et al., Transcriptional mechanisms underlying lymphocyte tolerance. Cell, 2002 Jun. 14; 109(6):719-31). In a subclass of T cells, known as regulatory T cells which suppress autoimmunity mediated by self-reactive effector T cells, NFAT partners with the transcription factor FOXP3 to activate genes responsible for suppressor function (Wu et al., Cell, 2006 Jul. 28; 126(2):375-87; Rudensky A Y, Gavin M, Zheng Y. Cell. 2006 Jul. 28; 126(2):253-256).

The endoplasmic reticulum (ER) carries out a variety processes. The ER has a role as both an agonist-sensitive $Ca^{2+}$ store and sink, protein folding/processing takes place within its lumen. Here, numerous $Ca^{2+}$-dependent chaperone proteins ensure that newly synthesized proteins are folded correctly and sent off to the appropriate destination. The ER is also involved in vesicle trafficking, release of stress signals, regulation of cholesterol metabolism, and apoptosis. Many of these processes require intraluminal $Ca^{2+}$, and protein misfolding, ER stress responses, and apoptosis are all likely induced by depleting the ER of $Ca^{2+}$ for prolonged periods of time. Because of its role as a source of $Ca^{2+}$, it is clear that ER $Ca^{2+}$ content must fall after stimulation. However, to preserve the functional integrity of the ER, it is vital that the $Ca^{2+}$ content does not fall too low or is maintained at a low level. Replenishment of the ER with $Ca^{2+}$ is therefore a central process to all eukaryotic cells. Because a fall in ER $Ca^{2+}$ content activates store-operated $Ca^{2+}$ channels in the plasma membrane, a major function of this $Ca^{2+}$ entry pathway is believed to be maintenance of ER $Ca^{2+}$ levels that are necessary for proper protein synthesis and folding. However, store-operated $Ca^{2+}$ channels have other important roles.

The understanding of store operated calcium entry was provided by electrophysiological studies which established that the process of emptying the stores activated a $Ca^{2+}$ current in mast cells called $Ca^{2+}$ release-activated $Ca^{2+}$ current or $I_{CRAC}$. $I_{CRAC}$ is non-voltage activated, inwardly rectifying, and remarkably selective for $Ca^{2+}$. It is found in several cell types mainly of hemopoietic origin. $I_{CRAC}$ is not the only store-operated current, and it is now apparent that store-operated influx encompasses a family of $Ca^{2+}$-permeable channels, with different properties in different cell types. $I_{CRAC}$ was the first store-operated $Ca^{2+}$ current to be described and remains a popular model for studying store-operated influx.

Effects of compounds or agents on intracellular calcium can be monitored using various screening/identification methods which provide for a direct or indirect evaluation or measurement of cellular (including cytosolic and intracellular organelle or compartment) calcium and/or movement of ions into, within or out of a cell, organelle, calcium store or portions thereof (e.g., a membrane). A variety of methods can be used for evaluating calcium levels and ion movements or flux. The particular method used and the conditions employed would depend on whether a particular aspect of intracellular calcium is being monitored or assessed. For example, in some aspects, reagents and conditions may be used for specifically evaluating store-operated calcium entry, resting cytosolic calcium levels, calcium buffering and calcium levels and uptake by or release from intracellular organelles and calcium stores. Alternately, the effect of a compound or agent on intracellular calcium can be monitored or assessed using, for example, a cell, an intracellular organelle or calcium storage compartment, a membrane (including, e.g., a detached membrane patch or a lipid bilayer) or a cell-free assay system (e.g., outside-out membrane vesicle). Generally, some aspect of intracellular calcium is monitored or assessed in the presence of test agent and compared to a control, e.g., intracellular calcium in the absence of test agent.

Diseases, Disorders or Conditions

Clinical studies demonstrate that the CRAC channel is absolutely required for the activation of genes underlying the T cell response to antigen. Sustained calcium entry is needed for lymphocyte activation and adaptive immune response. Calcium entry into lymphocytes occurs primarily through the CRAC channels. Increased calcium leads to NFAT activation and expression of cytokines required for immune response. Inhibiting the store operated calcium entry is an efficient way to prevent T cell activation.

Inhibition of CRAC channel activity with the compounds that modulate intracellular calcium levels provide a means for providing immunosuppressive therapy as demonstrated by the elimination of store-operated calcium entry noted in patients with severe-combined immunodeficiency (SCID). T cells, fibroblasts, and in some cases B cells, from patients with T cell immunodeficiency or SCID having a principal defect in T cell activation show a strong defect in store-operated calcium entry. SCID patients lack adaptive immune response, but without any impairment or toxicity in major organs. The SCID patient phenotype indicates that inhibition of CRAC channels is an effective strategy for immunosuppression.

Diseases/Disorders Involving Inflammation and Diseases/Disorders Related to the Immune System In some embodiments, diseases, disorders or conditions that are treated or prevented using compounds disclosed herein that are capable of modulating intracellular calcium levels, compositions thereof, and methods provided herein to identify compounds capable of modulating intracellular calcium levels, include diseases, conditions or disorders involving inflammation and/or that are related to the immune system. These diseases include, but are not limited to, asthma, chronic obstructive pulmonary disease, rheumatoid arthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration. Store-operated calcium influx in particular is thought to play an important role in PMN activation. It has been shown that trauma increases PMN store-operated calcium influx and that prolonged elevations of cytosolic calcium concentration due to enhanced store-operated calcium influx likely alters stimulus-response coupling to chemotaxins and contribute to PMN dysfunction after injury. Modulation of PMN cytosolic calcium concentration through store-operated calcium channels might therefore be useful in regulating PMN-mediated inflammation and spare cardiovascular function after injury, shock or sepsis.

Calcium plays a critical role in lymphocyte activation. Activation of lymphocytes, e.g., by antigen stimulation, results in rapid increases in intracellular free calcium concentrations and activation of transcription factors, including nuclear factor of activated T cells (NFAT), NF-.kappa.B, JNK1, MEF2 and CREB. NFAT is a key transcriptional regulator of the IL-2 (and other cytokine) genes. A sustained elevation of intracellular calcium level is required to keep NFAT in a transcriptionally active state, and is dependent on store-operated calcium entry. Reduction or blocking of store-operated calcium entry in lymphocytes blocks calcium-dependent lymphocyte activation. Thus, in some embodiments, modulation of a STIM protein and/or an Orai protein, and particularly store-operated calcium entry (e.g., reduction in, elimination of store-operated calcium entry), in lymphocytes is a method for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses. For example, in some embodiments treatment of an autoimmune disease/disorder involves reducing, blocking or eliminating store-operated calcium entry in lymphocytes.

Examples of immune disorders include, for example, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In other embodiments, compounds disclosed herein that are capable of modulating intracellular calcium levels, compositions thereof, and methods provided herein to identify compounds capable of modulating intracellular calcium levels, are used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer. Store-operated calcium entry is thought to play an important role in cell proliferation in cancer cells.

Inhibition of SOCE is sufficient to prevent tumor cell proliferation. The pyrazole derivative BTP-2, a direct $I_{CRAC}$ blocker inhibits SOCE and proliferation in Jurkat cells and in colon cancer cells. Moreover, sustained SOCE requires mitochondrial $Ca^{2+}$ uptake and that prevention of mitochondrial $Ca^{2+}$ uptake leads to SOCE inhibition. Stimulation of Jurkat cells induces sustained SOCE and activation of the $Ca^{2+}$-dependent phosphatase calcineurin that dephosphorylates NFAT, promoting expression of interleukin-2 and proliferation. In other embodiments, compounds capable of modulating intracellular calcium levels inhibit SOCE and are used in the treatment of cancer or other proliferative diseases or conditions.

In some embodiments, diseases, disorders or conditions that are treated or prevented using compounds disclosed herein that are capable of modulating intracellular calcium levels, compositions thereof, and methods provided herein to identify compounds capable of modulating intracellular calcium levels, include, for example, hepatic or liver diseases and disorders. These diseases, conditions or disorders include but are not limited to liver injury, for example, due to transplantation, hepatitis and cirrhosis.

Store-operated calcium entry has been implicated in chronic liver disease as well as transplantation injury after cold preservation-warm deoxygenation.

In some embodiments, diseases, conditions or disorders that are treated or prevented using the compounds disclosed herein that are capable of modulating intracellular calcium levels, compositions thereof, and methods provided herein to identify compounds capable of modulating intracellular calcium levels, include kidney or renal diseases and disorders. Mesangial cell hyperplasia is often a key feature of such diseases and disorders. In other embodiments, such diseases and disorders are caused by immunological or other mechanisms of injury, including IgAN, membranoproliferative glomerulonephritis or lupus nephritis. Imbalances in the control of mesangial cell replication also appear to play a key role in the pathogenesis of progressive renal failure. The turnover of mesangial cells in normal adult kidney is very low with a renewal rate of less than 1%. A prominent feature of glomerular/kidney diseases is mesangial hyperplasia due to elevated proliferation rate or reduced cell loss of mesangial cells. When mesangial cell proliferation is induced without cell loss, for example due to mitogenic stimulation, mesangioproliferative glomerulonephritis does result. Data have indicated that regulators of mesangial cell growth, particularly growth factors, are thought to act by regulating store-operated calcium channels. In yet other embodiments, modulators of store-operated calcium influx aids in the treatment of glomerular diseases by inhibiting mesangial cell proliferation.

In one aspect, compounds described herein modulate intracellular calcium, such as but not limited to, modulation (e.g. reduction or inhibition) of SOC channel activity, such as inhibition of CRAC channel activity (e.g. inhibition of $I_{CRAC}$, inhibition of SOCE), in an immune system cell (e.g., a lymphocyte, white blood cell, T cell, B cell), a fibroblast (or a cell derived from a fibroblast), or an epidermal, dermal or skin cell (e.g., a keratinocyte). In some embodiments, the step of modulating one or more proteins involved in modulating intracellular calcium (e.g. a STIM protein and/or Orai protein) involves, for example, reducing the level, expression of, an activity of, function of and/or molecular interactions of a protein. For instance, if a cell exhibits an increase in calcium levels or lack of regulation of an aspect of intracellular calcium modulation, e.g., store-operated calcium entry, then in other embodiments, modulating involves reducing the level of, expression of, an activity or function of, or a molecular interaction of a protein, e.g. a STIM protein and/or Orai protein.

The following general methodology described herein provides the manner and process of making and using the compound of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

General Method of Preparation of Compound of Formula (I)

The compounds of the present invention may be prepared by the following processes. Unless otherwise indicated, all the variables when used in the below formulae are to be understood to present those groups described above in relation to formula (IA). These methods can similarly be applied to other compounds of formula (I) (e.g, I, IA, IA-I, and/or IA-III).

Scheme 1 provides a general process for synthesis of a compound of formula (IA) wherein $L_1$ & $L_2$ together are —NH—CO—, R''' is hydrogen or halogen, and all other variables R, $R^1$, $R^2$, T, U, V, W, A and Cy are as described above in relation to formula (IA)

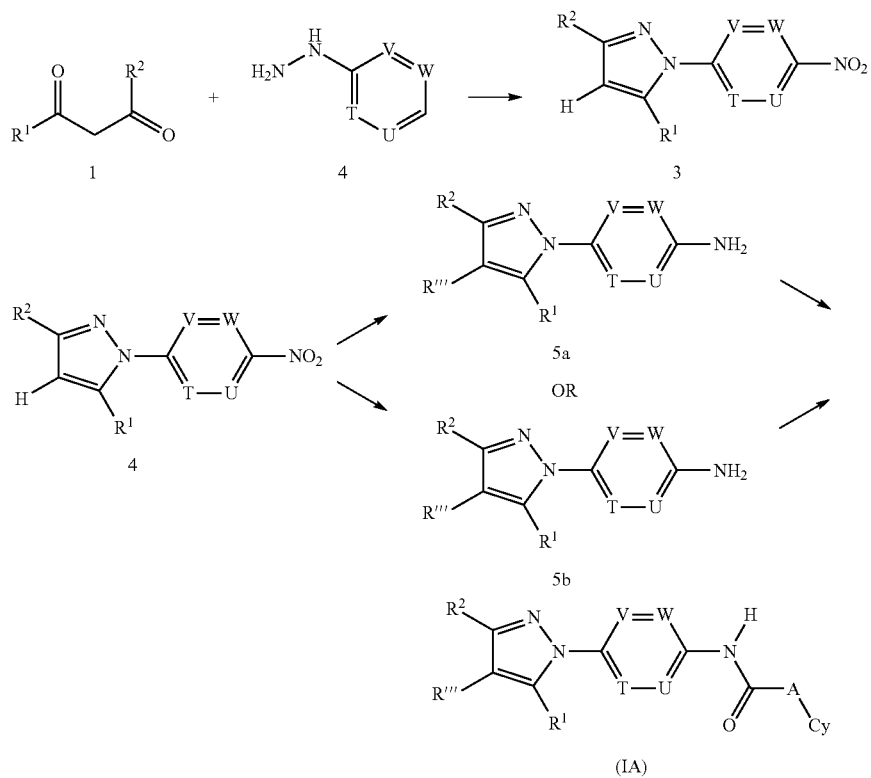

(IA)

A compound of formula 1 can be reacted with a compound of formula 2 (e.g., phenyl hydrazine) to form a compound of formula 3. The compound of formula 3 can then be nitrated, e.g., using a mixture of concentrated $H_2SO_4$ and concentrated $HNO_3$ to form a compound of formula 4. Reduction of the compound of formula 4, such as with $FeCl_3$ and hydrazine in the presence of activated charcoal, yields the corresponding amine compound of formula 5a wherein R''' is Hydrogen. Alternately halogenation followed by reduction of the compound of formula 4, yields the corresponding amine compound of formula 5b wherein R''' is Halogen. The compound of formula 5a or 5b can be coupled with various other intermediates in the presence of a suitable coupling reagent to provide a compound of formula (IA). The compound of formula 5a or 5b can be coupled with i. Cy-A-COOH using one or more amide coupling reagents such as (benzotriazol-1-yloxy)tris(dimethylamino)phosphoniumhexafluoro phosphate (BOP reagent) or N-(3-dimethylaminopropyl)-N'-ethylcarbodiimide hydrochloride (EDC); ii. with acid chlorides of formula Cy-A-COCl; or iii. isocyanates of formula Cy-NCO where A is NH.

Scheme 2 provides a general process for synthesis of a compound of formula (IA) wherein $L_1$ & $L_2$ together i —NH—CO—, R''' is hydrogen or halogen and all other variables R, $R^1$, $R^2$, T, U, V, W, A and Cy are those described above in relation to formula (IA).

Step-1

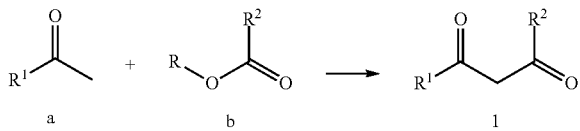

Step-2

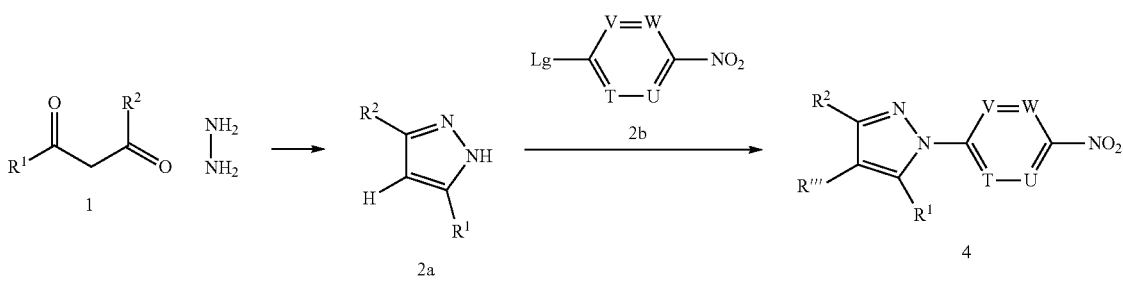

-continued

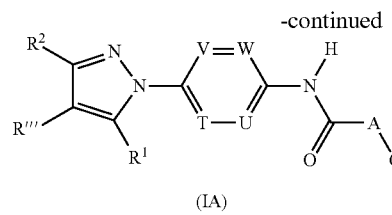

(IA)

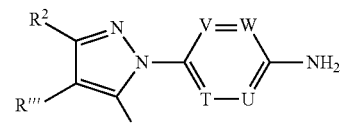

5

Step-1: A ketone of formula a can be condensed with an ester of formula b in the presence of a base such as a metal alkoxide, e.g., sodium ethoxide, to give a diketone of formula 1.

Step-2: The compound of formula 1 can be converted to a pyrazole compound of formula 2a by reacting it with hydrazine. The compound of formula 2a can be reacted with a compound of formula 2b wherein $L_g$ is a leaving group (such as a halogen) in the presence of a suitable base such as an alkali metal carbonate, e.g., $Cs_2CO_3$, to give a compound of formula 4, which can be subjected to a similar sequence of transformations as described above in scheme 1 to afford a compound of formula IA.

Scheme 2A provides a general process for synthesis of a compound of formula (IA) wherein $L_1$ & $L_2$ together is —CO—NH—, R'" is hydrogen or Halogen and all other variables R, $R^1$, $R^2$, T, U, V, W, A and Cy are those described above in relation to formula (IA).

described above in relation to formula I, IA, IA-I, and/or IA-III using suitable intermediates and reagents.

EXPERIMENTAL

The following abbreviations are used throughout this disclosure: EDC.HCl [N-(3-dimethylaminopropyl)-N'-ethylcarbodiimide hydrochloride], HOBt [Hydroxybenzotriazole], TEA (triethylamine), DMF (dimethyl formamide), AcOEt (ethyl acetate), DCM (dichloromethane), DMSO (dimethyl sulfoxide, THF (tetrahydrofuran). Unless otherwise mentioned, work-up implies distribution of reaction mixture between the aqueous and organic phases indicated within parentheses, separation and drying over $Na_2SO_4$ of the organic layer and evaporating the solvent to afford a residue. Unless otherwise stated, purification implies column chromatography using silica gel as the stationary phase and a mixture of petroleum ether (boiling at 60-80° C.) and

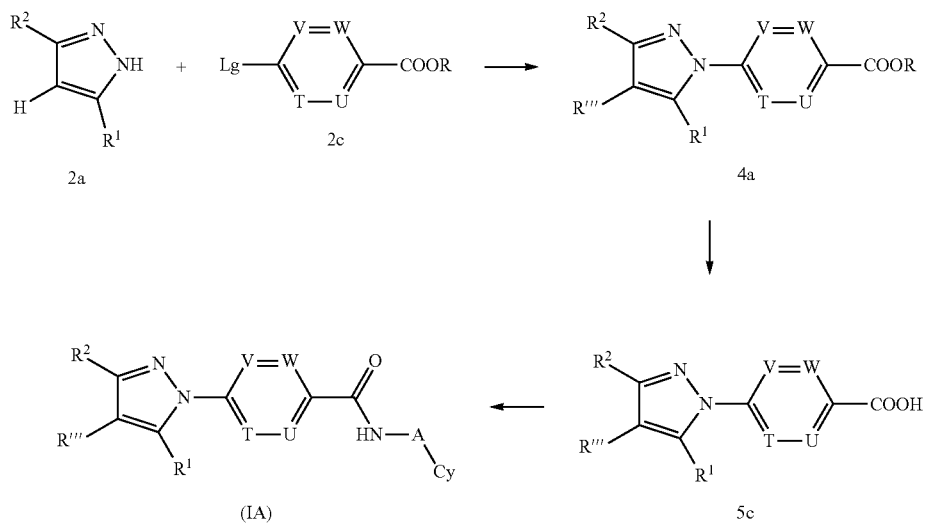

The compound of formula 2a can be reacted with a compound of formula 2c wherein $L_g$ is a leaving group (such as a halogen) in the presence of a suitable base such as an alkali metal carbonate, e.g., $Cs_2CO_3$, to give a compound of formula 4a, which can then be hydrolysed to to give a compound of formula 5c. The compound of formula 5c can be coupled with Cy-A-$NH_2$ using one or more amide coupling reagents such as (benzotriazol-1-yloxy)tris(dimethylamino)phosphoniunhexafluoro phosphate (BOP reagent) or N-(3-dimethylaminopropyl)-N'-ethylcarbodiimide hydrochloride (EDC).

Similar methodologies with certain modifications as known to those skilled in the art can be used to synthesize compounds of formula I, IA, IA-I, and/or IA-III wherein the variables are to be understood to present those groups ethyl acetate or dichloromethane and methanol of suitable polarity as the mobile phases. RT (or rt)implies ambient temperature (~25-28° C.).

Intermediate 1: 1,3-dicyclopropylpropane-1,3-dione

Sodium ethoxide (8 g, 117.64 mmol) was added to a solution of cyclopropyl methyl ketone (5 g, 59.4 mmol) and methyl cyclopropane carboxylate (12 ml, 118.9 mmol) in DMSO (30 mL). The resulting mixture was heated at 60° C. overnight and then cooled to 0° C. After quenching the reaction with 6N HCl, work-up ($H_2O$/AcOEt) gave the title compound as a brown liquid which was used without any purification. $^1$H-NMR (δ ppm, $CDCl_3$, 400 MHz): 16.05 (bs, 0.6H), 5.72 (s, 0.6H) 3.78 (s, 0.8H), 2.08-2.0 (m, 0.8H), 1.62-1.53 (m, 1.2H), 1.12-1.05 (m, 4H), 0.97-0.83 (m, 4H). MS (m/z): 153.2 [M+H]$^+$.

Intermediate 2:
1-cyclopropyl-4,4,4-trifluorobutane-1,3-dione

A procedure similar to that described for intermediate 1 was followed. From cyclopropyl methyl ketone (10 g, 119 mmol), ethyl 2,2,2-trifluoroacetate (29 ml, 237 mmol), DMSO (60 mL) and sodium ethoxide (16.1 g, 237 mmol), the title compound (15 g) was obtained as a brown liquid and was used in the next step without purification. $^1$H-NMR (δ ppm, CDCl$_3$, 400 MHz): 5.65 (s, 2H), 2.16-2.04 (m, 1H), 1.18-1.12 (m, 2H), 0.98-0.94 (m, 2H).

Intermediate 3:
4,4,4-trifluoro-1-(furan-2-yl)butane-1,3-dione

A procedure similar to that described for intermediate 1 was followed. From 1-(furan-2-yl)ethanone (5 g, 45.4 mmol), ethyl 2,2,2-trifluoroacetate (12.9 g, 90.8 mmol), DMSO (30 mL) and sodium ethoxide (6.2 g, 90.8 mmol), the title compound was obtained as a brown liquid quantitatively and was used without purification. $^1$H-NMR (δ ppm, DMSO-d$_6$, 400 M Hz): 9.10 (bs, 1H), 8.15 (s, 1H), 7.96 (d, J 1, 1H), 6.85-6.81 (m, 1H), 6.70 (s, 1H).

Intermediate 4: 3,5-dicyclopropyl-1H-pyrazole

Intermediate 1 (5.3 g, 35 mmol) and hydrazine hydrate (1.8 mL, 38.3 mmol) in ethanol (20 mL) were refluxed overnight. Work-up (H$_2$O/AcOEt) after cooling the mixture to ambient temperature gave the title compound as a brown solid. M.P.: 161-164° C. $^1$H-NMR (δ ppm, CDCl$_3$, 400 MHz): 15.2 (bs, 1H), 5.65 (s, 1H), 2.16-2.09 (m, 2H), 1.18-1.14 (m, 4H), 0.98-0.94 (m, 4H). MS (m/z): 149.04 [M+H]$^+$.

Intermediate 5:
5-cyclopropyl-3-(trifluoromethyl)-1H-pyrazole

Intermediate 2 (0.120 g, 0.66 mmol) and hydrazine hydrate (0.04 mL, 0.72 mmol) were dissolved in ethanol (6 mL) and refluxed overnight. Work-up (H$_2$O/AcOEt) after cooling the mixture to RT gave the title compound as a brown solid (0.114 g).

Intermediate 6: 5-(furan-2-yl)-1-phenyl-3-(trifluoromethyl)-1H-pyrazole

A procedure similar to that described for intermediate 4 was followed. From intermediate 3 (4 g, 19.4 mmol) and phenyl hydrazine (2.31 g, 21.3 mmol), title compound obtained as a white solid. $^1$H-NMR (δ ppm, CDCl$_3$, 400 MHz): 7.52-7.48 (m, 3H), 7.46-7.40 (m, 3H), 6.91 (s, 1H), 6.36-6.33 (m, 1H), 5.96 (d, J 7.4, 1H).

Intermediate 7: 1-phenyl-3-(trifluoromethyl)-1H-pyrazole-5-carboxylic acid

Intermediate 6 (2.84 g, 10.2 mmol) was dissolved in acetone (120 ml) and KMnO$_4$ (11.2 gms, 71.45 mmol in 135 ml water) solution was added to it. This mixture was heated at 60° C. for 3h and then cooled to rt. Then isopropyl alcohol was added to the reaction mixture and stirred at rt overnight. The reaction mixture filtered through celite and filtrate was evaporated on high vacuum. The residue was dissolved in 1N NaOH and washed with petether. Aqueous layer was acidified with 2N HCl solution to obtain the solid. Solid was filtered and dried on high vacuum to obtain the title compound (2.3 g) as a white solid. $^1$H-NMR (δ ppm, CDCl$_3$, 400 MHz): 7.57-7.42 (m, 5H), 7.30 (s, 1H).

Intermediate 8: methyl 1-phenyl-3-(trifluoromethyl)-1H-pyrazole-5-carboxylate

Intermediate 7 (1.55 g, 6.0 mmol) was dissolved in MeOH (15 ml), cooled to 0° C. and thionyl chloride (1.3 ml, 18.2 mmol) was added. Reaction mixture was heated to 60° C. for overnight. Work up (AcOEt: H$_2$O) followed by evaporation on high vacuum obtained the title compound as an yellow solid. $^1$H-NMR (δ ppm, CDCl$_3$, 400 MHz): 7.51-7.47 (m, 3H), 7.46-7.41 (m, 2H), 7.50 (s, 1H), 3.82 (s, 3H).

Intermediate 9:
3,5-dicyclopropyl-1-(4-nitrophenyl)-1H-pyrazole

A solution of intermediate 4 (2.0 g, 13.5 mmol) and Cs$_2$CO$_3$ (5.51 g, 40.5 mmol) in DMSO (15 mL) was heated at 160° C. under nitrogen for 0.5 h. To the mixture, 4-chloro-1-nitro benzene (6.38 g, 40.5 mmol) was added and stirred at the same temperature for 4 h. Work-up (H$_2$O/AcOEt) and purification afforded the title compound (0.8 g). $^1$H-NMR (δ ppm, CDCl$_3$, 400 MHz): 8.32 (d, J 9.0, 2H), 7.92 (d, J 9.0, 2H), 5.76 (s, 1H), 1.97-1.91 (m, 1H), 1.86-1.80 (m, 1H), 1.09-1.04 (m, 2H), 0.98-0.94 (m, 2H), 0.83-0.75 (m, 4H).

Intermediate 10: 3,5-dicyclopropyl-1-(2-fluoro-4-nitrophenyl)-1H-pyrazole

A solution of intermediate 4 (2.0 g, 13.5 mmol) and K$_2$CO$_3$ (5.5 g, 40.6 mmol) in DMSO (20 mL) were heated at 120° C. under nitrogen for 0.5 h. To this mixture, 3,4-difluoro-1-nitrobenzene (2.15 g, 13.5 mmol) was added and stirred at the same temperature for 2 h. Work-up (H$_2$O/AcOEt) and purification afforded the title compound as an yellow solid (3.16 g). $^1$H-NMR (δ ppm, CDCl$_3$, 400 MHz): 8.19-8.12 (m, 2H), 7.78 (t, J 7.9, 1H), 5.70 (s, 1H), 2.10-2.00 (m, 1H), 1.68-1.58 (m, 1H), 1.08-0.92 (m, 4H), 0.82-0.74 (m, 2H), 0.72-0.65 (m, 2H).

Intermediate 11: 2-(3,5-dicyclopropyl-1H-pyrazol-1-yl)-5-nitropyridine

A solution of intermediate 4 (8.0 g, 54.05 mmol) and K$_2$CO$_3$ (27.96 g, 202.6 mmol) in DMSO (60 mL) was heated at 110° C. under nitrogen for 0.5 h. To the mixture, 2-chloro-5-nitro pyridine (12.8 g, 80.75 mmol) was added and stirred at the same temperature for 2 h. Work-up (H$_2$O/AcOEt) and purification afforded the title compound (3.03 g). $^1$H-NMR (δ ppm, CDCl$_3$, 400 MHz): 9.24 (d, J 2.6, 1H), 8.51 (dd, J 2.6, 9.9, 1H), 8.10 (d, J 9.2, 1H), 5.72 (s, 1H), 2.90-2.75 (m, 1H), 1.99-1.90 (m, 1H), 1.06-0.93 (m, 4H), 0.82-0.64 (m, 4H).

Intermediate 12: ethyl 6-(3,5-dicyclopropyl-1H-pyrazol-1-yl)nicotinate

A solution of intermediate 4 (2.0 g, 13.5 mmol) and K$_2$CO$_3$ (5.6 g, 40.5 mmol) in DMSO (15 mL) was heated at 120° C. under nitrogen for 0.5 h. To the mixture, ethyl-6-chloronicotinate (3.8 g, 20.3 mmol) was added and stirred at 160° C. for 4 h. Work-up (H$_2$O/AcOEt) and purification afforded the title compound (0.26 g). $^1$H-NMR ($\delta$ ppm, CDCl$_3$, 400 MHz): 8.95-8.90 (m, 1H), 8.38 (dd, J 2.2, 8.7, 1H), 7.91 (d, J 8.7, 1H), 5.93 (s, 1H), 4.35 (q, J 4.12, 2H), 2.88-2.78 (m, 1H), 1.91-1.83 (m, 1H), 1.33 (t, J 7.1, 3H), 0.99-0.85 (m, 4H), 0.62-0.55 (m, 4H). MS (m/z): 298.3 ([M+H]$^+$).

Intermediate 13: 5-cyclopropyl-1-(4-nitrophenyl)-3-(trifluoromethyl)-1H-pyrazole A procedure similar to that followed for intermediate 9 was employed. From intermediate 5 (1.0 g, 5.67 mmol), Cs$_2$CO$_3$ (5.5 g, 16.9 mmol), DMSO (4 mL) and 4-chloro-1-nitro benzene (1.93 g, 14.1 mmol) was obtained the title compound (0.7 g). $^1$H-NMR ($\delta$ ppm, CDCl$_3$, 400 MHz): 8.38 (d, J 7.08, 2H), 7.92 (d, J 7.08, 2H), 6.32 (s, 1H), 1.89-1.82 (m, 1H), 1.19-1.11 (m, 2H), 0.89-0.85 (m, 2H), MS (m/s): 298.15 [M+H]$^+$.

Intermediate 14: 5-cyclopropyl-1-(2-fluoro-4-nitrophenyl)-3-(trifluoromethyl)-1H-pyrazole A solution of intermediate 5 (6.3 g, 35 mmol) and K$_2$CO$_3$ (14.6 g, 105 mmol) in DMSO (20 mL) was heated at 120° C. under nitrogen for 30 mins. To this mixture, 1,2-difluoro nitrobenzene (5.68 g, 35 mmol) was added and stirred at the same temperature for 2 h. Work-up (H$_2$CO/AcOEt) and purification afforded the title compound (7.52 g). $^1$H-NMR ($\delta$ ppm, DMSO-d$_6$, 400 MHz): 8.49 (dd, J 2.4, 9.9, 1H), 8.47-8.27 (m, 1H), 8.04-8.02 (m, 1H), 6.73 (s, 1H), 1.76-1.68 (m, 1H), 0.99-0.90 (m, 2H), 0.84-0.74 (m, 2H).

Intermediate 15: 5-cyclopropyl-1-(2,6-difluoro-4-nitrophenyl)-3-(trifluoromethyl)-1H-pyrazole Intermediate 5 (1 g, 5.7 mmol) and 3,4,5-trifluoronitrobenzene (1 g 5.7 mmol) were dissolved in THF and added sodium hydride (274 mg, 11.3 mmol). Mixture was refluxed for 2h and reaction mixture cooled to rt and quenched with water. Work-up (H$_2$O/AcOEt) gave the desired product as a yellow gummy liquid. $^1$H-NMR ($\delta$ ppm, CDCl$_3$, 400 MHz): 8.05-8.01 (m, 2H), 6.31 (s, 1H), 1.60-1.50 (m, 1H), 1.00-0.91 (m, 2H), 0.80-0.71 (m, 2H).

Intermediate 16: 2-[5-cyclopropyl-3-(trifluoromethyl)-1H-pyrazol-1-yl]-5-nitropyridine A solution of intermediate 5 (1.0 g, 5.67 mmol) and K$_2$CO$_3$ (2.35 g, 17.03 mmol) in DMSO (10 mL) was heated at 90° C. under nitrogen for 30 mins. To the mixture, 2-chloro-5-nitro pyridine (1.35 g, 8.5 mmol) was added and stirred at the same temperature for 2 h. Work-up (H$_2$O/AcOEt) and purification afforded the title compound (0.30 g). $^1$H-NMR ($\delta$ ppm, CDCl$_3$, 400 MHz): 9.33 (d, J 2.5, 1H), 8.62 (dd, J 2.8, 9.0, 1H), 8.19 (d, J 9.0, 1H), 6.29 (s, 1H), 2.92-2.83 (m, 1H), 1.60-1.50 (m, 2H), 0.79-0.70 (m, 2H).

Intermediate 17: 2-[5-cyclopropyl-3-(trifluoromethyl)-1H-pyrazol-1-yl]-5-nitropyrimidine Intermediate 5 (500 mg, 2.84 mmol) and 2-chloro-4-nitropyrimidine (452 mg, 2.84 mmol) were dissolved in THF and cooled to 0° C. To this mixture sodium hydride (136 mg, 5.7 mmol) was added slowly and reaction mixture was heated to reflux. After one hour reaction mixture cooled to rt and quenched with water. Work up (H$_2$O/AcOEt) and purification gave the desired product (455 mg) as a white solid. $^1$H-NMR ($\delta$ ppm, CDCl$_3$, 400 MHz): 9.58 (s, 2H), 6.37 (s, 1H), 2.82-2.74 (m, 1H), 1.18-1.10 (m, 2H), 0.82-0.75 (m, 2H).

Intermediate 18: methyl 1-(4-nitrophenyl)-3-(trifluoromethyl)-1H-pyrazole-5-carboxylate Intermediate 8 (2 g, 7.4 mmol) was dissolved in acetic acid (15 ml), cooled to 0° C. and added nitration mixture (6 ml HNO$_3$ and 6 ml H$_2$SO$_4$) drop-wise. Reaction mixture was heated to 60° C. for overnight. Work up (AcOEt: H$_2$O) and purification on silicagel (60-120 mesh silicagel) using EA and pet ether (3: 97) as eluent afforded the title compound (850 mg) as a white solid. $^1$H-NMR ($\delta$ ppm, CDCl$_3$, 400 MHz): 8.37 (d, J 9, 2H), 7.68 (d, J 9, 2H), 7.31 (s, 1H), 3.87 (s, 3H).

Intermediate 19: [1-(4-nitrophenyl)-3-(trifluoromethyl)-1H-pyrazol-5-yl]methanol Intermediate 18 (0.662 g, 2.1 mmol) dissolved in a mixture of THF (5 ml) and MeOH (5 ml) and added sodium borohydride (79 mg, 2.1 mmol). Colour of the reaction mixture changed to pink and then two drops of water added to it. Reaction mixture allowed to stir at rt for 1 h and at this stage colour changed to pink to pale yellow. Reaction mixture was allowed to stir further overnight. Work up (AcOEt/H$_2$O) and evaporation of organic layer on vacuum afforded the title compound (558 mg) as a white solid. $^1$H-NMR ($\delta$ ppm, DMSO-d$_6$, 400 MHz): 8.42 (d, J 8.9, 2H), 8.01 (d, J 8.9, 2H), 7.01 (s, 1H), 5.77 (t, J 5.4, 1H), 4.63 (d, J 5.4, 2H).

Intermediate 20: 1-(4-nitrophenyl)-3-(trifluoromethyl)-1H-pyrazole-5-carbaldehyde Oxalyl chloride (0.32 ml, 3.8 mmol) was dissolved in DCM, cooled to −78° C. and added DMSO (0.5 ml 7.6 mmol) and stirred for 30 mins. To this intermediate 19 (550 mg, 1.9 mmol) was added, stirred at −78° C. for 20 mins and added triethyl amine (1.06 ml, 7.6 mmol). Reaction mixture warmed to 0° C. and then slowly heated to rt. Work up (H$_2$O/AcOEt) afforded the title compound (375 mg). 9.85 (s, 1H), 8.41 (d, J 8.6, 2H), 7.99 (d, J 8.5, 2H), 7.84 (s, 1H).

Intermediate 21: 5-(fluoromethyl)-1-(4-nitrophenyl)-3-(trifluoromethyl)-1H-pyrazole Intermediate 19 (0.5 g, 1.75 mmol) was dissolved in DCM (10 ml) and reaction mixture cooled to 0° C. To this (Diethylamino)sulphur trifluoride (0.46 ml, 3.5 mmol) was added drop-wise and allowed the reaction mixture to stir at rt for 30 mins. After completion of the reaction, reaction mixture diluted with DCM and washed with water. DCM removed on rotavapour to obtain the crude. Crude was purified by column chromatography using EA and petether (7: 97) as eluent to afford the title compound (0.41 g) as an yellow solid. $^1$H-NMR ($\delta$ ppm, CDCl$_3$, 400 MHz): 8.42 (d, J 9, 2H), 7.86 (d, J 9, 2H), 6.94 (d, J 3.4, 1H), 5.42 (d, J 48.4, 2H).

Intermediate 22: 5-(difluoromethyl)-1-(4-nitrophenyl)-3-(trifluoromethyl)-1H-pyrazole Intermediate 20 (500 mg, 1.75 mmol) was dissolved in DCM, cooled to 0° C. and added (Diethylamino) sulphur trifluoride (0.46 ml, 3.5 mmol). This mixture was stirred at ambient temperature for 30 mins. Water added to reaction mixture and DCM layer separated was dried on anhydrous Na$_2$SO$_4$ and DCM was removed on rotavapour to obtain the crude. Purification (60-120 mesh silica gel) [EA:Petether (60:40)] afforded the title compound as an yellow solid. $^1$H-NMR (δ ppm, CDCl$_3$, 400 MHz): 8.42 (d, J 9.1, 2H), 7.79 (d, J 9.1, 2H), 7.06 (s, 1H), 6.73 (t, J 53, 1H).

Intermediate 23: 4-chloro-3,5-dicyclopropyl-1-(2-fluoro-4-nitrophenyl)-1H-pyrazole Intermediate 10 (1.15 g, 3.40 mmol) was dissolved in DMF and to this N-Chlorosuccinimide (0.64 g, 4.8 mmol) was added at 0° C. Then reaction was allowed to stir at rt for 2h. After completion of the reaction, work up (EtOAc) and purification afforded the title compound (0.575 g). $^1$H-NMR (δ ppm, DMSO-d$_6$, 400 MHz): 8.18-8.09 (m, 2H), 7.64 (t, J 8.3, 1H), 1.98-1.90 (m, 1H), 1.82-1.72 (m, 1H), 0.90-0.80 (m, 4H), 0.68-0.60 (m, 4H).

Intermediate 24: 4-chloro-5-cyclopropyl-1-(4-nitrophenyl)-3-(trifluoromethyl)-1H-pyrazole Intermediate 13 (1 g, 3.36 mmol) was dissolved in DMF and to this N-Chlorosuccinimide (0.54 g, 4.0 mmol) was added at 0° C. Then reaction was allowed to stir at rt for 2h. After completion of the reaction, work up (EtOAc) afforded the title compound (0.802 mg). $^1$H-NMR (δ ppm, DMSO-d$_6$, 400 MHz): 8.39 (d, J 9, 2H), 7.82 (d, J 9, 2H), 1.91-1.80 (m, 1H), 1.10-1.00 (m, 2H), 0.80-0.72 (m, 2H).

Intermediate 25: 5-cyclopropyl-1-(2-fluoro-4-nitrophenyl)-3-(trifluoromethyl)-1H-pyrazole Intermediate 14 (1.05 g, 3.40 mmol) was dissolved in DMF and to this N-Chlorosuccinimide (0.545 g, 4.08 mmol) was added at 0° C. Then reaction was allowed to stir at rt for 2h. After completion of the reaction, work up (EtOAc) and purification afforded the title compound (1 g). $^1$H-NMR (δ ppm, DMSO-d$_6$, 400 MHz): 8.23-8.16 (m, 2H), 7.72 (t, J 7.5, 1H), 1.82-1.70 (m, 1H), 0.99-0.82 (m, 2H), 0.74-0.65 (m, 2H).

Intermediate 26: 2-[4-chloro-5-cyclopropyl-3-(trifluoromethyl)-1H-pyrazol-1-yl]-5-nitropyridine Intermediate 16 (1.5 g, 5.0 mmol) was dissolved in DMF and to this N-Chlorosuccinimide (0.8 g, 6 mmol) was added at 0° C. Then reaction was allowed to stir at rt for 2h. After completion of the reaction, work up (EtOAc) and purification afforded the title compound (0.802 g). $^1$H-NMR (δ ppm, DMSO-d$_6$, 400 MHz): 9.34 (d, J 2.5, 1H), 8.65 (dd, J 2.5, 9, 1H), 8.09 (d, J 9, 1H), 2.48-2.38 (m, 1H), 1.13-1.03 (m, 2H), 0.90-0.82 (m, 2H).

Intermediate 27: 4-(3,5-dicyclopropyl-1H-pyrazol-1-yl)aniline

Iron powder (0.88 g, 15.8 mmol) and ammonium chloride (17 mg, 0.3 mmol) were added to a solution of intermediate 9 (0.85 g, 3.15 mmol) in EtOH/H$_2$O (2:1, 15 mL) and the mixture refluxed for half an hour. The mixture was filtered through celite and celite washed with ethanol. Work-up (H$_2$O/AcOEt) after concentration of the combined layers afforded title compound as a yellow solid (0.68 g). $^1$H-NMR (δ ppm, DMSO-d$_6$, 400 MHz): 7.11 (d, J 8.6, 2H), 6.61 (d, J 8.6, 2H), 5.65 (s, 1H), 5.24 (s, 2H), 1.81-1.74 (m, 1H), 1.67-1.60 (m, 1H), 0.86-0.77 (m, 4H), 0.61-0.56 (m, 4H). MS (m/z): 240.3 [M+H]$^+$.

Intermediate 28: 4-(3,5-dicyclopropyl-1H-pyrazol-1-yl)-3-fluoroaniline

Iron powder (1.86 g, 34.8 mmol) and ammonium chloride (30 mg, 0.7 mmol) were added to a solution of intermediate 10 (2 g, 7.0 mmol) in EtOH/H$_2$O (2:1, 30 mL) and the mixture refluxed for one hour. The mixture was filtered through celite and celite washed with ethanol. Work-up (H$_2$O/AcOEt) and concentration of the combined layers afforded title compound as a yellow solid (1.34 g).

Intermediate 29: 4-(4-chloro-3,5-dicyclopropyl-1H-pyrazol-1-yl)-3-fluoroaniline Iron powder (0.48 g, 8.9 mmol) and ammonium chloride (9 mg, 0.17 mmol) were added to a solution of intermediate 23 (0.57 g, 1.8 mmol) in EtOH/H$_2$O (2:1, 7.5 mL) and the mixture refluxed for one hour. The mixture was filtered through celite and celite washed with ethanol. Work-up (H$_2$O/AcOEt) after concentration of the combined layers afforded intermediate 29 as a yellow solid (0.46 g). $^1$H-NMR (δ ppm, DMSO-d$_6$, 400 MHz): 7.02 (t, J 8.6, 1H), 6.45-6.38 (m, 2H), 5.74 (s, 2H), 1.85-1.76 (m 1H), 1.61-1.52 (m, 1H), 0.90-0.82 (m, 2H), 0.78-0.70 (m, 4H), 0.69-0.60 (m, 2H). MS (m/z): 291.98 [M+H]$^+$.

Intermediate 30: 6-(3,5-dicyclopropyl-1H-pyrazol-1-yl)pyridin-3-amine

Iron powder (0.79 g, 14.17 mmol) and ammonium chloride (15 mg, 0.28 mmol) were added to a solution of intermediate 11 (0.77 g, 2.86 mmol) in EtOH/H$_2$O (2:1, 15 mL) and the mixture refluxed for one hour. The mixture was filtered through celite and celite washed with ethanol. Work-up (H$_2$O/AcOEt) after concentration of the combined layers afforded intermediate 30 as a yellow solid (0.570 g). $^1$H-NMR (δ ppm, DMSO-d$_6$, 400 MHz): 7.75 (d, J 2.5, 1H), 7.27 (d, J 8.6, 1H), 7.06 (dd, J 2.7, 8.6, 1H), 5.67 (s, 1H), 5.43 (s, 2H), 2.39-2.27 (m, 1H), 1.88-1.74 (m, 1H), 0.90-0.72 (m, 4H), 0.69-0.50 (m, 4H).

Intermediate 31: 4-[5-cyclopropyl-3-(trifluoromethyl)-1H-pyrazol-1-yl]aniline A procedure similar to that employed for intermediate 27 was followed. From intermediate 13 (0.69 g, 2.32 mmol), EtOH-H$_2$O (2:1, 12 mL), Fe (0.64 g, 15.8 mmol) and NH$_4$C (0.012 mg, 0.22 mmol), the title compound was obtained as yellow solid (0.49 g). $^1$H-NMR (δ ppm, DMSO-d$_6$, 400 MHz): 7.19 (d, J 8.64, 2H), 6.65 (d, J 8.64, 2H), 6.47 (s, 1H), 5.46 (s, 2H), 1.75-1.69 (m, 1H), 0.94-0.89 (m, 2H), 0.77-0.73 (m, 2H). MS (m/z): 268.1 [M+H]$^+$.

Intermediate 32: 4-[4-chloro-5-cyclopropyl-3-(trifluoromethyl)-1H-pyrazol-1-yl]aniline Iron powder (0.67 g, 12.05 mmol) and ammonium chloride (25 mg, 4.8 mmol) were added to a solution of intermediate 24 (0.800 g, 2.41 mmol) in EtOH/H$_2$O (2:1, 15 mL) and the mixture refluxed for one hour. The mixture was filtered through celite and celite washed with ethanol. Work-up (H$_2$O/AcOEt) and concentration of the combined layers afforded intermediate 32 as a yellow solid (0.720 g).

¹H-NMR (δ ppm, DMSO-d₆, 400 MHz): 7.19 (d, J 8.6, 2H), 6.63 (d, J 8.6, 2H), 5.51 (s, 2H), 1.89-1.80 (m, 1H), 0.88-0.80 (m, 2H), 0.65-0.61 (m, 2H).

Intermediate 33: 4-[3-cyclopropyl-5-(trifluoromethyl)-1H-pyrazol-1-yl]-3-fluoroaniline Iron powder (4.75 g, 85.1 mmol) and ammonium chloride (90 mg, 1.7 mmol) were added to a solution of intermediate 14 (5 g, 17.00 mmol) in EtOH/H₂O (2:1, 45 mL) and the mixture refluxed for one hour. The mixture was filtered through celite and celite washed with ethanol. Work-up (H₂O/AcOEt) after concentration of the combined layers afforded titled compound as a yellow solid (4.3 g). ¹H-NMR (δ ppm, DMSO-d₆, 400 MHz): 7.16 (t, J 8.5, 1H), 6.50-6.45 (m, 3H), 5.86 (s, 2H), 1.60-1.51 (m, 1H), 0.91-0.82 (m, 2H), 0.76-0.69 (m, 2H).

Intermediate 34: 4-(4-chloro-5-cyclopropyl-3-(trifluoromethyl)-1H-pyrazol-1-yl)-3-fluoroaniline Iron powder (0.8 g, 56 mmol) and ammonium chloride (300 mg, 5.8 mmol) were added to a solution of intermediate 26 (1.0 g, 2.88 mmol) in EtOH/H₂O (2:1, 15 mL) and the mixture refluxed for one hour. The mixture was filtered through celite and celite washed with ethanol. Work-up (H₂O/AcOEt) and concentration of the combined layers afforded intermediate 34 as a pale-yellow solid (0.87 g). ¹H-NMR (δ ppm, DMSO-d₆, 400 MHz): 7.19 (t, J 8.6, 1H), 6.50-6.45 (m, 2H), 5.91 (s, 2H), 1.72-1.62 (m, 1H), 0.87-0.79 (m, 2H), 0.76-0.67 (m, 2H).

Intermediate 35: 4-(5-cyclopropyl-3-(trifluoromethyl)-1H-pyrazol-1-yl)-3,5-difluoroaniline Iron powder (1.14 g, 20.5 mmol) and ammonium chloride (21 mg 0.41 mmol) were added to a solution of intermediate 15 (1.36 g, 4.1 mmol) in EtOH/H₂O (2:1, 30 mL) and the mixture refluxed for one hour. The mixture was filtered through celite and celite washed with ethanol. Work-up (H₂O/AcOEt) and concentration of the combined layers afforded title compound (680 mg) as a yellow solid. ¹H-NMR (δ ppm, DMSO-d₆, 400 MHz): 6.54 (s, 1H), 6.37 (d, J 10.6, 21H), 6.24 (s, 2H), 1.59-1.49 (m, 1H), 0.92-0.84 (m, 2H), 0.74-0.66 (m, 2H). MS (m/z): 304.06 ([M+H]⁺).

Intermediate 36: 6-[5-cyclopropyl-3-(trifluoromethyl)-1H-pyrazol-1-yl]pyridin-3-amine Iron powder (0.279 g, 5.00 mmol) and ammonium chloride (5 mg, 0.09 mmol) were added to a solution of intermediate 16 (0.77 g, 2.86 mmol) in EtOH/H₂O (2:1, 9 mL) and the mixture refluxed for one hour. The mixture was filtered through celite and celite washed with ethanol. Work-up (H₂O/AcOEt) after concentration of the combined layers afforded intermediate 36 as a yellow solid (0.239 g). ¹H-NMR (δ ppm, DMSO-d₆, 400 MHz): 7.84 (d, J 2.6, 1H), 7.33 (d, J 8.6, 1H), 7.12 (dd, J 2.6, 8.6, 1H), 6.49 (s, 1H), 5.69 (s, 2H), 2.45-2.36 (m, 1H), 0.90-0.81 (m, 2H), 0.74-0.65 (m, 2H). MS (m/z): 269.2 [M+H]⁺.

Intermediate 37: 6-[4-chloro-5-cyclopropyl-3-(trifluoromethyl)-1H-pyrazol-1-yl]pyridin-3-amine Iron powder (1.56 g, 28.0 mmol) and ammonium chloride (600 mg, 11.2 mmol) were added to a solution of intermediate 26 (1.7 g, 5.60 mmol) in EtOH/H₂O (2:1, 15 mL) and the mixture refluxed for one hour. The mixture was filtered through celite and celite washed with ethanol. Work-up (H₂O/AcOEt) and concentration of the combined layers afforded intermediate 37 as a yellow solid (1.1 g). ¹H-NMR (δ ppm, DMSO-d₆, 400 MHz): 8.04 (s, 1H), 7.39 (d, J 8.2, 1H), 7.20 (d, J 8, 1H), 4.26 (s, 2H), 2.10-1.99 (m, 1H), 1.96-1.85 (m, 2H), 1.84-1.70 (m, 2H).

Intermediate 38: 2-[5-cyclopropyl-3-(trifluoromethyl)-1H-pyrazol-1-yl]pyrimidin-5-amine Iron powder (466 mg, 1.67 mmol) and ammonium chloride (8 mg, 0.17 mmol) were added to a solution of intermediate 17 (0.41 g, 1.41 mmol) in EtOH/H₂O (2:1, 7.5 mL) and the mixture refluxed for one hour. The mixture was filtered through celite and celite washed with ethanol. Work-up (H₂O/AcOEt) and concentration of the combined layers afforded intermediate 38 (0.35 g) as a yellow solid. ¹H-NMR (δ ppm, DMSO-d₆, 400 MHz): 8.20 (s, 2H), 6.52 (s, 1H), 5.99 (s, 2H), 2.22-2.12 (m, 1H), 1.00-0.85 (m, 2H), 0.80-0.68 (m, 2H). MS (m/z): 267.73 ([M–H]⁻).

Intermediate 39: 4-[5-(fluoromethyl)-3-(trifluoromethyl)-1H-pyrazol-1-yl]aniline Iron powder (434 mg, 7.78 mmol) and ammonium chloride (8 mg, 0.15 mmol) were added to a solution of intermediate 21 (450 mg, 1.56 mmol) in EtOH/H₂O (2:1, 15 mL) and the mixture refluxed for one hour. The mixture was filtered through celite and celite washed with ethanol. Work-up (H₂O/AcOEt) and concentration of the combined layers afforded title compound (335 mg) as a yellow solid (460 mg). ¹H-NMR (δ ppm, DMSO-d₆, 400 MHz): 7.16 (d, J 8.6, 2H), 7.12 (d, J 2.8, 1H), 6.65 (d, J 8.6, 2H), 5.5 (s, 2H), 5.4 (d, J 48.3, 2H).

Intermediate 40: 4-[5-(difluoromethyl)-3-(trifluoromethyl)-1H-pyrazol-1-yl]aniline Iron powder (0.39 g, 7.78 mmol) and ammonium chloride (90 mg, 1.7 mmol) were added to a solution of intermediate 22 (0.41 g, 1.41 mmol) in EtOH/H₂O (2:1, 7.5 mL) and the mixture refluxed for one hour. The mixture was filtered through celite and celite washed with ethanol. Work-up (H₂O/AcOEt) and concentration of the combined layers afforded intermediate 40 (0.35 g) as a yellow solid. ¹H-NMR (δ ppm, DMSO-d₆, 400 MHz): 7.29 (s, 1H), 7.16 (d, J 8.7, 2H), 7.10 (t, J 53, 1H), 6.64 (d, J 8.7, 2H), 5.60 (s, 2H).

Intermediate 41: 2-chloro-N-[4-(3,5-dicyclopropyl-1H-pyrazol-1-yl)phenyl]acetamide Chloroacetyl chloride (0.2 mL, 2.39 mmol) was added to a solution of intermediate 27 (600 mg, 2.24 mmol) in dichloromethane (DCM) at 0° C. The mixture was stirred for 15 mins. Work-up (H₂O/DCM) gave the intermediate 41 which was used in the next step without further purification.

Intermediate 42: 2-chloro-N-{4-[5-cyclopropyl-3-(trifluoromethyl)-1H-pyrazol-1-yl]phenyl}acetamide Chloroacetyl chloride (0.05 mL, 0.62 mmol) was added to a solution of intermediate 31 (150 mg, 0.561 mmol) in dichloromethane (DCM) at 0° C. The mixture was stirred for 15 mins. Work-up (H₂O/DCM) gave the titled compound, which was used in the next step without further purification.

Intermediate 43: 2-chloro-N-{6-[5-cyclopropyl-3-(trifluoromethyl)-1H-pyrazol-1-yl]pyridin-3-yl}acetamide Chloroacetyl chloride (0.16 mL, 2.00 mmol) was added to a solution of intermediate 36 (500 mg, 1.86 mmol) in dichloromethane (DCM) at 0° C. The mixture was stirred for 15 mins. Work-up (H$_2$O/DCM) gave the intermediate 43 which was used in the next step without further purification.

Intermediate 44: 5-cyclopropyl-1-(4-iodophenyl)-3-(trifluoromethyl)-1H-pyrazole To the intermediate 31 (2 g, 7.49 mmol) in 5 ml water was added Conc. HCl (5 ml) and cooled to 0° C. To this sodium nitrite solution (1 g, 15 mmol) was added slowly and stirred for 15 mins at 0° C. To this mixture potassium iodide solution (2.5 g, 15 mmol), was added at same temperature and stirred the reaction mixture at rt. Work-up (H$_2$O/AcOEt) and purification gave the desired product as a yellow liquid. $^1$H-NMR (δ ppm, CDCl$_3$, 400 MHz): 7.92 (d, J 8.6, 2H), 7.47 (d, J 8.6, 2H), 6.65 (s, 1H), 1.90-1.80 (m, 1H), 1.00-0.90 (m, 2H), 0.85-0.77 (m, 2H).

Intermediate 45: 5-cyclopropyl-1-(2-fluoro-4-iodophenyl)-3-(trifluoromethyl)-1H-pyrazole To the intermediate 33 (1.9 g, 7.20 mmol) in 5 ml water was added Conc. HCl (5 ml) and cooled to 0° C. To this sodium nitrite solution (1 g, 15 mmol) was added slowly and stirred for 15 mins at 0° C. To this mixture potassium iodide solution (2.5 g, 15 mmol) was added at same temperature and stirred the reaction mixture at rt. Work-up (H$_2$O/AcOEt) and purification gave the desired product as a yellow colour liquid. $^1$H-NMR (δ ppm, DMSO-d$_6$, 400 MHz): 8.01 (dd, J 1.7, 9.5, 1H), 7.79 (dd, J 1.7, 8.4, 1H), 7.45 (t, J 8.1, 1H), 6.63 (s, 1H), 1.64-1.56 (m, 1H), 0.92-0.84 (m, 2H), 0.79-0.71 (m, 2H).

Intermediate 46: 6-(3,5-dicyclopropyl-1H-pyrazol-1-yl)nicotinic acid

To a solution of intermediate 12 (300 mg, 1 mmol) in THF:H$_2$O (1:1) added Potassium hydroxide (83 mg, 1.5 mmol) and refluxed for 5 h. After completion of the reaction, reaction mixture was acidified with 2N HCl and worked up (H$_2$O/AcOEt) to afford the title compound (240 mg). $^1$H-NMR (δ ppm, DMSO-d$_6$, 400 MHz): 13.3 (bs, 1H), 8.90 (d, J 2.0, 1H), 8.35 (dd, J 2.2, 8.6, 1H), 7.89 (d, J 8.6, 1H), 5.93 (s, 1H), 2.90-2.80 (m, 1H), 1.90-1.80 (m, 1H), 1.00-0.82 (m, 4H), 0.75-0.62 (m, 4H).

Intermediate 47: 4-(5-cyclopropyl-3-(trifluoromethyl)-1H-pyrazol-1-yl)benzoic acid Magnesium (32 mg, 1.32 mmol) and a pinch of iodine suspended in ether under inert atmosphere. To this small amount of methyl iodide was added and refluxed the reaction mixture to start Grignard formation. At this stage intermediate 44 (500 mg, 1.32 mmol) was added and continued the reaction under reflux condition. After complete consumption of the starting material, reaction mixture cooled to rt and added dry ice pieces into it followed by con. HCl. Solid that formed was filtered and dried on high vacuum to obtain the title compound (100 mg) as a yellow solid. $^1$H-NMR (δ ppm, DMSO-d$_6$, 400 MHz): 13.2 (bs, 1H), 8.11 (d, J 8.6, 2H), 7.82 (d, J 8.6, 2H), 6.7 (s, 1H), 1.99-1.90 (m, 1H), 1.04-0.94 (m, 2H), 0.88-0.80 (m, 2H).

Intermediate 48: 4-[5-cyclopropyl-3-(trifluoromethyl)-1H-pyrazol-1-yl]-3-fluorobenzoic acid Magnesium (143 mg, 6 mmol) and a pinch of iodine suspended in ether under inert atmosphere. To this small amount of methyl iodide was added and refluxed the reaction mixture to start Grignard formation. At this stage intermediate 45 (790 mg, 2 mmol) was added and continued the reaction under reflux condition. After complete consumption of the starting material, reaction mixture cooled to rt and added dry ice pieces into it followed by 2N HCl. Solid that formed was filtered and dried on high vacuum to obtain the title compound (160 mg) as an off-white solid. $^1$H-NMR (δ ppm, DMSO-d$_6$, 400 MHz): 13.6 (bs, 1H), 7.97-7.92 (m, 2H), 7.84-7.78 (m, 1H), 6.68 (s, 1H), 1.69-1.61 (m, 1H), 0.94-0.87 (m, 2H), 0.80-0.74 (m, 2H).

Intermediate 49: Ethyl 6-[5-cyclopropyl-3-(trifluoromethyl)-1H-pyrazol-1-yl]nicotinate A solution of intermediate 5 (0.84 g, 4.7 mmol) and K$_2$CO$_3$ (1.9 g, 14.1 mmol) in DMSO (10 mL) was heated at 80° C. under nitrogen for 0.5 h. To the mixture, ethyl-6-chloronicotinate (3.8 g, 20.3 mmol) was added and stirred at 80° C. for 4 h. Work-up (H$_2$O/AcOEt) and purification afforded the title compound (0.26 g). $^1$H-NMR (δ ppm, CDCl$_3$, 400 MHz): 9.11 (d, J 1, 1H), 8.44 (d, J 2.2, 8.6, 1H), 8.00 (d, J 8.6, 1H), 6.25 (s, 1H), 4.45 (q, J 7.1, 2H), 2.91-2.80 (m, 1H), 1.43 (t, J 7.1, 3H), 1.11-1.01 (m, 2H), 0.79-0.70 (m, 2H).

Intermediate 50: 6-(5-cyclopropyl-3-(trifluoromethyl)-1H-pyrazol-1-yl)nicotinic acid To a solution of intermediate 49 (600 mg, 1.8 mmol) in MeOH:H$_2$O (2:1) added sodium hydroxide (221 mg, 5.4 mmol) and refluxed for 2 h. After completion of the reaction, reaction mixture was acidified with 2N HCl and worked up (H$_2$O/AcOEt) to afford the pure compound (452 mg). $^1$H-NMR (δ ppm, DMSO-d$_6$, 400 MHz): 9.18 (d, J 2.0, 1H), 8.50 (dd, J 2.2, 8.6, 1H), 8.07 (d, J 8.6, 1H), 6.27 (s, 1H), 2.92-2.82 (m, 1H), 1.14-1.04 (m, 2H), 0.78-0.71 (m, 2H).

Intermediate 51: ethyl 2-[(dimethylamino)methylene]-3-oxobutanoate

Ethyl acetoacetate (15 g, 115 mmol) and N,N-Dimethylformamide dimethyl Acetal (13.7 g, 115 mmol) stirred at rt for overnight. After completion of the reaction, reaction mixture distilled on rotavapour to obtain the crude. Crude was purified by column chromatography over 60-120 mesh silica gel using EtOAc and petether (10:90) as eluent to obtain the title compound (20 g).

Intermediate 52: ethyl 4-methylpyrimidine-5-carboxylate

Intermediate 51 (9.7 g, 52.4 mmol) and Formamidine acetate (5.4 g, 52.4 mmol), were dissolved in EtOH and added NaOEt (3.6 g, 52.4 mmol). This mixture was refluxed for 6h. After that, ethanol removed on rotavapour followed by work-up (AcOEt/H$_2$O) to obtain the crude. Crude was purified by column chromatography using 60-120 mesh silicagel and AcOEt and Petether (25:75) as eluent to obtain the title compound (2.7 g).

Intermediate: 53: 4-methylpyrimidine-5-carboxylic acid

Intermediate 52 (2.6 g, 15.64 mmol) dissolved in sodium hydroxide solution (1.88 g, 47 mmol in 4 ml water) and refluxed. The reaction mixture was cooled to rt and acidified with con HCl to obtain the solid. Solid that obtained was filtered and dried to obtain the title compound (1.5 g) as an yellow solid. $^1$H-NMR ($\delta$ ppm, DMSO-$d_6$, 400 MHz): 13.5 (bs, 1H), 9.14 (s, 1H), 9.05 (s, 1H), 2.71 (s, 3H).

Intermediate 54: ethyl 2,4-dimethylpyrimidine-5-carboxylate

Intermediate 51 (17.6 g, 95 mmol) and acetamidine hydrochloride (17.6 g, 95 mmol), were dissolved in EtOH and added NaOEt (6.5 g, 95 mmol). This mixture was refluxed for 4h. After that, ethanol removed on rotavapour followed by work-up (AcOEt/H$_2$O) to obtain the crude. Crude was purified by column chromatography using 60-120 mesh silicagel and AcOEt and Petether (25:75) as eluent to obtain the title compound (7.3 g).

Intermediate 55: 2,4-dimethylpyrimidine-5-carboxylic acid

Intermediate 54 (7.3 g, 40.5 mmol) dissolved in sodium hydroxide solution (4.86 g, 121.6 mmol in 10 ml water) and refluxed. The reaction mixture was cooled to rt and acidified with con HCl to obtain the solid. Solid that obtained was filtered and dried to obtain the title compound quantitatively as an yellow solid. $^1$H-NMR ($\delta$ ppm, DMSO-$d_6$, 400 MHz): 13.5 (bs, 1H), 8.93 (s, 1H), 2.66 (s, 3H), 2.60 (s, 3H).

Intermediate 56: ethyl 4-methylthiazole-5-carboxylate 4-methylthiazole-5-carboxylic acid was dissolved in DCM, cooled to 0° C., added oxalyl chloride (7.6 ml, 88 mmol) and DMF (2 drops). Reaction mixture was stirred for 30 mins and DCM was removed on rotavapour. Residue was dissolved in MeOH at 0° C. and stirred for 30 mins at rt. MeOH was removed on rotavapour and crude was worked up (AcOEt/H$_2$O) to obtain the title compound (4.1 g) as a white solid. $^1$H-NMR ($\delta$ ppm, CDCl$_3$, 400 MHz): 8.83 (s, 1H), 4.35 (q, J 7.2, 2H), 2.78 (s, 3H), 1.37 (t, J 7.2, 3H).

Intermediate 57: (4-methylthiazol-5-yl)methanol

Intermediate 56 (262 mg, 1.6 mmol) was dissolved in MeOH and added sodium borohydride (126 mg, 3.2 mmol) and stirred the reaction mixture at rt for overnight. MeOH was removed on rotavapour and residue was worked up (AcOEt/H$_2$CO) to obtain the title compound (183 mg) as a white solid. $^1$H-NMR ($\delta$ ppm, CDCl$_3$, 400 MHz): 8.67 (s, 1H), 4.82 (s, 2H), 2.44 (s, 3H).

Intermediate 58: 4-methylthiazole-5-carbaldehyde

Oxalyl chloride (0.8 ml, 9.8 mmol) was dissolved in DCM, cooled to −78° C. and added DMSO (1.39 ml 19.6 mmol) and stirred for 30 mins. To this intermediate 57 (630 mg, 4.9 mmol) was added, stirred at −78° C. for 20 mins and added triethyl amine (2.7 ml, 7.6 mmol). Reaction mixture warmed to 0° C. and then slowly heated to rt. Work up (H$_2$O/AcOEt) afforded the title compound (408 mg) as a yellow solid. 10.13 (s, 1H), 9.37 (s, 1H), 2.71 (s, 3H).

Intermediate 59: 4-methylthiazol-5-amine

4-Methylthiazole-5-carboxylic acid (1 g, 7 mmol) was dissolved in acetone (50 mL) and cooled to 0° C. To this mixture triethyl amine (0.84 g, 8.3 mmol) was added and after 5 mins ethylchloroformate (0.9 g, 8.3 mmol) was added slowly. This mixture stirred at rt for 1 h and then Sodium azide solution (0.9 g, 13.8 mmol in 5 ml H$_2$O) was added to it at 0° C. The reaction mixture was stirred for half an hour at rt, acetone was removed and residue was extracted with ether. Ether removed on rotavapour to obtain the crude. Crude was dissolved in 1,4-dioxane, added Conc. H$_2$SO$_4$ and refluxed for 1h. The reaction mixture cooled to rt, pH adjusted to 9 with aq NaOH and extracted with EtOAc to obtain the title compound (0.24 g) as a brown solid. $^1$H-NMR ($\delta$ ppm, DMSO-$d_6$, 400 MHz): 7.98 (s, 1H), 5.13 (s, 2H), 2.11 (s, 3H).

Intermediate 60: 1-phenylcyclobutanecarbonitrile

Sodium hydride (1.54 g, 64.1 mmol) dissolved in DMF (15 ml) and cooled to 0° C. Phenyl acetonitrile (3 g, 25.6 mmol) and 1,3-dibromopropane (5.2 g, 25.6 mmol) were dissolved in DMF (15 ml) and added to above mixture drop-wise at 0° C. This mixture was heated to rt and continued stirring for 2h. Work up (H$_2$O/Toluene) afforded the title compound (2.61 g) as crude, which was used in the next without further purification.

Intermediate 61: 1-phenylcyclobutanecarboxylic acid

Intermediate 60 (2.6 g, 16.54 mmol) was dissolved in ethyleneglycol and added potassium hydroxide (5.6 g, 99.2 mmol). This mixture was heated to 160° C. for 2h. After two hours reaction mixture was cooled to rt and toluene and water were added. Aqueous layer separated and acidified with HCl and pH adjusted to 4. Aqueous layer extracted with ethyl acetate and ethyl acetate layer was dried on anhydrous sodium sulphate. Ethyl acetate removed on rotavapour to obtain the title compound (930 mg) as a white solid.

Intermediate 62: (Z)-1-cyclopropyl-4,4-difluoro-3-hydroxybut-2-en-1-one

Hexamethyldisilazane (1 g, 6.2 mmol) and diethylether were taken in RBF and cooled to −78° C. under nitrogen atmosphere. n-BuLi (7.7 ml) was added and stirred for 15 mins. Cyclopropyl methyl ketone (0.66 ml, 6.8 mmol) was added and stirred at −78° C. for 45 mins. At this stage methyl 2,2-difluoroacetate (1.62 ml, 18.58 mmol) was added and brought the reaction mixture to rt and allowed to stir for overnight. Reaction mixture quenched with water, ether layer separated and aqueous layer was acidified with 1N HCl. Aqueous layer extracted with diethyl ether and ether was dried over anhydrous Na$_2$SO$_4$. Diethyl ether was removed on rotavapour to obtain the title compound (390 mg) which was used in the next step without further purification. $^1$H-NMR ($\delta$ ppm, CDCl$_3$, 400 MHz): 6.08 (s, 1H), 5.95 (t, J 54.2, 1H), 1.84-1.76 (m, 1H), 1.34-1.29 (m, 2H), 1.10-1.03 (m, 2H).

Intermediate 63:
5-cyclopropyl-3-(difluoromethyl)-1H-pyrazole

Intermediate 62 (390 mg, 2.4 mmol) dissolved in ethanol (2 ml), added hydrazine hydrate (0.13 ml, 2.65 mmol) and HCl (0.18 ml). This mixture was refluxed for 3 h. After 3 h, ethanol was removed on rotavapour and work up (H$_2$O/AcOEt) afforded the title compound (290 mg) which was used in the next step without further purification. $^1$H-NMR (5 ppm, CDCl$_3$, 400 MHz): 12.96 (s, 1H), 6.84 (t, J 54.8, 1H), 6.15 (s, 1H), 1.95-1.87 (m, 1H), 0.99-0.91 (m, 2H), 0.74-0.66 (m, 2H).

Intermediate 64: Mixture of 3-cyclopropyl-5-(difluoromethyl)-1-(2-fluoro-4-nitrophenyl)-1H-pyrazole and 5-cyclopropyl-3-(difluoromethyl)-1-(2-fluoro-4-nitrophenyl)-1H-pyrazole Intermediate 63 (100 mg, 0.63 mmol), Cs$_2$CO$_3$ (622 mg, 1.9 mmol), acetone (5 mL) were mixed and heated to reflux. After 30 mins, 1,2-difluoro-4-benzene (253 mg, 1.59 mmol) was added and continued the reaction for 1 h. Work up (H$_2$O/AcOEt) followed by purification using 60-120 mesh silica gel and EtOAc and Petether (3:97) as eluent afforded the title compound (65 mg), $^1$H-NMR (6 ppm, CDCl$_3$, 400 MHz): 8.23-8.10 (m, 2H), 7.78-7.72 (m, 1H), 6.71 (t, J 54.8, 0.37H), 6.66 (t, J 54.8, 0.63H), 6.43 (s, 0.37H), 6.25 (s, 0.63H), 2.05-1.95 (m, 0.37H), 1.70-1.61 (m, 0.63H), 1.04-0.94 (m, 2H), 0.86-0.80 (m, 0.74H), 0.77-0.71 (m, 1.26H).

Intermediate 65: Mixture of 4-(3-cyclopropyl-5-(difluoromethyl)-1H-pyrazol-1-yl)-3-fluoroaniline and 4-(5-cyclopropyl-3-(difluoromethyl)-1H-pyrazol-1-yl)-3-fluoroaniline Iron powder (120 mg, 2.31 mmol) and ammonium chloride (2 mg, 0.046 mmol) were added to a solution of intermediate 64 (130 mg, 0.46 mmol) in EtOH/H$_2$O (2:1, 1.65 mL) and the mixture refluxed for half an hour. The mixture was filtered through celite and celite washed with ethanol. Work-up (H$_2$O/AcOEt) and concentration of the combined layers afforded title compound as a yellow solid (90 mg). $^1$H-NMR (δ ppm, DMSO-d$_6$, 400 MHz): 7.12 (t, J 8.5, 0.63H), 7.08-7.03 (m, 0.37H), 6.90 (t, J 54.8, 0.63H), 6.84 (t, J 54.8, 0.37H), 6.50-6.38 (m, 2.37H), 6.25 (s, 0.63H), 5.81 (s, 2H), 1.95-1.86 (m, 0.37H), 1.57-1.48 (m, 0.63H), 0.90-0.82 (m, 2H), 0.71-0.64 (m, 2H).

General Procedure for Amide Formation:

Procedure-1: A solution of an appropriate aniline (1 eq.), the requisite acid (1.1 eq.), EDC.HCl (1.2 eq.), HOBt (0.5 eq.) and TEA (3 eq.) in DMF was stirred at RT overnight. Work-up (H$_2$O/AcOEt) and purification gave the desired product.

Procedure-2: Acid (1 eq.) was dissolved in DCM, cooled to 0° C., added oxalyl chloride (3 eq.) and three drops of DMF. The reaction mixture was stirred at room temperature for 30 mins and DCM was removed on rotavapour to obtain the acid chloride. Amine was dissolved in DCM under N$_2$ atmosphere and added Pyridine (1.3 eq). To this mixture acid chloride in DCM was added and allowed to stir at room temperature until amine was totally consumed. Work-up (H$_2$O/AcOEt) and purification gave the desired product.

The following compounds were prepared using these procedures:

Example 1

N-[4-(3,5-dicyclopropyl-1H-pyrazol-1-yl)phenyl]-4-methyl-1,2,3-thiadiazole-5-carboxamide Following the general procedure-1, the title compound (60 mg) was prepared from 4-methyl-1,2,3-thiadiazole-5-carboxylic acid (86 mg, 0.60 mmol) and intermediate 27 (120 mg, 0.50 mmol) as a white solid. M.P.: 117-120° C. $^1$H-NMR (δ ppm, DMSO-d$_6$, 400 MHz): 10.86 (s, 1H), 7.79 (d, J 8.8, 2H), 7.59 (d, J 8.8, 2H), 5.81 (s, 1H), 2.81 (s, 3H), 1.84-1.77 (m, 2H), 0.92-0.90 (m, 2H), 0.89-0.81 (m, 2H), 0.68-0.61 (m, 4H). MS (m/z): 363.96 [M−H]$^-$.

Example 2

N-[4-(3,5-dicyclopropyl-1H-pyrazol-1-yl)phenyl]-4-methylthiazole-5-carboxamide

Following the general procedure-1, the title compound (102 mg) was prepared from 4-methylthiazole-5-carboxylic acid (78 mg, 0.54 mmol) and intermediate 27 (120 mg, 0.50 mmol) as an off-white solid. M. P. 110-114° C. $^1$H-NMR (δ ppm, DMSO-d$_6$, 400 MHz): 10.37 (s, 1H), 9.13 (s, 1H), 7.78 (d, J 8.7, 2H), 7.55 (d, J 8.7, 2H), 5.79 (s, 1H), 2.61 (s, 3H), 1.89-1.71 (m, 2H), 0.94-0.80 (m, 4H), 0.69-0.60 (m, 4H). MS (m/z): 363.11 [M−H]$^-$.

Example 3

N-[4-(3,5-dicyclopropyl-1H-pyrazol-1-yl)phenyl]-2,4-dimethylthiazole-5-carboxamide Following the general procedure-1, the title compound (87 mg) was prepared from 2,4-dimethylthiazole-5-carboxylic acid (94 mg, 0.59 mmol) and intermediate 27 (120 mg, 0.50 mmol) as an off-white solid. M. P. 98-114° C. $^1$H-NMR (δ ppm, DMSO-d$_6$, 400 MHz): 10.22 (s, 1H), 7.76 (d, J 8.4, 2H), 7.52 (d, J 8.4, 2H), 5.79 (s, 1H), 2.66 (s, 3H), 2.54 (s, 3H), 1.88-1.73 (m, 2H), 0.95-0.82 (m, 4H), 0.69-0.61 (m, 4H). MS (m/z): 379.20 [M+H]$^+$.

Example 4

N-[4-(3,5-dicyclopropyl-1H-pyrazol-1-yl)phenyl]-5-methylisoxazole-4-carboxamide

Following the general procedure-2, the title compound (55 mg) was prepared from 5-methylisoxazole-4-carbonyl chloride (79 mg) and intermediate 27 as a white solid. M. P. 153-158° C. $^1$H-NMR (δ ppm, DMSO-d$_6$, 400 MHz): 10.17 (s, 1H), 9.06 (s, 1H), 7.79 (d, J 7.6, 2H), 7.56 (d, J 7.6, 2H), 5.80 (s, 1H), 2.68 (s, 3H), 1.84-1.78 (m, 2H), 0.91-0.70 (m, 4H), 0.69-0.55 (m, 4H). MS (m/z): 347.08 [M−H]$^-$.

Example 5

N-[4-(3,5-dicyclopropyl-1H-pyrazol-1-yl)phenyl]-3,5-dimethylisoxazole-4-carboxamide Following the general procedure-1, the title compound (147 mg) was prepared from 3,5-dimethylisoxazole-4-carboxylic acid (155 mg, 1 mmol) and intermediate 27 (150 mg, 0.62 mmol) as a yellow solid. M.P.: 115-119° C. $^1$H-NMR (δ ppm, DMSO-d$_6$, 400 MHz): 10.18 (s, 1H), 7.76 (d, J 8.7, 2H), 7.55 (d, J 8.7, 2H), 5.79 (s, 1H), 2.55 (s, 3H), 2.33 (s, 3H), 1.88-1.73 (m, 2H), 0.94-0.80 (m, 4H), 0.70-0.61 (m, 4H). MS (m/z): 363.27 [M+H]⁺.

Example 6

N-[4-(3,5-dicyclopropyl-1H-pyrazol-1-yl)phenyl]benzamide

Following the general procedure-2, title compound (90 mg) was prepared from benzoyl chloride (64 mg, 0.45 mmols) and intermediate 27 (100 mg, 0.41 mmols) as a pale yellow solid. M. P. 133-138.5° C. ¹H-NMR (δ ppm, DMSO-d₆, 400 MHz): 10.39 (s, 1H), 7.96 (d, J 7.1, 2H), 7.91 (d, J 9.0, 2H), 7.61-7.51 (m, 5H), 5.79 (s, 1H), 1.85-1.76 (m, 2H), 0.93-0.81 (m, 4H), 0.68-0.61 (m, 4H). MS (m/z): 341.9 [M–H]⁻.

Example 7

N-[4-(3,5-dicyclopropyl-1H-pyrazol-1-yl)phenyl]-2-methylbenzamide

Following the general procedure-1, the title compound (130 mg) was prepared from intermediate 27 (200 mg, 0.84 mmol) and o-toluic acid (182 mg, 1.34 mmol) as an yellow solid. M.P.: 127.5-129.8° C. ¹H-NMR (δ ppm, DMSO-d₆, 400 MHz): 10.44 (s, 1H), 7.85 (d, J 8.8, 2H), 7.57 (d, J 8.7, 1H), 7.53 (d, J 8.8, 2H), 7.47 (d, J 7.5, 1H), 7.42-7.37 (m, 1H), 7.33-7.27 (m, 2H), 2.38 (s, 3H), 1.90-1.73 (m, 2H), 0.93-0.80 (m, 4H), 0.69-0.61 (m, 4H). MS (m/z): 358.03 [M+H]⁺.

Example 8

N-[4-(3,5-dicyclopropyl-1H-pyrazol-1-yl)phenyl]-2,6-difluorobenzamide

The title compound (77 mg) was prepared from 2,6-difluorobenzoic acid and intermediate 27 (120 mg, 0.50 mmol) as a white solid. M. P. 158-163° C. ¹H-NMR (δ ppm, DMSO-d₆, 400 MHz): 10.93 (s, 1H), 7.79 (d, J 8.8, 2H), 7.63-7.56 (m, 3H), 7.25 (t, J 8.0, 2H), 1.85-1.80 (m, 2H), 0.89-0.85 (m, 2H), 0.84-0.81 (m, 2H), 0.68-0.61 (m, 4H). MS (m/z): 378.4 [M–H]⁻.

Example 9

N-[4-(3,5-dicyclopropyl-1H-pyrazol-1-yl)phenyl]-2,3-difluorobenzamide

Following the general procedure-1, the title compound (120 mg) was prepared from 2,3-difluorobenzoic acid and intermediate 27 (95 mg, 0.60 mmol) as a white solid. M. P. 135-142° C. ¹H-NMR (δ ppm, DMSO-d₆, 400 MHz): 10.69 (s, 1H), 7.81 (d, J 8.8, 2H), 7.65-7.61 (m, 1H), 7.57 (d, J 8.8, 2H), 7.51-7.48 (m, 1H), 7.37-7.32 (m, 1H), 1.87-1.75 (m, 2H), 0.93-0.85 (m, 2H), 0.84-0.81 (m, 2H), 0.68-0.61 (m, 4H). MS (m/z): 380.26 [M+H]⁺.

Example 10

N-[4-(3,5-dicyclopropyl-1H-pyrazol-1-yl)phenyl-3-(methylsulfonyl)benzamide

Following the general procedure-2, the title compound (63 mg) was prepared from 3-(methylsulfonyl)benzoyl chloride (100 mg, 0.45 mmol) and intermediate 27 (120 mg, 0.50 mmol) as a pale yellow solid. M. P. 203-208° C. ¹H-NMR (δ ppm, DMSO-d₆, 400 MHz): 10.66 (s, 1H), 8.48 (s, 1H), 8.30 (d, J 7.5, 1H), 8.14 (d, J 7.5, 1H), 7.89 (d, J 8.8, 2H), 7.83 (t, J 7.8, 1H), 7.59 (d, J 8.8, 2H), 5.80 (s, 1H), 3.29 (s, 31H), 1.88-1.75 (m, 2H), 0.96-0.81 (m, 4H), 0.69-0.60 (m, 4H). MS (m/z): 422.29 [M+H]⁺.

Example 11

N-[4-(3,5-dicyclopropyl-1H-pyrazol-1-yl)phenyl]-4-(methylsulfonyl)benzamide

Following the general procedure-2, the title compound (97 mg) was prepared from 4-(methylsulfonyl)benzoyl chloride (100 mg, 0.46 mmol) and intermediate 27 (110 mg, 0.45 mmol) as an yellow solid. M. P. 171-176° C. ¹H-NMR (δ ppm, DMSO-d₆, 400 MHz): 10.64 (s, 1H), 8.18 (d, J 8.3, 2H), 8.09 (d, J 8.3, 2H), 7.89 (d, J 8.8, 2H), 7.58 (d, J 8.8, 2H), 5.80 (s, 1H), 3.29 (s, 3H), 1.92-1.85 (m, 2H), 0.90-0.81 (m, 4H), 0.68-0.61 (m, 4H). MS (m/z): 422.29 [M+H]⁺.

Example 12

2-chloro-N-[4-(3,5-dicyclopropyl-1H-pyrazol-1-yl)phenyl]-5-(methylthio)benzamide Following the general procedure-1, the title compound (24 mg) was prepared from 2-chloro-5-(methylthio)benzoic acid (109 mg, 0.54 mmol) and intermediate 27 (120 mg, 0.45 mmol) as a pale yellow solid. M. P. 168-173° C. ¹H-NMR (δ ppm, DMSO-d₆, 400 MHz): 10.66 (s, 1H), 7.82 (d, J 8.8, 2H), 7.55 (d, J 8.8, 2H), 7.49-7.45 (m, 2H), 7.39-7.36 (m, 1H), 5.79 (s, 1H), 2.52 (s, 3H), 1.87-1.74 (m, 2H), 0.93-0.88 (m, 2H), 0.86-0.81 (m, 2H), 0.67-0.61 (m, 4H). MS (m/z): 422.03 [M–H]⁻.

Example 13

2-chloro-N-[4-(3,5-dicyclopropyl-1H-pyrazol-1-yl)phenyl)-5-(methylsulfonyl)benzamide Following the general procedure-2, the title compound (58 mg) was prepared from 2-chloro-5-(methylsulfonyl)benzoyl chloride (120 mg, 0.47 mmol) and intermediate 27 (120 mg, 0.45 mmol) as a pale yellow solid. M. P. 60-65° C. ¹H-NMR (δ ppm, DMSO-d₆, 400 MHz): 10.85 (s, 1H), 8.16 (d, J 2.1, 1H), 8.03 (dd, J 2.0, 8.4, 1H), 7.88 (d, J 8.4, 1H) 7.81 (d, J 8.8, 2H), 7.58 (d, J 8.8, 2H), 5.80 (s, 1H), 3.31 (s, 3H), 1.86-1.74 (m, 2H), 0.95-0.82 (m, 4H), 0.70-0.59 (m, 4H). MS (m/z): 454.07 [M–H]⁻.

Example 14

N-[4-(3,5-dicyclopropyl-1H-pyrazol-1-yl)phenyl]nicotinamide hydrochloride

Following the general procedure-1, N-[4-(3,5-dicyclopropyl-1H-pyrazol-1-yl)phenyl]nicotinamide (220 mg) was prepared from intermediate 27 (200 mg, 0.84 mmol) and isonicotinic acid (164 mg, 1.34 mmol) as an off-white solid and dissolved in THF. Saturated HCl in diethyl ether was added to this solution at 0° C. and stirred for 15 min. Solid that separated out was filtered and dried to give the title compound (190 mg) as an off-white solid. M.P.: 230.2-232.9° C. ¹H-NMR (δ ppm, DMSO-d₆, 400 MHz): 10.97 (s, 1H), 9.34 (s, 1H), 8.94 (d, J 3.6, 1H), 8.74 (bs, 1H), 7.93 (d, J 8.8, 3H), 7.60 (d, J 8.8, 2H), 5.82 (s, 1H), 1.90-1.74 (m, 2H), 0.95-0.80 (m, 4H), 0.70-0.60 (m, 4H). MS (m/z): 345.15 [M+H–HCl]$^+$.

Example 15

N-[4-(3,5-dicyclopropyl-1H-pyrazol-1-yl)phenyl] isonicotinamide hydrochloride

Following the general procedure-1 N-[4-(3,5-dicyclopropyl-1H-pyrazol-1-yl)phenyl]isonicotinamide (40 mg) was prepared from isonicotinic acid (74 mg, 0.60 mmol) and intermediate 27 (120 mg, 0.50 mmol) as a pale yellow solid and dissolved in THF. Saturated HCl in diethyl ether was added to this solution at 0° C. and stirred for 15 min. Solid that separated out was filtered and dried to give the title compound (47 mg) as an yellow solid. M. P. 232-238° C. $^1$H-NMR (5 ppm, DMSO-d$_6$, 400 MHz): 11.08 (s, 1H), 9.01 (d, J 6.0, 2H), 8.30 (d, J 6.0, 2H), 7.94 (d, J 8.8, 2H), 7.61 (d, J 8.8, 2H), 5.83 (s, 1H), 1.90-1.74 (m, 2H), 0.95-0.80 (m, 4H), 0.70-0.60 (m, 4H). MS (m/z): 345.22 [M–H–HCl]$^-$.

Example 16

N-[4-(3,5-dicyclopropyl-1H-pyrazol-1-yl)phenyl]-3-fluoroisonicotinamide

Following the general procedure-1, the title compound (60 mg) was prepared from intermediate 27 (200 mg, 0.84 mmol) and 3-fluoroisonicotinic acid (188 mg, 1.3 mmol) as an off-white solid. M.P.: 135.2-139.3° C. $^1$H-NMR (5 ppm, DMSO-d$_6$, 400 MHz): 10.84 (s, 1H), 8.77 (s, 1H), 8.60 (d, J 4.7, 1H), 7.81 (d, J 8.9, 2H), 7.71 (t, J 5.4, 1H), 7.59 (d, J 8.9, 2H), 5.80 (s, 1H), 1.90-1.73 (m, 2H), 0.95-0.79 (m, 4H), 0.69-0.60 (m, 4H). MS (m/z): 363.14 [M+H]$^+$.

Example 17

3,5-dichloro-N-(4-(3,5-dicyclopropyl-1H-pyrazol-1-yl)phenyl)isonicotinamide

Following the general procedure-2, the title compound (168 mg) was prepared from intermediate 27 (200 mg, 0.84 mmol) and 3,6-dichloropyridine-4carboxylic acid (211 mg, 1 mmol) as a white solid. M.P.: 159-164° C. $^1$H-NMR (δ ppm, DMSO-d$_6$, 400 MHz): 11.09 (s, 1H), 8.81 (s, 2H), 7.76 (d, J 8.9, 2H) 7.60 (d, J 8.9, 2H), 5.80 (s, 1H), 1.88-1.75 (m, 2H), 0.95-0.89 (m, 2H), 0.87-0.81 (m, 2H), 0.71-0.60 (m, 4H). MS (m/z): 413.30 [M+H]$^+$.

Example 18

N-[4-(3,5-dicyclopropyl-1H-pyrazol-1-yl)phenyl]-4-methylpyrimidine-5-carboxamide Following the general procedure-1, the title compound (129 mg) was prepared from intermediate 27 (200 mg, 0.87 mmol) and 4-methylpyrimidine-5-carboxylic acid (360 mg, 2.63 mmols) as a yellow solid. M.P.: 89-95° C. $^1$H-NMR (δ ppm, DMSO-d$_6$, 400 MHz): 10.75 (s, 1H), 9.15 (s, 1H), 8.90 (s, 1H), 7.83 (d, J 8.8, 2H), 7.58 (d, J 8.8, 2H), 5.80 (s, 1H), 2.59 (s, 3H), 1.90-1.78 (m, 2H), 0.99-0.82 (m, 4H), 0.70-0.58 (m, 4H). MS (m/z): 359.99 [M+H]$^+$.

Example 19

N-[4-(3,5-dicyclopropyl-1H-pyrazol-1-yl)phenyl]-2-phenylacetamide

Following the general procedure-1, title compound (100 mg) was prepared from 2-phenylacetic acid (68 mg, 0.501 mmol) and intermediate 27 (100 mg, 0.41 mmols) as a pale yellow solid. M. P. 133-138.5° C. $^1$H-NMR (δ ppm, DMSO-d$_6$, 400 MHz): 10.30 (s, 1H), 7.69 (d, J 8.8, 2H), 7.48 (d, J 8.8, 2H), 7.35-7.30 (m, 4H), 7.26-7.22 (m, 1H), 5.77 (s, 1H), 3.65 (s, 2H), 1.84-1.70 (m, 2H), 0.90-0.80 (m, 4H), 0.65-0.59 (m, 4H). MS (m/z): 358.29 [M+H]$^+$.

Example 20

N-[4-(3,5-dicyclopropyl-1H-pyrazol-1-yl)phenyl]-2-(4-fluorophenyl)acetamide

Following the general procedure-1, the title compound (120 mg) was prepared from 2-(4-fluorophenyl)acetic acid (92 mg, 0.60 mmol) and intermediate 27 (120 mg, 0.60 mmol) as an off-white solid. M. P. 141-148° C. $^1$H-NMR (δ ppm, DMSO-d$_6$, 400 MHz): 10.30 (s, 1H), 7.68 (d, J 8.8, 2H), 7.48 (d, J 8.8, 2H), 7.38-7.34 (m, 2H), 7.14 (t, J 8.9, 2H), 5.77 (s, 2H), 1.84-1.70 (m, 2H), 0.89-0.80 (m, 4H), 0.65-0.59 (m, 4H). MS (m/z): 374.1 [M–H]$^-$.

Example 21

N-[4-(3,5-dicyclopropyl-1H-pyrazol-1-yl)phenyl]-1-phenylcyclopropanecarboxamide

Following the general procedure-2, the title compound (40 mg) was prepared from 1-phenylcyclopropanecarbonyl chloride (82 mg, 0.45 mmol) and intermediate 27 (100 mg, 0.42 mmol) as a brown viscous liquid. $^1$H-NMR (δ ppm, DMSO-d$_6$, 400 MHz): 9.24 (s, 1H), 7.65 (d, J 8.9, 2H), 7.45 (d, J 8.9, 2H), 7.42-7.33 (m, 4H), 7.28 (d, J 7.0, 1H), 5.76 (s, 1H), 1.83-1.79 (m, 1H), 1.75-1.70 (m, 1H), 1.46-1.41 (m, 2H), 1.31-1.10 (m, 2H), 0.89-0.79 (m, 4H), 0.65-0.59 (m, 4H). MS (m/z): 384.27 [M+H]$^+$.

Example 22

N-[4-(3,5-dicyclopropyl-1H-pyrazol-1-yl)phenyl]-2-(pyridin-2-yl)acetamide hydrochloride Following the general procedure-1, N-[4-(3,5-dicyclopropyl-1H-pyrazol-1-yl)phenyl]-2-(pyridin-2-yl)acetamide (85 mg) was prepared from 2-pyridylacetic acid (139 mg, 0.8 mmol) and intermediate 27 (120 mg, 0.5 mmol) as a pale yellow solid and dissolved in THF. Saturated HCl in diethyl ether was added to this solution at 0° C. and stirred for 15 min. Solid that separated out was filtered and dried to give the title compound (75 mg) as a pale yellow solid. M. P. 157-162° C. $^1$H-NMR (δ ppm, DMSO-d$_6$, 400 MHz): 10.90 (s, 1H), 8.89 (d, J 5.1, 1H), 8.53 (t, J 8.0, 1H), 8.05 (d, J 8.0, 1H), 7.95 (t, J 6.5, 1H), 7.72 (d, J 8.8, 2H), 7.52 (d, J 8.8, 2H), 5.79 (s, 1H), 4.34 (s, 2H), 1.87-1.70 (m, 2H), 0.95-0.81 (m, 4H), 0.67-0.59 (in, 4H). MS (m/z): 359.29 [M+H-HCl]$^+$.

Example 23

N-[4-(3,5-dicyclopropyl-1H-pyrazol-1-yl)phenyl]-2-(pyridin-3-yl)acetamide hydrochloride Following the general procedure-1, N-[4-(3,5-dicyclopropyl-1H-pyrazol-1-yl)phenyl]-2-(pyridin-3-yl)acetamide (86 mg) was prepared from 3-pyridylacetic acid (139 mg, 0.8 mmol) and intermediate 27 (120 mg, 0.5 mmol) as a pale yellow solid and dissolved in THF. Saturated HCl in diethyl ether was added to this solution at 0° C. and stirred for 15 min. Solid that separated out was filtered and dried to give the title compound (75 mg) as a pale yellow solid. M. P. 103-108° C. $^1$H-NMR (δ ppm, DMSO-d$_6$, 400 MHz): 10.71 (s, 1H), 8.92 (s, 1H), 8.84 (d, J 5.1, 1H), 8.55 (d, J 7.8, 1H), 8.06-8.01 (m, 1H), 7.72 (d, J 8.8, 2H), 7.51 (d, J 8.8, 2H), 5.78 (s, 1H), 4.05 (s, 2H), 1.85-1.69 (m, 2H), 0.91-0.79 (m, 4H), 0.68-0.58 (m, 4H). MS (m/z): 393.05 [M−H]$^-$.

Example 24

N-[4-(3,5-dicyclopropyl-1H-pyrazol-1-yl)phenyl]-2-(pyridin-4-yl)acetamide hydrochloride Following the general procedure-1, N-[4-(3,5-dicyclopropyl-1H-pyrazol-1-yl)phenyl]-2-(pyridin-4-yl)acetamide (89 mg) was prepared from 2-(pyridin-4-yl)acetic acid (104 mg, 0.60 mmol) and intermediate 27 (120 mg, 0.50 mmol) as an off-white solid. This amide was dissolved in saturated HCl in diethyl ether at 0° C. and stirred for 15 min. Solid that separated out was filtered and dried to give the title compound (12 mg). M. P. 175-181° C. $^1$H-NMR (δ ppm, DMSO-d$_6$, 400 MHz): 10.75 (s, 1H), 8.86 (d, J 6.2, 2H), 8.04 (d, J 5.8, 2H), 7.71 (d, J 8.8, 2H), 7.51 (d, J 8.8, 2H), 5.78 (s, 1H), 4.12 (s, 2H), 1.84-1.72 (m, 2H), 0.91-0.80 (m, 4H), 0.66-0.60 (m, 4H). MS (m/z): 393.09 [M−H]$^-$ Example 25

N-[4-(3,5-dicyclopropyl-1H-pyrazol-1-yl)phenyl]-2-(piperazin-1-yl)acetamide hydrochloride Intermediate 41 (150 mg, 0.475 mmol) and piperazine (40 mg, 0.464 mmol) were dissolved in DMF (3 mL) at 0° C. and Sodium Hydride (30 mg, 1.25 mmol) was added to the reaction mixture. Then reaction was allowed to stir at ambient temperature overnight. Work-up (H$_2$O:AcOEt) followed by purification on column afforded both mono and di substituted piperazines. They were separated by column chromatography. Mono substituted piperazine was protected with di-tert-butyl dicarbonate (100 mg, 0.46 mmol) in presence of tri ethyl amine (0.11 ml, 0.82 mmol) in DCM. Work up followed by purification afforded the tert-butyl 4-(2-(4-(3,5-dicyclopropyl-1H-pyrazol-1-yl)phenylamino)-2-oxoethyl)piperazine-1-carboxylate (98 mg). Saturated HCl in diethyl ether was added at 0° C. to it and stirred for 15 min. Solid that separated out was filtered and dried to give the title compound (40 mg) as an off-white solid. M. P. 218-226° C. $^1$H-NMR (δ ppm, DMSO-d$_6$, 400 MHz): 10.99 (bs, 1H), 9.69 (bs, 2H), 7.74 (d, J 8.7, 2H), 7.56 (d, J 8.7, 2H), 4.20 (bs, 21H), 3.54 (bs, 2H), 3.41 (bs, 2H), 1.80-1.71 (m, 2H), 0.97-0.80 (m, 4H), 0.69-0.60 (m, 4H). MS (m/z): 393.05 [M+H−HCl]$^+$.

Example 26

N-[4-(3,5-dicyclopropyl-1H-pyrazol-1-yl)phenyl]-2-morpholinoacetamide

Intermediate 41 (150 mg, 0.475 mmol) and morpholine (40 mg, 0.475 mmol) were dissolved in DMF (3 mL) at 0° C. and Sodium Hydride (30 mg, 1.25 mmol) was added to the reaction mixture. Reaction was allowed to stir at ambient temperature overnight. Work-up (H$_2$O:AcOEt) followed by purification on column afforded the title compound as a white solid, M. P. 178-184° C. $^1$H-NMR (δ ppm, DMSO-d$_6$, 400 MHz): 9.87 (s, 1H), 7.74 (d, J 8.7, 2H), 7.49 (d, J 8.7, 2H), 5.77 (s, 1H), 3.63 (t, J 4.2, 4H), 3.13 (s, 2H), 2.48-2.45 (m, 4H), 1.89-1.69 (m, 2H), 0.92-0.81 (m, 4H), 0.69-0.60 (m, 4H). MS (m/z): 367.32 [M+H]$^+$.

Example 27

N-[4-(3,5-dicyclopropyl-1H-pyrazol-1-yl)phenyl]benzenesulfonamide

Following the general procedure-2, title compound (90 mg) was prepared from benzene sulphonyl chloride (81 mg, 0.458 mmol) and intermediate 27 (100 mg, 0.42 mmol) as a yellow solid. M. P 180-184.5° C. $^1$H-NMR (δ ppm, DMSO-d$_6$, 400 MHz): 10.43 (s, 1H), 7.77 (d, J 7.2, 2H), 7.64-7.59 (m, 1H), 7.58-7.52 (m, 2H), 7.43 (d, J 8.7, 2H), 7.17 (d, J 8.7, 2H), 5.75 (s, 1H), 1.81-1.75 (m, 1H), 1.69-1.64 (m, 1H), 1.16-0.78 (m, 4H), 0.62-0.57 (m, 4H). MS (m/z): 378.05 [M−H]$^-$.

Example 28

N-[4-(3,5-dicyclopropyl-1H-pyrazol-1-yl)-3-fluorophenyl]-4-methyl-1,2,3-thiadiazole-5-carboxamide Following the general procedure-2, the title compound (34 mg) was prepared from 4-methyl-1,2,3-thiadiazole-5-carbonyl chloride (90 mg, 0.56 mmol) and intermediate 28 (120 mg, 0.47 mmol) as a white solid. M.P.: 148-152° C. $^1$H-NMR (δ ppm, DMSO-d$_6$, 400 MHz): 11.07 (s, 1H), 7.83 (d, J 10.8, 1H), 7.57-7.50 (m, 2H), 5.76 (s, 1H), 2.82 (s, 3H), 1.87-1.79 (m, 1H), 1.56-1.48 (m, 1H), 0.89-0.77 (m, 4H), 0.66-0.54 (m, 4H). MS (m/z): 384.28 [M+H]$^+$.

Example 29

N-[4-(3,5-dicyclopropyl-1H-pyrazol-1-yl)-3-fluorophenyl]-4-methylthiazole-5-carboxamide Following the general procedure-1, the title compound (48 mg) was prepared from 4-methylthiazole-5-carboxylic acid (106 mg, 0.75 mmol) and intermediate 28 (120 mg, 0.47 mmol) as a pale-yellow solid. M.P.: 102-106° C. $^1$H-NMR (δ ppm, DMSO-d$_6$, 400 MHz): 10.58 (s, 1H), 9.16 (s, 1H), 7.83 (dd, J 2.2, 12.6, 1H), 7.57 (dd, J 1.9, 8.8, 1H), 7.48 (t, J 8.6, 1H), 5.75 (s, 1H), 2.62 (s, 3H), 1.85-1.79 (m, 1H), 1.55-1.45 (m, 1H), 0.90-0.77 (m, 4H), 0.68-0.55 (m, 4H). MS (m/z): 383.05 [M+H]$^+$.

Example 30

N-[4-(3,5-dicyclopropyl-1H-pyrazol-1-yl)-3-fluorophenyl]-3,5-dimethylisoxazole-4-carboxamide Following the general procedure-2, the title compound (70 mg) was prepared from intermediate 28 (200 mg, 0.78 mmol) and 3,5-dimethylisoxazole-4-carboxylic acid (150 mg, 0.95 mmol) as a pale-yellow solid. M.P.: 166-168° C. $^1$H-NMR (δ ppm, DMSO-d$_6$, 400 MHz): 10.40 (s, 1H), 7.84-7.81 (m, 1H), 7.52-7.46 (m, 2H), 5.74 (s, 1H), 2.58 (s, 3H), 2.31 (s, 3H), 1.88-1.79 (m, 1H), 1.54-1.46 (m, 1H), 0.90-0.78 (m, 4H), 0.64-0.55 (m, 4H). MS (m/z): 381.32 [M+H]$^+$.

Example 31

N-[4-(3,5-dicyclopropyl-1H-pyrazol-1-yl)-3-fluorophenyl]-2-methyl benzamide

Following the general procedure-2, the title compound (25 mg) was prepared from intermediate 28 (200 mg, 0.78 mmol) and o-toluic acid (143 mg, 0.93 mmol) as a yellow solid. M.P.: 105-107° C. $^1$H-NMR (δ ppm, DMSO-$d_6$, 400 MHz): 10.67 (s, 1H), 7.92 (d, J 11.4, 1H), 7.59 (d, J 8, 1H), 7.52-7.47 (m, 2H), 7.46-7.38 (m, 2H), 7.32 (d, J 7.4, 2H), 5.74 (s, 1H), 2.39 (s, 3H), 1.90-1.80 (m, 1H), 1.59-1.50 (m, 1H), 0.90-0.78 (m, 4H), 0.68-0.54 (m, 4H). MS (m/z): 375.86 [M+H]$^+$.

Example 32

N-[4-(3,5-dicyclopropyl-1H-pyrazol-1-yl)-3-fluorophenyl]-2,3-difluorobenzamide

Following the general procedure-1, the title compound (50 mg) was prepared from intermediate 28 (200 mg, 0.77 mmol) and 2,3-difluorobenzoic acid (196 mg, 1.24 mmol) as a pale-yellow solid. M.P.: 132-135° C. $^1$H-NMR (δ ppm, DMSO-$d_6$, 400 MHz): 10.93 (s, 1H), 7.87 (d, J 10.8, 1H), 7.65 (q, J 8.3, 1H), 7.59-7.48 (m, 3H), 7.41-7.34 (m, 1H), 5.75 (s, 1H), 1.88-1.79 (m, 1H), 1.56-1.48 ((m, 1H), 0.90-0.78 (m, 4H), 0.65-0.55 (m, 4H). MS (m/z): 396.16 [M−H]$^-$.

Example 33

N-[4-(3,5-dicyclopropyl-1H-pyrazol-1-yl)-3-fluorophenyl]-2,6-difluorobenzamide

Following the general procedure-1, the title compound (50 mg) was prepared from intermediate 28 (200 mg, 0.78 mmol) and 2,6-difluorobenzoic acid (196 mg, 1.2 mmol) as a yellow solid. M.P.: 182.2-185.7° C. $^1$H-NMR (δ ppm, DMSO-$d_6$, 400 MHz): 11.20 (s, 1H), 7.84 (d, J 11.4, 1H), 7.68-7.59 (m, 1H), 7.59-7.50 (m, 2H), 7.28 (t, J 8, 2H), 5.75 (s, 1H), 1.89-1.79 (m, 1H), 1.60-1.50 (m, 1H), 0.90-0.78 (m, 4H), 0.66-0.58 (m, 4H). MS (m/z): 398.07 [M+H]$^+$.

Example 34

N-[4-(3,5-dicyclopropyl-1H-pyrazol-1-yl)-3-fluorophenyl]nicotinamide hydrochloride Following the general procedure-1, N-[4-(3,5-dicyclopropyl-1H-pyrazol-1-yl)-3-fluorophenyl]nicotinamide (130 mg) was prepared from intermediate 28 (200 mg, 0.78 mmol) and nicotinic acid (153 mg, 1.2 mmol) as an off-white solid and dissolved in THF. Saturated HCl in diethyl ether was added to this solution at 0° C. and stirred for 15 min. Solid that separated out was filtered and dried to give the title compound (70 mg) as a white solid. M.P.: 201.2-203.4° C., $^1$H-NMR (δ ppm, DMSO-$d_6$, 400 MHz): 11.04 (s, 1H), 9.26 (s, 1H), 8.87 (d, J 4.8, 1H), 8.58 (d, J 4.8, 1H), 7.97 (d, J 12.8, 1H), 7.81 (d, J 5, 1H), 7.71 (d, J 8.6, 1H), 7.52 (t, J 8.7, 1H), 5.76 (s, 1H), 1.90-1.80 (m, 1H), 1.58-1.48 (m, 1H), 0.90-0.78 (m, 4H), 0.65-0.55 (m, 4H). MS (nm/z): 363.14 [M+H−HCl]$^+$.

Example 35

N-[4-(3,5-dicyclopropyl-1H-pyrazol-1-yl)-3-fluorophenyl]isonicotinamide hydrochloride Following the general procedure-1, N-[4-(3,5-dicyclopropyl-1H-pyrazol-1-yl)-3-fluorophenyl]isonicotinamide (107 mg) was prepared from intermediate 28 (200 mg, 0.78 mmol) and isonicotinic acid (153 mg, 1.2 mmol) as a yellow solid and dissolved in THF. Saturated HCl in diethyl ether was added to this solution at 0° C. and stirred for 15 min. Solid that separated out was filtered and dried to give the title compound (70 mg) as a pale-yellow solid. M.P.: 201.2-203.4° C. $^1$H-NMR (δ ppm, DMSO-$d_6$, 400 MHz): 10.83 (s, 1H), 8.81 (d, J 5.9, 2H), 7.94 (dd, J 1.9, 12.6, 1H), 7.87 (d, J 5.9, 2H), 7.67 (dd, J 1.4, 8.6, 1H), 7.51 (t, J 8.7, 1H), 5.76 (s, 1H), 1.88-1.78 (m, 1H), 1.58-1.48 (m, 1H), 0.88-0.78 (m, 4H), 0.62-0.50 (m, 4H). MS (m/z): 363.14 [M+H−HCl]$^+$.

Example 36

N-[4-(3,5-dicyclopropyl-1H-pyrazol-1-yl)-3-fluorophenyl]-4-methylpyrimidine-5-carboxamide Following the general procedure-1, the title compound (44 mg) was prepared from 4-methylpyrimidine-5-carboxylic acid (144 mg, 0.75 mmol) and intermediate 28 (120 mg, 0.47 mmol) as a pale-brown solid M.P.: 123-125° C. $^1$H-NMR (δ ppm, DMSO-$d_6$, 400 MHz): 11.00 (s, 1H), 9.16 (s, 1H), 8.93 (s, 1H), 7.91-7.87 (m, 1H), 7.60-7.47 (m, 2H) 5.75 (s, 1H), 2.6 (s, 3H), 1.90-1.78 (m, 1H), 1.66-1.56 (m, 1H), 0.90-0.78 (m, 4H), 0.67-0.59 (m, 4H). MS (m/z): 377.86 [M+H]$^+$.

Example 37

N-[4-(4-chloro-3,5-dicyclopropyl-1H-pyrazol-1-yl)-3-fluorophenyl]-4-methyl-1,2,3-thiadiazole-5-carboxamide Following the general procedure-2, the title compound (43 mg) was prepared from 4-methyl-1,2,3-thiadiazole-5-carbonyl chloride (80 mg, 0.49 mmol) and intermediate 29 (120 mg, 0.41 mmol) as a white solid. M.P.: 153-156° C. $^1$H-NMR (δ ppm, DMSO-$d_6$, 400 MHz): 11.09 (s, 1H), 7.84 (d, J 12, 1H), 7.58-7.49 (m, 2H), 2.82 (s, 3H), 1.89-1.81 (m, 1H), 1.69-1.61 (m, 1H), 0.92-0.85 (m, 2H), 0.82-0.72 (m, 4H), 0.64-0.55 (m, 2H). MS (m/z): 415.57 [M−H]$^-$.

Example 38

N-[6-(3,5-dicyclopropyl-1H-pyrazol-1-yl)pyridin-3-yl]-4-methyl-1,2,3-thiadiazole-5-carboxamide hydrochloride Following the general procedure-1, the title compound (32 mg) was prepared from 4-methyl-1,2,3-thiadiazole-5-carboxylic acid (80 mg, 0.47 mmol) and intermediate 30 (120 mg, 0.40 mmol) as a white solid. M.P.: 215-219° C. $^1$H-NMR (δ ppm, DMSO-$d_6$, 400 MHz): 11.09 (s, 1H), 8.74 (d, J 2.2, 1H), 8.24 (dd, J 2.4, 8.8, 1H), 7.77 (d, J 8.8, 1H), 5.83 (s, 1H), 3.87 (s, 3H), 2.70-2.61 (m, 1H), 1.90-1.81 (m, 1H), 0.95-0.82 (m, 4H), 0.70-0.58 (m, 4H). MS (m/z): 365.03 [M−H−HCl]$^-$.

Example 39

N-[6-(3,5-dicyclopropyl-1H-pyrazol-1-yl)pyridin-3-yl]-4-methylthiazole-5-carboxamide hydrochloride Following the general procedure-1, N-[6-(3,5-dicyclopropyl-1H-pyrazol-1-yl)pyridin-3-yl]-4-methylthiazole-5-carboxamide (55 mg) was prepared from 4-methylthiazole-5-carboxylic acid (130 mg, 0.83 mmol) and intermediate 30

(200 mg, 0.83 mmol) as a brown solid and dissolved in THF. Saturated HCl in diethyl ether was added to this solution at 0° C. and stirred for 15 min. Solid that separated out was filtered and dried to give the title compound (50 mg) as an off-white solid. M. P. 93-98° C. $^1$H-NMR (δ ppm, DMSO-$d_6$, 400 MHz): 10.57 (s, 1H), 9.16 (s, 1H), 8.74 (s, 1H), 8.23 (dd, J 2.4, 8.9, 1H), 7.73 (d, J 8.9, 1H), 5.82 (s, 1H), 2.70-2.60 (m, 4H), 1.88-1.80 (m, 1H), 0.93-0.81 (m, 4H), 0.69-0.58 (m, 4H). MS (m/z): 366.36 [M+H−HCl]$^+$.

Example 40

N-[6-(3,5-dicyclopropyl-1H-pyrazol-1-yl)pyridin-3-yl]-2,4-dimethylthiazole-5-carboxamide Following the general procedure-1, title compound (48 mg) was prepared from 2,4-dimethylthiazole-5-carboxylic acid (94 mg, 0.59 mmol) and intermediate 30 (120 mg, 0.49 mmol) as a pale yellow solid M. P. 108-113° C. $^1$H-NMR (δ ppm, DMSO-$d_6$, 400 MHz): 10.38 (s, 1H), 8.71 (d, J 2.0, 1H), 8.20 (dd, J 2.0, 8.8, 1H), 7.71 (d, J 8.8, 1H), 5.81 (s, 1H), 2.66 (s, 3H), 2.64-2.58 (m, 1H), 2.56 (s, 3H), 1.89-1.81 (m, 1H), 0.92-0.84 (m, 4H), 0.67-0.59 (m, 4H). MS (m/z): 380.23 [M+H−HCl]$^+$.

Example 41

N-[6-(3,5-dicyclopropyl-1H-pyrazol-1-yl)pyridin-3-yl]-3,5-dimethylisoxazole-4-carboxamide Following the general procedure-1, the title compound (68 mg) was prepared from 3,5-dimethylisoxazole-4-carboxylic acid (112 mg, 0.8 mmol) and intermediate 30 (120 mg, 0.5 mmol) as a pale-yellow solid M.P.: 208-210° C. $^1$H-NMR (δ ppm, DMSO-$d_6$, 400 MHz): 10.32 (s, 1H), 8.70 (d, J 2.5, 8.8, 1H), 8.20 (dd, J 2.5, 8.8, 1H), 7.73 (d, J 8.8, 1H), 5.82 (s, 1H), 2.67-2.59 (m, 1H), 2.57 (s, 3H), 2.34 (s, 3H), 1.90-1.81 (m, 1H), 0.94-0.82 (m, 4H), 0.69-0.58 (m, 4H). MS (n/z): 361.74 [M−H]$^-$.

Example 42

6-(3,5-dicyclopropyl-1H-pyrazol-1-yl)-N-o-tolylnicotinamide

Following the general procedure-2, the title compound (10 mg) was prepared from o-toluidine (60 mg, 0.56 mmol) and intermediate 30 (177 mg, 0.62 mmol) as a white solid. M.P.: 123-126° C. $^1$H-NMR (δ ppm, DMSO-$d_6$, 400 MHz): 10.05 (s, 1H), 9.00 (s, 1H), 8.44 (d, J 8.2, 1H), 7.92 (d, J 8.6, 1H), 7.36 (d, J 7.6, 2H), 7.28 (d, J 7.5, 1H), 7.26-7.19 (m, 1H), 5.92 (s, 1H), 2.89-2.81 (m, 1H), 2.25 (s, 3H), 1.94-1.84 (m, 1H), 1.00-0.87 (m, 4H), 0.74-0.62 (m, 4H). MS (m/z): 357.02 [M−H]$^-$.

Example 43

N-[6-(3,5-dicyclopropyl-1H-pyrazol-1-yl)pyridin-3-yl]-2-fluorobenzamide

Following the general procedure-1, the title compound (121 mg) was prepared from 2-fluorobenzoic acid (111 mg, 0.8 mmol) and intermediate 30 (120 mg, 0.5 mmol) as a pale-yellow solid M.P.: 121-126° C. $^1$H-NMR (δ ppm, DMSO-$d_6$, 400 MHz): 10.75 (s, 1H), 8.76 (d, J 2.4, 1H), 8.28 (dd, J 2.6, 8.9, 1H), 7.79-7.70 (m, 2H), 7.65-7.54 (m, 1H), 7.42-7.30 (m, 2H), 5.82 (s, 1H), 2.71-2.60 (m, 1H), 1.94-1.80 (m, 1H), 0.94-0.80 (m, 4H), 0.72-0.59 (m, 4H). MS (m/z): 362.95 [M+H]$^+$.

Example 44

N-[6-(3,5-dicyclopropyl-1H-pyrazol-1-yl)pyridin-3-yl]-2,3-difluorobenzamide hydrochloride Following the general procedure-1, title compound (68 mg) was prepared from 2,3-difluorobenzoic acid (126 mg, 0.5 mmol) and intermediate 30 (120 mg, 0.5 mmol) as a pale yellow solid M. P. 172-177° C. $^1$H-NMR (δ ppm, DMSO-$d_6$, 400 MHz): $^1$H-NMR (δ ppm, DMSO-$d_6$, 400 MHz): 10.84 (s, 1H), 8.75 (d, J 1, 1H), 8.26 (dd, J 1, 8.8, 1H), 7.75 (d, J 8.8, 1H), 7.64 (q, J 8.3, 1H), 7.53 (t, J 6.6, 1H), 7.35 (q, J 7.5, 1H), 5.82 (s, 1H), 2.70-2.61 (m, 1H), 1.91-1.80 (m, 1H), 0.99-0.81 (m, 4H), 0.69-0.52 (m, 4H). MS (m/z): 378.88 [M−H−HCl]$^-$.

Example 45

N-[6-(3,5-dicyclopropyl-1H-pyrazol-1-yl)pyridin-3-yl]-2,6-difluorobenzamide hydrochloride Following the general procedure-1, N-[6-(3,5-dicyclopropyl-1H-pyrazol-1-yl)pyridin-3-yl]-2,6-difluorobenzamide (71 mg) was prepared from 2,6-difluorobenzoic acid (126 mg, 0.799 mmol) and intermediate 30 (120 mg, 0.5 mmol) as a brown solid and dissolved in THF. Saturated HCl in diethyl ether was added to this solution at 0° C. and stirred for 15 min. Solid that separated out was filtered and dried to give the title compound (69 mg) as a brown solid. M. P. 196-201° C. $^1$H-NMR (δ ppm, DMSO-$d_6$, 400 MHz): 11.16 (s, 1H), 8.72 (d, J 2.3, 1H), 8.26 (dd, J 2.5, 8.9, 1H), 7.75 (d, J 8.8, 1H), 7.65-7.60 (m, 1H), 7.27 (t, J 8.0, 2H), 5.82 (s, 1H), 2.69-2.60 (m, 1H), 1.90-1.82 (m, 1H), 0.94-0.82 (m, 4H), 0.70-0.59 (m, 4H). MS (m/z): [M+H−HCl]$^+$.

Example 46

N-[6-(3,5-dicyclopropyl-1H-pyrazol-1-yl)pyridin-3-yl]nicotinamide dihydrochloride Following the general procedure-1, N-[6-(3,5-dicyclopropyl-1H-pyrazol-1-yl)pyridin-3-yl]nicotinamide (82 mg) was prepared from intermediate 30 (120 mg, 0.5 mmol) and nicotinic acid (98 mg, 0.65 mmol) as a yellow solid and dissolved in THF. Saturated HCl in diethyl ether was added to this solution at 0° C. and stirred for 15 min. Solid that separated out was filtered and dried to give the title compound (80 mg) as an yellow solid. M.P.: 164.6-169.5° C. $^1$H-NMR (δ ppm, DMSO-$d_6$, 400 MHz): 11.19 (s, 1H), 9.36 (s, 1H), 8.95 (d, J 5.2, 1H), 8.88 (d, J 2.5, 1H), 8.75 (d, J 8, 1H), 8.36 (dd, J 2.5, 8.9, 1H), 7.92 (dd, J 5.3, 8, 1H), 7.77 (d, J 8.9, 1H), 5.83 (s, 1H), 2.71-2.61 (m, 1H), 1.91-1.81 (m, 1H), 0.95-0.82 (m, 4H), 0.70-0.55 (m, 4H). MS (m/z): 346.27 [M−2HCl]$^-$.

Example 47

N-[6-(3,5-dicyclopropyl-1H-pyrazol-1-yl)pyridin-3-yl]isonicotinamide dihydrochloride Following the general procedure-1, N-[6-(3,5-dicyclopropyl-1H-pyrazol-1-yl)pyridin-3-yl]isonicotinamide (220 mg) from intermediate 30 (200 mg, 0.83 mmol) and isonicotinic acid (163 mg, 1.3 mmol) as a pale-yellow solid and dissolved in THF. Saturated HCl in diethyl ether was added to this solution at 0° C. and stirred for 15 min. Solid that separated out was filtered and dried to give the title compound (190 mg) as a pale-yellow solid. M.P.: 200.3-202.4° C. $^1$H-NMR (δ ppm, DMSO-$d_6$, 400 MHz): 11.26 (s, 1H), 8.99 (t, J 5.4, 2H), 8.88 (s, 1H), 8.35 (dd, J 2.6, 6.3, 1H), 8.30-8.25 (m, 21H), 7.78 (d, J 8.9, 1H), 5.83 (s, 1H), 2.72-2.62 (m, 1H), 1.90-1.81 (m, 1H), 0.94-0.82 (m, 4H), 0.70-0.59 (m, 4H). MS (m/z): 346.13 [M+H–2HCl]$^+$.

Example 48

N-[6-(3,5-dicyclopropyl-1H-pyrazol-1-yl)pyridin-3-yl]-3-fluoroisonicotinamide

Following the general procedure-1, the title compound (97 mg) was prepared from intermediate 30 (120 mg, 0.5 mmol) and 3-fluoroisonicotinic acid (112 mg, 0.8 mmol) as a brown solid. M.P.: 192.3-195.4° C. $^1$H-NMR (δ ppm, DMSO-$d_6$, 400 MHz): 11.00 (s, 1H), 8.79 (s, 1H), 8.74 (d, J 2.5, 1H), 8.61 (d, J 4.8, 1H), 8.26 (dd, J 2.8, 8.9, 1H), 7.78-7.72 (m, 2H), 5.83 (s, 1H), 2.61-2.51 (m, 1H), 1.90-1.80 (m, 1H), 0.94-0.82 (m, 4H), 0.70-0.58 (m, 4H). MS (m/z): 364.19 [M+H]$^+$.

Example 49

3,5-dichloro-N-{4-[5-cyclopropyl-3-(trifluoromethyl)-1H-pyrazol-1-yl]phenyl}isonicotinamide Following the general procedure-2, the title compound (60 mg) was prepared from 3,5-dichloroisonicotinoyl chloride (313 mg, 1.5 mmol) and intermediate 31 (200 mg, 0.75 mmol) as a white solid. M.P.: 182-184° C. $^1$H-NMR (δ ppm, DMSO-$d_6$, 400 MHz): 11.21 (s, 1H), 8.82 (s, 2H), 7.85 (d, J 8.8, 2H), 7.65 (d, J 8.8, 2H), 6.62 (s, 1H), 1.90-1.80 (m, 1H), 1.00-0.91 (m, 2H), 0.78-0.85 (m, 2H). MS (m/z): 371.76 [M–H–2Cl]$^-$.

Example 50

3,5-dichloro-N-[6-(3,5-dicyclopropyl-1H-pyrazol-1-yl)pyridin-3-yl]isonicotinamide hydrochloride Following the general procedure-2,3,5-dichloro-N-[6-(3,5-dicyclopropyl-1H-pyrazol-1-yl)pyridin-3-yl]isonicotinamide (24 mg) was prepared from 3,5-dichloroisonicotinoyl chloride (313 mg, 1.5 mmol) and intermediate 30 (200 mg, 0.75 mmol) as a white solid and dissolved in THF. Saturated HCl in diethyl ether was added to this solution at 0° C. and stirred for 15 min. Solid that separated out was filtered and dried to give the title compound (7 mg) as a pale-yellow solid. M.P.: 193-195° C. $^1$H-NMR (δ ppm, DMSO-$d_6$, 400 MHz): 11.34 (s, 1H), 8.82 (s, 2H), 8.69 (d, J 2.4, 1H), 8.24 (dd, J 2.6, 8.9, 1H), 7.78 (d, J 8.9, 1H), 5.83 (s, 1H), 2.72-2.64 (m, 1H), 1.80-1.70 (m, 1H), 0.92-0.82 (m, 4H), 0.70-0.58 (m, 4H). MS (m/z): 413.40 [M–H–HCl]$^+$.

Example 51

N-[6-(3,5-dicyclopropyl-1H-pyrazol-1-yl)pyridin-3-yl]-4-methylpyrimidine-5-carboxamide hydrochloride Following the general procedure-1, N-[6-(3,5-dicyclopropyl-1H-pyrazol-1-yl)pyridin-3-yl]-4-methylpyrimidine-5-carboxamide (230 mg) from intermediate 30 (200 mg, 0.83 mmol) and intermediate 53 (350 mg, 2.49 mmol) as a pale yellow solid and dissolved in THF. Saturated HCl in diethyl ether was added to this solution at 0° C. and stirred for 15 min. Solid that separated out was filtered and dried to give the title compound (120 mg) as a yellow solid. M.P.: 192-197° C. $^1$H-NMR (δ ppm, DMSO-$d_6$, 400 MHz): 10.92 (s, 1H), 9.16 (s, 1H), 8.94 (s, 1H), 8.75 (d, J 2.5, 1H), 8.27 (dd, J 2.6, 8.8, 1H), 7.76 (d, J 8.8, 1H), 5.82 (s, 1H), 2.70-2.62 (m, 1H), 2.61 (s, 3H), 1.92-1.84 (m, 1H), 0.95-0.85 (m, 4H), 0.70-0.58 (m, 4H). MS (m/z): 360.97 [M+H–HCl]$^+$.

Example 52

N-{4-[5-cyclopropyl-3-(trifluoromethyl)-1H-pyrazol-1-yl]phenyl}-4-methyl-1,2,3-thiadiazole-5-carboxamide Following the general procedure-2, the title compound (15 mg) was prepared from 4-methyl-1,2,3-thiadiazole-5-carbonyl chloride (80 mg, 0.49 mmol) and intermediate 31 (120 mg, 0.45 mmol) as a white solid. M. P. 84-89° C. $^1$H-NMR (δ ppm, DMSO-$d_6$, 400 MHz): 10.95 (s, 1H), 7.87 (d, J 8.8, 2H), 7.66 (d, J 8.8, 2H), 6.62 (s, 1H), 2.82 (s, 3H), 1.85-1.81 (m, 1H), 0.99-0.94 (m, 2H), 0.86-0.79 (m, 2H). MS (m/z): 392.08 [M–H]$^-$.

Example 53

N-{4-[5-cyclopropyl-3-(trifluoromethyl)-1H-pyrazol-1-yl]phenyl}-4-methylthiazole-5-carboxamide Following the general procedure-2, the title compound (20 mg) was prepared from 4-methylthiazole-5-carbonyl chloride (78 mg) and intermediate 31 (120 mg, 0.45 mmol) as brown solid. M. P. 137-141° C. $^1$H-NMR (δ ppm, DMSO-$d_6$, 400 MHz): 10.47 (s, 1H), 9.14 (s, 1H), 7.87 (d, J 8.8, 2H), 7.62 (d, J 8.8, 2H), 6.61 (s, 1H), 2.62 (s, 3H), 1.85-1.81 (m, 1H), 0.99-0.94 (m, 2H), 0.88-0.83 (m, 2H). MS (m/z): 391.15 [M–H]$^-$.

Example 54

N-{4-[5-cyclopropyl-3-(trifluoromethyl)-1H-pyrazol-1-yl]phenyl}-N,4-dimethylthiazole-5-carboxamide N-{4-[3-cyclopropyl-5-(trifluoromethyl)-1H-pyrazol-1-yl]phenyl}-4-methylthiazole-5-carboxamide (500 mg, 1.27 mmol) was dissolved in THF, cooled to 0° C. and added sodium hydride (61 mg, 2.54 mmol) and stirred the mixture for 30 mins at the same temperature. Methyl Iodide (210 mg, 1.52 mmol) was added and heated the reaction mixture to rt. After 3h, reaction mixture quenched with water. Work up($H_2O$/AcOEt) and purification afforded the title compound (150 mg) as a gummy liquid. $^1$H-NMR (δ ppm, CDCl$_3$, 400 MHz): 8.59 (s, 1H), 7.63 (d, J 8.6, 2H), 7.27 (d, J 8.6, 2H), 6.26 (s, 1H), 3.53 (s, 3H), 2.56 (s, 3H), 1.82-1.72 (m, 1H), 1.10-1.00 (m, 2H), 0.81-0.75 (m, 2H). MS (m/z): 406.96 [M+H]$^+$.

Example 55

N-{4-[5-cyclopropyl-3-(trifluoromethyl)-1H-pyrazol-1-yl]phenyl}-2,4-dimethylthiazole-5-carboxamide Following the general procedure-1, the title compound (58 mg) was prepared from 2,4-dimethylthiazole-5-carboxylic acid (77 mg, 0.49 mmol) and intermediate 31 (120 mg, 0.45 mmol) as an off-white solid. M. P. 117-122° C. $^1$H-NMR (δ ppm, DMSO-$d_6$, 400 MHz): 10.32 (s, 1H), 7.85 (d, J 8.8, 2H), 7.61 (d, J 8.8, 2H), 6.61 (s, 1H), 2.66 (s, 3H), 2.55 (s, 3H), 1.84-1.79 (m, 1H), 0.97-0.94 (m, 2H), 0.83-0.79 (m, 2H). MS (m/z): 405.17 [M−H]$^−$.

Example 56

N-{4-[5-cyclopropyl-3-(trifluoromethyl)-1H-pyrazol-1-yl]phenyl}-5-methylisoxazole-4-carboxamide Following the general procedure-2, title compound (50 mg) was prepared from 5-methylisoxazole-4-carbonyl chloride (71 mg, 0.489 mmol) and intermediate 31 (120 mg, 0.45 mmol) as a brown solid. M. P. 90-95° C. $^1$H-NMR (δ ppm, DMSO-$d_6$, 400 MHz): 10.44 (s, 1H), 8.76 (s, 1H), 7.88 (d, J 8.8, 2H), 7.63 (d, J 9.5, 2H), 6.61 (s, 1H), 2.63 (s, 3H), 1.85-1.80 (m, 1H), 0.99-0.93 (m, 2H), 0.84-0.79 (m, 2H). MS (m/z): 375.10 [M−H]$^−$.

Example 57

N-{4-[5-cyclopropyl-3-(trifluoromethyl)-1H-pyrazol-1-yl]phenyl}-3,5-dimethylisoxazole-4-carboxamide Following the general procedure-2, the title compound (130 mg) was prepared from 3,5-dimethylisoxazole-4-carbonyl chloride (85 mg, 0.54 mmol) and intermediate 31 (120 mg, 0.45 mmol) as a pale-yellow solid. M.P.: 170-172° C. $^1$H-NMR (δ ppm, DMSO-$d_6$, 400 MHz): 10.29 (s, 1H), 7.85 (d, J 8.9, 2H), 7.62 (d, J 8.9, 2H), 6.61 (s, 1H), 2.56 (s, 3H), 2.34 (s, 3H), 1.90-1.80 (m, 1H), 1.01-0.94 (m, 2H), 0.86-0.78 (m, 2H). MS (m/z): 388.61 [M−H]$^−$.

Example 58

N-{4-[5-cyclopropyl-3-(trifluoromethyl)-1H-pyrazol-1-yl]phenyl}-1-methyl-1H-imidazole-2-carboxamide Following the general procedure-1, the title compound (25 mg) was prepared from intermediate 31 (220 mg, 0.79 mmol) and 1-methyl-1H-imidazole-2-carboxylic acid (100 mg, 0.79 mmol) as a white solid. M.P.: 132.1-134.5° C. $^1$H-NMR (δ ppm, DMSO-$d_6$, 400 MHz): 10.63 (s, 1H), 8.03 (d, J 8.9, 2H), 7.59 (d, J 8.9, 2H), 7.46 (s, 1H), 7.10 (s, 1H), 6.60 (s, 1H), 4.00 (s, 3H), 1.86-1.80 (m, 1H), 0.99-0.92 (m, 2H), 0.85-0.78 (m, 2H). MS (nm/z): 376.09 [M+H]$^+$.

Example 59

N-{4-[3-cyclopropyl-5-(trifluoromethyl)-1H-pyrazol-1-yl]phenyl}-4-methyl-1H-imidazole-5-carboxamide Following the general procedure-1, the title compound (150 mg) was prepared from intermediate 31 (150 mg, 0.56 mmol) and 4-methyl-1H-imidazole-5-carboxylic acid (85 mg, 0.67 mmol) as an off-white solid. M.P.: 245-250° C. $^1$H-NMR (δ ppm, DMSO-$d_6$, 400 MHz): 12.46 (bs, 1H), 9.99 (s, 1H), 8.02 (d, J 8.9, 2H), 7.67 (s, 1H), 7.54 (d, J 8.9, 2H), 6.59 (s, 1H), 2.48 (s, 3H), 1.86-1.76 (m, 1H), 1.00-0.92 (m, 2H), 0.82-0.74 (m, 2H). MS (m/z): 374.04 [M−H]$^−$.

Example 60

N-{4-[5-cyclopropyl-3-(trifluoromethyl)-1H-pyrazol-1-yl]phenyl}-2-methylbenzamide Following the general procedure-1, the title compound (80 mg) was prepared from intermediate 31 (200 mg, 0.75 mmol) and o-toluic acid (163 mg, 1.2 mmol) as an off-white solid. M.P.: 143.2-145.8° C. $^1$H-NMR (δ ppm, DMSO-$d_6$, 400 MHz): 10.56 (s, 1H), 7.93 (d, J 8.8, 2H), 7.60 (d, J 8.8, 2H), 7.48 (d, J 7.6, 1H), 7.42-7.38 (m, 1H), 7.32-7.29 (m, 2H), 6.61 (s, 1H), 2.39 (s, 3H), 1.88-1.78 (m, 1H), 1.00-0.92 (m, 2H), 0.84-0.76 (m, 2H). MS (nm/z): 383.62 [M−H]$^−$.

Example 61

N-{4-[5-cyclopropyl-3-(trifluoromethyl)-1H-pyrazol-1-yl]phenyl}-2,3-difluorobenzamide The title compound (28 mg) was prepared from 2,3-difluorobenzoic acid (71 mg, 0.45 mmol) and intermediate 31 (100 mg, 0.374 mmol) as a white solid. M. P. 147-152° C. $^1$H-NMR (δ ppm, DMSO-$d_6$, 400 MHz): 10.80 (s, 1H), 7.90 (d, J 8.7, 2H), 7.64 (d, J 8.7, 2H), 7.53-7.50 (m, 1H), 7.37-7.34 (m, 2H), 6.62 (s, 1H), 1.83-1.82 (m, 1H), 0.83-0.79 (m, 2H), 0.99-0.94 (m, 2H). MS (m/z): 406.05 [M−H]$^−$.

Example 62

N-{4-[5-cyclopropyl-3-(trifluoromethyl)-1H-pyrazol-1-yl]phenyl}-2,6-difluorobenzamide Following the general procedure-1, the title compound (20 mg) was prepared from 2,6-difluorobenzoic acid (142 mg, 0.89 mmol) and intermediate 31 (100 mg, 0.374 mmol) as a pale yellow solid. M. P. 188-191° C. $^1$H-NMR (S ppm, DMSO-$d_6$, 400 MHz): 11.06 (s, 1H), 7.87 (d, J 8.8, 2H), 7.64 (d, J 8.8, 2H), 7.63-7.59 (m, 1H), 7.29-7.25 (m, 2H), 6.62 (s, 1H), 1.85-1.82 (m, 1H), 0.99-0.94 (m, 2H), 0.83-0.79 (m, 2H). MS (m/z): 406.05 [M−H]$^−$.

Example 63

N-{4-[5-cyclopropyl-3-(trifluoromethyl)-1H-pyrazol-1-yl]phenyl}-3-(methylsulfonyl)benzamide Following the general procedure-2, the title compound (43 mg) was prepared from 3-(methylsulfonyl)benzoyl chloride (108 mg, 0.49 mmol) and intermediate 31 (100 mg, 0.45 mmol) as a white solid. M. P. 178-184° C. $^1$H-NMR (δ ppm, DMSO-$d_6$, 400 MHz): 10.76 (s, 1H), 8.49 (s, 1H), 8.31 (d, J 7.5, 1H), 8.15 (d, J 7.5, 1H), 7.98 (d, J 8.6, 2H), 7.84 (t, J 7.8, 1H), 7.66 (d, J 8.6, 2H), 6.62 (s, 1H), 3.21 (s, 3H), 1.98-1.82 (m, 1H), 1.07-0.94 (m, 2H), 0.90-0.75 (m, 2H). MS (m/z): 448.22 [M−H]$^−$.

Example 64

2-chloro-N-{4-[5-cyclopropyl-3-(trifluoromethyl)-1H-pyrazol-1-yl]phenyl}-5-(methylthio)benzamide Following the general procedure-1, the title compound (63 mg) was prepared from 2-chloro-5-(methylthio)benzoic acid (100 mg, 0.49 mmol) and intermediate 31 (120 mg, 0.45 mmol) as a white solid. M.P.: 172-177° C. $^1$H-NMR (δ ppm, DMSO-$d_6$, 400 MHz): 10.78 (s, 1H), 7.90 (d, J 8.8, 2H),7.63 (d, J 8.8, 2H), 7.50-7.47 (m, 2H), 7.39 (dd, J, 2.4, 8.4, 1H), 6.61 (s, 1H), 2.52 (s, 3H), 1.86-1.79 (m, 1H), 0.99-0.94 (m, 2H), 0.84-0.79 (m, 2H). MS (m/z): 449.96 [M−H]⁻.

Example 65

2-chloro-N-{4-[5-cyclopropyl-3-(trifluoromethyl)-1H-pyrazol-1-yl]phenyl}-5-(methylsulfonyl)benzamide 2-chloro-N-{4-[5-cyclopropyl-3-(trifluoromethyl)-1H-pyrazol-1-yl]phenyl}-5-(methylthio)benzamide (40 mg, 0.08 mmols) was dissolved in a 5 mL mixture of $H_2O$ and acetone (1:1) at 0° C. and added Oxone (108 mg, 0.16 mmols). The mixture was stirred at ambient temperature for one hour. The reaction mixture was filtered to remove oxone and filtrate was worked up (AcOEt: $H_2O$). Title compound (38 mg) was obtained as a white solid. M. P. 132-135° C. ¹H-NMR (δ ppm, DMSO-$d_6$, 400 MHz): 10.97 (s, 1H), 8.19 (d, J 2.2, 1H), 8.04 (dd, J 8.4, 2.2, 1H), 7.89 (d, J 8.6, 3H), 7.65 (d, J 8.8, 2H), 6.62 (s, 1H), 3.30 (s, 3H), 1.97-1.81 (m, 1H), 0.99-0.94 (m, 2H), 0.86-0.79 (m, 2H). MS (m/z): 481.85 [M−H]⁻.

Example 66

N-{4-[5-cyclopropyl-3-(trifluoromethyl)-1H-pyrazol-1-yl]phenyl}pyridine-4-carboxamide hydrochloride Following general procedure-1, N-{4-[5-cyclopropyl-3-(trifluoromethyl)-1H-pyrazol-1-yl]phenyl}pyridine-4-carboxamide (120 mg) was prepared from pyridine-4-carboxylic acid (66 mg, 0.54 mmol) and intermediate 31 (120 mg, 0.45 mmol) as a pale yellow solid and dissolved in THF. Saturated HCl in diethyl ether was added at 0° C. to it and stirred for 15 min. Solid that separated out was filtered and dried to give the title compound (70 mg) as a yellow solid. M. P. 210-215° C. ¹H-NMR (δ ppm, DMSO-$d_6$, 400 MHz): 10.90 (s, 1H), 8.90 (d, J 5.40, 2H), 8.07 (d, J 5.40, 2H), 7.99 (d, J 8.8, 2H), 7.66 (d, J 8.8, 2H), 6.62 (s, 1H), 1.86-1.82 (m, 1H), 0.99-0.95 (m, 2H), 0.83-0.79 (m, 2H). MS (m/z): 406.89 [M−H]⁻.

Example 67

N-{4-[5-cyclopropyl-3-(trifluoromethyl)-1H-pyrazol-1-yl]phenyl}-3-fluoroisonicotinamide Following the general procedure-1, the title compound (160 mg) was prepared from intermediate 31 (200 mg, 0.75 mmol) and 3-fluoroisonicotinic acid (168 mg, 1.2 mmol) as a brown solid. M.P.: 143.2-145.9° C. ¹H-NMR (δ ppm, DMSO-$d_6$, 400 MHz): 10.95 (s, 1H), 8.78 (d, J 1, 1H), 8.60 (dd, J 1, 4.8, 1H), 7.89 (d, J 8.9, 2H), 7.73 (d, J 5.3, 1H), 7.66 (d, J 8.9, 2H), 6.62 (s, 1H), 1.88-1.79 (m, 1H), 1.00-0.93 (m, 2H), 0.85-0.78 (m, 2H). MS (m/z): 391.14 [M+H]⁺.

Example 68

N-{4-[5-cyclopropyl-3-(trifluoromethyl)-1H-pyrazol-1-yl]phenyl}-4-methylpyrimidine-5-carboxamide Following the general procedure-1, the title compound (17 mg) was prepared from intermediate 31 (200 mg, 0.75 mmol) and intermediate 53 (123 mg, 0.89 mmol) as an off-white solid. M.P.: 163.4-165.5° C. ¹H-NMR (δ ppm, DMSO-$d_6$, 400 MHz): 10.87 (s, 1H), 9.16 (s, 1H), 8.92 (s, 1H), 7.91 (d, J 8.8, 2H), 7.65 (d, J 8.8, 2H), 6.62 (s, 1H), 2.60 (s, 3H), 1.90-1.78 (m, 1H), 1.00-0.92 (m, 2H), 0.85-0.76 (m, 2H). MS (m/z): 387.36 [M+H]⁺.

Example 69

N-{4-[5-cyclopropyl-3-(trifluoromethyl)-1H-pyrazol-1-yl]phenyl}-2,4-dimethylpyrimidine-5-carboxamide Following the general procedure-1, the title compound (150 mg) was prepared from intermediate 31 (150 mg, 0.56 mmol) and intermediate 55 (170 mg, 1.12 mmol) as a pale-yellow solid. M.P.: 144.8-146.8° C. ¹H-NMR (δ ppm, DMSO-$d_6$, 400 MHz): 10.78 (s, 1H), 8.80 (s, 1H), 7.90 (d, J 8, 2H), 7.64 (d, J 8, 2H), 6.63 (s, 1H), 2.63 (s, 3H), 2.55 (s, 3H), 1.90-1.78 (m, 1H), 1.01-0.90 (m, 2H), 0.82-0.74 (m, 2H). MS (m/z): 402.06 [M+H]⁺.

Example 70

N-{4-[5-cyclopropyl-3-(trifluoromethyl)-1H-pyrazol-1-yl]phenyl}-2-(4-fluorophenyl)acetamide The title compound (14 mg) was prepared from 2-(4-fluorophenyl)acetic acid (83 mg, 0.54 mmol) and intermediate 31 (120 mg, 0.45 mmol) as a pale yellow colour solid. M. P. 135-140° C. ¹H-NMR (δ ppm, DMSO-$d_6$, 400 MHz): 10.42 (s, 1H), 7.77 (d, J 8.8, 2H), 7.56 (d, J 8.8, 2H), 7.38-7.35 (m, 2H), 7.12 (t, J 8.8, 2H), 6.59 (s, 1H), 3.67 (s, 2H), 1.81-1.77 (m, 1H), 0.96-0.91 (m, 2H), 0.86-0.77 (m, 2H). MS (m/z): 402.01 [M−H]⁻.

Example 71

N-{4-[5-cyclopropyl-3-(trifluoromethyl)-1H-pyrazol-1-yl]phenyl}-2-(pyridin-2-yl)acetamide hydrochloride Following the general procedure-1, N-{4-[5-cyclopropyl-3-(trifluoromethyl)-1H-pyrazol-1-yl]phenyl}-2-(pyridin-2-yl)acetamide (107 mg) was prepared from 2-pyridylacetic acid (124 mg, 0.71 mmol) and intermediate 31 (120 mg, 0.45 mmol) as a pale yellow solid and dissolved in THF. Saturated HCl in diethyl ether was added to this solution at 0° C. and stirred for 15 min. Solid that separated out was filtered and dried to give the title compound (90 mg) as a pale yellow solid. M. P. 210-215° C. ¹H-NMR (6 ppm, DMSO-$d_6$, 400 MHz): 10.80 (s, 1H), 8.79 (d, J 4.8, 1H), 8.31 (t, J 7.2, 1H), 7.86 (d, J 7.4, 1H), 7.84-7.79 (m, 4H), 7.59 (d, J 8.8, 2H), 6.60 (s, 1H), 4.20 (s, 2H), 1.85-1.75 (m, 1H), 0.99-0.90 (m, 2H), 0.82-0.75 (m, 2H). MS (m/z): 420.89 [M−H]⁻.

Example 72

N-{4-[5-cyclopropyl-3-(trifluoromethyl)-1H-pyrazol-1-yl]phenyl}-2-(pyridin-3-yl)acetamide hydrochloride Following the general procedure-1, N-{4-[5-cyclopropyl-3-(trifluoromethyl)-1H-pyrazol-1-yl]phenyl}-2-(pyridin-3-yl)acetamide (140 mg) was prepared from 3-pyridylacetic acid (124 mg, 0.714 mmol) and intermediate 31 (120 mg, 0.45 mmol) as a white solid and dissolved in THF. Saturated HCl in diethyl ether was added to this solution at 0° C. and stirred for 15 min. Solid that separated out was filtered and dried to give the title compound (101 mg) as a pale yellow solid. M. P. 196-201° C. ¹H-NMR (δ ppm, DMSO-d₆, 400 MHz): 10.81 (s, 1H), 8.89 (s, 1H), 8.81 (d, J 5.4, 1H), 8.48 (d, J 7.4, 1H) 8.00-7.97 (m, 1H), 7.80 (d, J 8.7, 2H), 7.58 (d, J 8.7, 2H), 6.59 (s, 1H), 4.04 (s, 2H), 1.84-1.75 (m, 1H), 0.97-0.91 (m, 2H), 0.80-0.75 (m, 2H). MS (nm/z): 423.2 [M+H]⁺.

Example 73

N-{4-[5-cyclopropyl-3-(trifluoromethyl)-1H-pyrazol-1-yl]phenyl}-2-(pyridin-4-yl)acetamide hydrochloride Following the general procedure-1, N-{4-[5-cyclopropyl-3-(trifluoromethyl)-1H-pyrazol-1-yl]phenyl}-2-(pyridin-4-yl)acetamide (38 mg) was prepared from 2-(pyridin-4-yl) acetic acid (94 mg, 0.54 mmol) and intermediate 31 (120 mg, 0.45 mmol) as a pale-yellow solid and dissolved in THF. Saturated HCl in diethyl ether was added to this solution at 0° C. and stirred for 15 min. Solid that separated out was filtered and dried to give the title compound (30 mg) as a brown solid. M. P. 135-139° C. ¹H-NMR (δ ppm, DMSO-d₆, 400 MHz): 10.93 (s, 1H), 8.85 (d, J 5.8, 2H), 8.01 (d, J 5.8, 2H), 7.81 (d, J 8.6, 2H), 7.58 (d, J 8.6, 2H), 6.59 (s, 1H), 4.13 (s, 2H), 1.83-1.74 (m, 1H), 0.99-0.91 (m, 2H), 0.83-0.76 (m, 2H). MS (m/z): 387.27 [M+H−HCl]⁺.

Example 74

4-[5-cyclopropyl-3-(trifluoromethyl)-1H-pyrazol-1-yl]-N-[(4-methylthiazol-5-yl)methyl]aniline Intermediate 31 (600 mg, 2.24 mmol) was dissolved in THF, added intermediate 58 (338 mg, 2.7 mmol), sodium triacetoxy borohydride (710 mg, 3.4 mmol) and AcOH (0.12 ml, 2.24 mmol). The mixture was stirred at rt for 48 hrs. After completion of the reaction, THF was removed on rotavapour to obtain the residue. Work up (AcOEt/H₂O) and purification on silicagel (60-120 mesh) using EA and Peteher (25:75) afforded the title compound (31 mg) as a white solid. M.P.: 59.2-61.2° C. ¹H-NMR (δ ppm, DMSO-d₆, 400 MHz): 8.84 (s, 1H), 7.28 (d, J 8.8, 2H), 6.71 (d, J 8.8, 2H), 6.66 (t, J 5.7, 1H), 6.49 (s, 1H), 4.45 (d, J 5.7, 2H), 2.49 (s, 3H), 1.79-1.69 (m, 1H), 0.98-0.90 (m, 2H), 0.80-0.74 (m, 2H). MS (m/z): 376.98 [M−H]⁻.

Example 75

1-{4-[5-cyclopropyl-3-(trifluoromethyl)-1H-pyrazol-1-yl]phenyl}-3-(4-methyl-1,2,3-thiadiazol-5-yl)urea 4-methylthiadiazole-5-carboxylic acid (300 mg, 1.92 mmol) was dissolved in acetone, water mixture (15 ml and 1.5 ml) and cooled to −5° C. Ethyl choroformate (0.32 ml, 2.3 mmol) was added slowly to this mixture and stirred at same temperature for 30 mins. At this stage sodium azide (250 mg, 3.84 mmol) was added and stirred for 30 mins at the same temperature. Water was added to the reaction mixture and extracted with Et₂O and ether was removed to obtain the crude. Crude was dissolved in dioxane, intermediate 31 (90 mg, 0.33 mmol) was added and refluxed for 30 mins. Work up (AcOEt:H₂O) followed by purification on 60-120 mesh silica gel using EA and Peteher (45:50) as eluent afforded the title compound (150 mg) as a white solid. M.P.: 124-128° C. ¹H-NMR (δ ppm, DMSO-d₆, 400 MHz): 10.27 (s, 1H), 9.45 (s, 1H), 7.68 (d, J 8.9, 2H), 7.60 (d, J 8.9, 2H), 6.61 (s, 1H), 2.60 (s, 3H), 1.88-1.78 (m, 1H), 1.00-0.92 (m, 2H), 0.84-0.76 (m, 2H). MS (m/z): 394. [M−H]⁻. MS (m/z): 407.01 [M−H]⁻.

Example 76

1-{4-[5-cyclopropyl-3-(trifluoromethyl)-1H-pyrazol-1-yl]phenyl}-3-(4-methylthiazol-5-yl)urea 4-methylthiazole-5-carboxylic acid (1 g, 6.99 mmol) was dissolved in acetone, water mixture (50 ml and 5 ml) and cooled to −5° C. Ethyl choroformate was added slowly to this mixture and stirred at same temperature for 30 mins. At this stage sodium azide (0.9 g, 13.8 mmol) was added and stirred for 30 mins at the same temperature. Water was added to the reaction mixture and extracted with Et₂CO and ether was removed to obtain the crude. Crude was dissolved in dioxane, intermediate 31 was added and refluxed for 30 mins. Work up (AcOEt:H₂O) followed by purification on 60-120 mesh silica gel using EA and Peteher (45:50) as eluent afforded the title compound (2.1 g) as a pale yellow solid. M.P.: 124-126° C. ¹H-NMR (δ ppm, DMSO-d₆, 400 MHz): 9.17 (s, 1H), 9.15 (s, 1H), 8.50 (s, 1H), 7.64 (d, J 8.9, 2H), 7.55 (d, J 8.9, 2H), 6.59 (s, 1H), 2.32 (s, 3H), 1.84-1.74 (m, 1H), 1.02-0.92 (m, 2H), 0.82-0.74 (m, 2H). MS (m/z): 405.49 [M−H]⁻.

Example 77

1-{4-[5-cyclopropyl-3-(trifluoromethyl)-1H-pyrazol-1-yl]phenyl}-3-(4-methylpyrimidin-5-yl)urea 4-methylpyrimidine-5-carbonyl azide (450 mg, 2.43 mmol) and intermediate 31 (649 mg, 2.43 mmol) were dissolved in dioxane and refluxed for 30 mins. Work up (AcOEt:H₂O) followed by purification on 60-120 mesh silica gel using EA and Peteher (10:90) as eluent afforded the title compound (200 mg) as a pale yellow solid. M. P.: 190-192° C. ¹H-NMR (δ ppm, DMSO-d₆, 400 MHz): 9.23 (s, 1H), 8.78 (s, 1H), 8.69 (s, 1H), 7.86 (s, 1H), 7.50 (dd, J 2, 6.9, 4H), 6.10 (s, 1H), 2.44 (s, 3H), 1.74-1.66 (m, 1H), 0.97-0.91 (m, 2H), 0.75-0.65 (m, 2H). MS (m/z): 401.27 [M−H]⁻.

Example 78

4-[5-cyclopropyl-3-(trifluoromethyl)-1H-pyrazol-1-yl]-N-(4-methylthiazol-5-yl)benzamide Following the general procedure-1, the title compound (40 mg) was prepared from intermediate 47 (98 mg, 0.86 mmol) and intermediate 59 (170 mg, 0.57 mmol) as an off-white solid M.P.: 125-128° C. ¹H-NMR (δ ppm, DMSO-d₆, 400 MHz): 10.83 (s, 1H), 8.70 (s, 1H), 8.15 (d, J 8.4, 2H), 7.86 (d, J 8.4, 2H), 6.72 (s, 1H), 2.42 (s, 3H), 1.99-1.88 (m, 1H), 1.05-0.97 (m, 2H), 0.89-0.79 (m, 2H). MS (m/z): 392.84 [M+H]⁺.

Example 79

4-[5-cyclopropyl-3-(trifluoromethyl)-1H-pyrazol-1-yl]-N-(2,6-difluorophenyl)benzamide Following the general procedure-2, the title compound (8 mg) was prepared from intermediate 47 (150 mg, 0.53 mmol) and 2,6-difluoroaniline (194 mg, 0.63 mmol) as a white solid. M.P.: 145.2-147.3° C. ¹H-NMR (δ ppm, DMSO-d$_6$, 400 MHz): 10.33 (s, 1H), 8.18 (d, J 8.6, 2H), 7.86 (d, J 8.6, 2H), 7.44-7.40 (m, 1H), 7.23 (t, J 8.1, 2H), 6.72 (s, 1H), 2.00-1.90 (m, 1H), 1.03-0.97 (m, 2H), 0.90-0.80 (m, 2H). MS (m/z): 405.70 [M–H]$^-$.

Example 80

N-{4-[4-chloro-5-cyclopropyl-3-(trifluoromethyl)-1H-pyrazol-1-yl]phenyl}-4-methylthiazole-5-carboxamide Following the general procedure-2, the title compound (71 mg) was prepared from 4-methylthiazole-5-carbonyl chloride (70 mg, 0.44 mmol) and intermediate 32 (120 mg, 0.4 mmol) as a white solid. M.P.: 161-164° C. $^1$H-NMR (δ ppm, DMSO-d$_6$, 400 MHz): 10.47 (s, 1H), 9.14 (s, 1H), 7.86 (d, J 8.7, 2H), 7.63 (d, J 8.7, 2H), 3.29 (s, 3H), 2.01-1.94 (m, 1H), 0.90-0.86 (m, 2H), 0.65-0.61 (m, 2H). MS (m/z): 425.08 [M–H]$^-$.

Example 81

N-{4-[4-chloro-5-cyclopropyl-3-(trifluoromethyl)-1H-pyrazol-1-yl]phenyl}-2-(pyridin-2-yl)acetamide hydrochloride Following the general procedure-1, the title compound (32 mg) was prepared from 2-(pyridin-2-yl)acetic acid acid (80 mg, 0.47 mmol) and intermediate 32 (120 mg, 0.40 mmol) as a white solid. M.P.: 215-219° C. $^1$H-NMR (δ ppm, DMSO-d$_6$, 400 MHz): 10.82 (s, 1H), 8.78 (d, J 5, 2H), 8.31 (t, J 7, 1H), 7.86 (d, J 7.8, 1H), 7.81-7.73 (m, 3H), 7.59 (d, J 8.7, 1H), 4.20 (s, 2H), 2.00-1.91 (m, 1H), 0.90-0.81 (m, 2H), 0.63-0.54 (m, 2H). MS (m/z): 421.23 [M+H–HCl]$^+$.

Example 82

N-{$^4$-[5-cyclopropyl-3-(trifluoromethyl)-1H-pyrazol-1-yl]-3-fluorophenyl}-4-methyl-1,2,3-thiadiazole-5-carboxamide Following the general procedure-2, the title compound (33 mg) was prepared from 4-methyl-1,2,3-thiadiazole-5-carbonyl chloride (147 mg, 0.76 mmol) and intermediate 33 (200 mg, 0.76 mmol) as a white solid. M.P.: 105-112° C. $^1$H-NMR (6 ppm, DMSO-d$_6$, 400 MHz): 11.17 (s, 1H), 7.93 (d, J 12.2, 1H), 7.72-7.60 (m, 2H), 6.6 (s, 1H), 3.31 (s, 3H), 1.66-1.58 (m, 1H), 0.94-0.84 (m, 2H), 0.8-0.72 (m, 2H). MS (m/z): 410.09 [M–H]$^-$.

Example 83

N-{$^4$-[5-cyclopropyl-3-(trifluoromethyl)-1H-pyrazol-1-yl]-3-fluorophenyl}-4-methylthiazole-5-carboxamide Following the general procedure-2, the title compound (37 mg) was prepared from 4-methylthiazole-5-carbonyl chloride (60 mg, 0.37 mmol) and intermediate 33 (100 mg, 0.37 mmol) as a white solid. M.P.: 95-97.6° C. $^1$H-NMR (δ ppm, DMSO-d$_6$, 400 MHz): 10.66 (s, 1H), 9.17 (s, 1H), 7.92 (d, J 12.5, 1H), 7.64 (d, J 2.4, 2H), 6.61 (s, 1H), 2.63 (s, 3H), 1.70-1.56 (m, 1H), 1.00-0.89 (m, 2H), 0.80-0.72 (m, 2H). MS (m/z): 408.98 [M–H]$^-$.

Example 84

N-{4-[5-cyclopropyl-3-(trifluoromethyl)-1H-pyrazol-1-yl]-3-fluorophenyl}-5-methylisoxazole-4-carboxamide Following the general procedure-2, the title compound (37 mg) was prepared from 5-methylisoxazole-4-carbonyl chloride (73 mg, 0.50 mmol) and intermediate 33 (120 mg, 0.42 mmol) as a white solid. M.P.: 125-128° C. $^1$H-NMR (δ ppm, DMSO-d$_6$, 400 MHz): 10.47 (s, 1H), 9.08 (s, 1H), 7.95 (dd, J 2, 12.9, 1H), 7.68-7.60 (m, 2H), 6.62 (s, 1H), 2.69 (s, 3H), 1.67-1.58 (m, 1H), 0.95-0.85 (m, 2H), 0.80-0.72 (m, 2H). MS (m/z): 392.61 [M–H]$^-$.

Example 85

N-{4-[5-cyclopropyl-3-(trifluoromethyl)-1H-pyrazol-1-yl]-3-fluorophenyl}-3,5-dimethylisoxazole-4-carboxamide Following the general procedure-2, the title compound (54 mg) was prepared from intermediate 33 (200 mg, 0.70 mmol) and 3,5-dimethylisoxazole-4-carboxylic acid (120 mg, 0.85 mmol) as a white solid. M.P.: 163-165° C. $^1$H-NMR (δ ppm, DMSO-d$_6$, 400 MHz): 10.50 (s, 1H), 7.91 (dd, J 2, 12.6, 1H), 7.65 (t, J 8.6, 1H), 7.57 (dd, J 2, 8.8, 1H), 6.61 (s, 1H), 2.56 (s, 3H), 2.34 (s, 3H), 1.94-1.87 (m, 1H), 0.94-0.86 (m, 2H), 0.80-0.72 (m, 2H). MS (m/z): 409.04 [M+H]$^+$.

Example 86

N-{4-[5-cyclopropyl-3-(trifluoromethyl)-1H-pyrazol-1-yl]-3-fluorophenyl}-2-methylbenzamide Following the general procedure-1, the title compound (24 mg) was prepared from intermediate 33 (200 mg, 0.7 mmol) and o-toluic acid (153 mg, 1.1 mmol) as a pale-yellow solid. M.P.: 141.6-143.7° C. $^1$H-NMR (δ ppm, DMSO-d$_6$, 400 MHz): 10.78 (s, 1H), 8.01-7.98 (m, 1H), 7.69-7.60 (m, 2H), 7.50 (d, J 7.6, 1H), 7.44-7.40 (m, 1H), 7.33 (d, J 7.5, 2H), 6.61 (s, 1H), 2.39 (s, 3H), 1.69-1.60 (m, 1H), 0.94-0.88 (m, 2H), 0.80-0.72 (m, 2H). MS (m/z): 401.54 [M–H]$^-$.

Example 87

N-{4-[5-cyclopropyl-3-(trifluoromethyl)-1H-pyrazol-1-yl]-3-fluorophenyl}-2,3-difluorobenzamide Following the general procedure-2, the title compound (156 mg) was prepared from intermediate 33 (200 mg, 0.70 mmol) and 2,3-difluorobenzoic acid (150 mg, 0.95 mmol) as a white solid. M.P.: 132-135° C. $^1$H-NMR (δ ppm, DMSO-d$_6$, 400 MHz): 11.03 (s, 1H), 7.96 (dd, J 1.9, 12.7, 1H), 7.71-7.61 (m, 3H), 7.56-7.51 (m, 1H), 7.42-7.34 (m, 1H), 6.62 (s, 1H), 1.67-1.58 (m, 1H), 0.94-0.86 (m, 2H), 0.79-0.72 (m, 2H). MS (m/z): 424.02 [M–H]$^-$.

Example 88

N-{4-[5-cyclopropyl-3-(trifluoromethyl)-1H-pyrazol-1-yl]-3-fluorophenyl}-2,6-difluorobenzamide Following the general procedure-1, the title compound (195 mg) was prepared from intermediate 33 (200 mg, 0.75 mmol) and 2,6-difluorobenzoic acid (189 mg, 1.2 mmol) as a white solid. M.P.: 193.1-196.4° C. ¹H-NMR (δ ppm, DMSO-d₆, 400 MHz): 11.30 (s, 1H), 7.92 (dd, J 2, 12.3, 1H), 7.69-7.58 (m, 3H), 7.29 (t, J 8.1, 2H), 6.62 (s, 1H), 1.70-1.60 (m, 1H), 0.95-0.88 (m, 2H), 0.80-0.74 (m, 2H). MS (m/z): 423.51 [M−H]⁻.

Example 89

N-{4-[5-cyclopropyl-3-(trifluoromethyl)-1H-pyrazol-1-yl]-3-fluorophenyl}nicotinamide hydrochloride Following the general procedure-1, N-{4-[3-cyclopropyl-5-(trifluoromethyl)-1H-pyrazol-1-yl]-3-fluorophenyl}nicotinamide (30 mg) from intermediate 33 (200 mg, 0.7 mmol) and nicotinic acid (138 mg, 1.12 mmol) as a pale yellow solid and dissolved in THF. Saturated HCl in diethyl ether was added to this solution at 0° C. and stirred for 15 min. Solid that separated out was filtered and dried to give the title compound (68 mg) as an Off-white solid M.P.: 170-172° C. ¹H-NMR (δ ppm, DMSO-d₆, 400 MHz): 10.98 (s, 1H), 9.18 (d, J 1.4, 1H), 8.84 (d, J 3.7, 1H), 8.42 (d, J 8, 1H), 8.04 (dd, J 2.1, 12.6, 1H), 7.77-7.74 (m, 1H), 7.70-7.65 (m, 2H), 6.62 (s, 1H), 1.69-1.59 (m, 1H), 0.96-0.88 (m, 2H), 0.76-0.70 (m, 2H). MS (m/z): 390.93 [M−H−HCl]⁺.

Example 90

N-{4-[5-cyclopropyl-3-(trifluoromethyl)-1H-pyrazol-1-yl]-3-fluorophenyl}isonicotinamide hydrochloride Following the general procedure-1, N-{4-[3-cyclopropyl-5-(trifluoromethyl)-1H-pyrazol-1-yl]-3-fluorophenyl}isonicotinamide (60 mg) prepared from intermediate 33 (200 mg, 0.7 mmol) and isonicotinic acid (138 mg, 1.12 mmol) as a pale yellow solid and dissolved in THF. Saturated HCl in diethyl ether was added to this solution at 0° C. and stirred for 15 min. Solid that separated out was filtered and dried to give the title compound (53 mg) as a pale-yellow solid. M.P.: 148-153° C. ¹H-NMR (δ ppm, DMSO-d₆, 400 MHz): 11.12 (s, 1H), 8.90 (d, J 1.9, 2H), 8.07-8.03 (m, 3H), 7.77 (dd, J 1.9, 8.8, 1H), 7.68 (t, J 8.6, 1H), 6.63 (s, 1H), 1.78-1.68 (m, 1H), 0.95-0.85 (m, 2H), 0.80-0.73 (m, 2H). MS (nm/z): 390.93 [M−H−HCl]⁻.

Example 91

N-{4-[5-cyclopropyl-3-(trifluoromethyl)-1H-pyrazol-1-yl]-3-fluorophenyl}-3-fluoroisonicotinamide Following the general procedure-1, the title compound (25 mg) was prepared from intermediate 33 (200 mg, 0.7 mmol) and 3-fluoronicotinic acid (158 mg, 1.1 mmol) as a black solid. M.P.: 161-165° C. ¹H-NMR (δ ppm, DMSO-d₆, 400 MHz): 11.17 (s, 1H), 8.80 (s, 1H), 8.61 (d, J 4.8, 1H), 7.94 (d, J 11.8, 1H), 7.75 (t, J 5.2, 1H), 7.68 (t, J 8.2, 1H), 7.62 (d, J 9.1, 1H), 6.62 (s, 1H), 1.70-1.58 (m, 1H), 0.96-0.88 (m, 2H), 0.80-0.72 (m, 2H). MS (m/z): 408.32 [M+H]⁺.

Example 92

3,5-dichloro-N-{4-[5-cyclopropyl-3-(trifluoromethyl)-1H-pyrazol-1-yl]-3-fluorophenyl}isonicotinamide Following the general procedure-2, the title compound (86 mg) was prepared from intermediate 33 (150 mg, 0.55 mmol) and 3,5-dichloroisonicotinoyl chloride (132 mg, 0.63 mmol) as a white solid. M.P.: 218-223° C. ¹H-NMR (δ ppm, DMSO-d₆, 400 MHz): 11.48 (s, 1H), 8.84 (s, 2H), 7.89 (dd, J 2.2, 12.04, 1H), 7.70 (t, J 8.6, 1H), 7.56 (dd, J 1.6, 8.6, 1H), 6.63 (s, 1H), 1.70-1.60 (m, 1H), 0.96-0.88 (m, 2H), 0.80-0.72 (m, 2H). MS (m/z): 458.33 [M−H]⁻.

Example 93

N-{4-[5-cyclopropyl-3-(trifluoromethyl)-1H-pyrazol-1-yl]-3-fluorophenyl}-4-methylpyrimidine-5-carboxamide Following the general procedure-1, the title compound (150 mg) was prepared from intermediate 53 (130 mg, 0.67 mmol) and intermediate 33 (150 mg, 0.57 mmol) as a pale-yellow solid. M.P.: 101-103° C. ¹H-NMR (δ ppm, DMSO-d₆, 400 MHz): 11.08 (s, 1H), 9.17 (s, 1H), 8.94 (s, 1H), 7.97 (d, J 12.2, 1H), 7.70-7.61 (m, 2H), 6.62 (s, 1H), 1.70-1.57 (m, 1H), 0.98-0.90 (m, 2H), 0.80-0.72 (m, 2H). MS (m/z): 403.71 [M−H]⁻.

Example 94

N-{4-[5-cyclopropyl-3-(trifluoromethyl)-1H-pyrazol-1-yl]-3-fluorophenyl}-N,4-dimethylpyrimidine-5-carboxamide N-{4-[5-cyclopropyl-3-(trifluoromethyl)-1H-pyrazol-1-yl]-3-fluorophenyl}-4-methylpyrimidine-5-carboxamide (300 mg, 0.74 mmol) was dissolved in THF, cooled to 0° C., added sodium hydride (35 mg, 1.48 mmol) and stirred the mixture for 30 mins at the same temperature. Methyl Iodide (120 mg, 0.84 mmol) was added and heated the reaction mixture to rt. After 3h, reaction mixture quenched with water. Work up (H₂O/AcOEt) and purification afforded the title compound (120 mg) as a pale-yellow solid. ¹H-NMR (δ ppm, CDCl₃, 400 MHz): 8.99 (s, 1H), 8.41 (s, 1H), 7.46 (t, J 8.1, 1H), 7.08-7.01 (m, 2H), 6.21 (s, 1H), 3.53 (s, 3H), 2.58 (s, 3H), 1.60-1.51 (m, 1H), 0.98-0.88 (m, 2H), 0.70-0.60 (m, 2H). MS (m/z): 418.35 [M−H]⁻.

Example 95

N-{4-[4-chloro-5-cyclopropyl-3-(trifluoromethyl)-1H-pyrazol-1-yl]-3-fluorophenyl}-4-methyl-1,2,3-thiadiazole-5-carboxamide Following the general procedure-2, the title compound (120 mg) was prepared from 4-methyl-1,2,3-thiadiazole-5-carbonyl chloride (150 mg, 0.94 mmol) and intermediate 34 (150 g, 0.47 mmol) as a white solid. M.P.: 143-147° C. ¹H-NMR (δ ppm, DMSO-d₆, 400 MHz): 11.18 (s, 1H), 7.93 (dd, J 1.8, 12.5, 1H), 7.72 (t, J 8.6, 1H), 7.62 (d, J 9, 1H), 2.82 (s, 3H), 1.85-1.71 (m, 1H), 0.90-0.80 (m, 2H), 0.72-0.64 (m, 2H). MS (m/z): 444.04 [M−H]⁻.

Example 96

N-{4-[4-chloro-5-cyclopropyl-3-(trifluoromethyl)-1H-pyrazol-1-yl]-3-fluorophenyl}-2-(pyridin-2-yl)acetamide hydrochloride Following the general procedure-1, N-{4-[4-chloro-5-cyclopropyl-3-(trifluoromethyl)-1H-pyrazol-1-yl]-3-fluorophenyl}-2-(pyridin-2-yl)acetamide (150 mg) was prepared from 2-(pyridin-2-yl)acetic acid (97 mg, 0.56 mmol) and intermediate 34 (150 mg, 0.47 mmol) as a white solid and dissolved in THF. Saturated HCl in diethyl ether was added to this solution at 0° C. and stirred for 15 min. Solid that separated out was filtered and dried to give the title compound (25 mg) as a white solid. M.P.: 169-171° C. $^1$H-NMR (δ ppm, DMSO-$d_6$, 400 MHz): 11.03 (s, 1H), 8.75 (d, J 3.9, 1H), 8.29-8.20 (m, 1H), 8.88 (d, J 12.6, 1H), 7.79 (d, J 7.4, 1H), 7.73-7.69 (m, 1H), 7.67 (t, J 8.7, 1H), 7.51 (d, J 8.6, 1H), 4.17 (s, 2H), 1.80-1.70 (m, 1H), 0.90-0.80 (m, 2H), 0.72-0.60 (m, 2H). MS (m/z): 439.15 [M+H−HCl]$^+$.

Example 97

1-{4-[5-cyclopropyl-3-(trifluoromethyl)-1H-pyrazol-1-yl]-3-fluorophenyl}-3-(4-methylpyrimidin-5-yl) urea 4-methylpyrimidine-5-carboxylic acid (500 mg, 3.62 mmol) was dissolved in acetone, water mixture (20 ml and 2 ml) and cooled to −5° C. Ethyl choroformate (0.47 ml, 4.34 mmol) was added slowly to this mixture and stirred at same temperature for 30 mins. At this stage sodium azide (470 mg, 7.24 mmol) was added and stirred for 30 mins at the same temperature. Water was added to the reaction mixture and extracted with Et$_2$CO and ether was removed to obtain the crude. Crude was dissolved in dioxane, intermediate 33 (764 mg, 2.68 mmol) was added and refluxed for 30 mins. Work up (AcOEt:H$_2$O) followed by purification on 60-120 mesh silica gel using EA and Peteher (10:90) as eluent afforded the title compound (403 mg) as a pale yellow solid. M. P.: 197.8-202.4° C. $^1$H-NMR (δ ppm, DMSO-$d_6$, 400 MHz): 9.63 (s, 1H), 9.04 (s, 1H), 8.75 (s, 1H), 8.49 (s, 1H), 7.76 (dd, J 2.2, 12.8, 1H), 7.56 (t, J 8.7, 1H), 7.33 (dd, J 1.8, 8.7, 1H), 6.60 (s, 1H), 2.48 (s, 3H), 1.64-1.57 (m, 1H), 0.94-0.86 (m, 2H), 0.78-0.72 (m, 2H). MS (m/z): 419.26 [M−H]$^-$.

Example 98

N-{4-[5)-cyclopropyl-3-(trifluromethyl)-1H-pyrazol-1-yl]3-flurophenyl}-2,6-dichloro benzamide Following the general procedure-2, the title compound (15 mg) was prepared from intermediate 48 (220 mg, 0.74 mmol) and 2,6-dichloroaniline (100 mg, 0.62 mmol) as a white solid. M.P.: 175-180° C. $^1$H-NMR (δ ppm, DMSO-$d_6$, 400 MHz): 10.63 (s, 1H), 8.11-8.02 (m, 2H), 7.91 (t, J 7.8, 1H), 7.62 (d, J 8.2, 2H), 7.41 (t, J 8, 1H), 6.70 (s, 1H), 1.73-1.64 (m, 1H), 0.97-0.90 (m, 2H), 0.84-0.77 (m, 2H). MS (m/z): 455.94 [M−H]$^-$.

Example 99

4-[5-cyclopropyl-3-(trifluoromethyl)-1H-pyrazol-1-yl]-N-(2,3-difluorophenyl)-3-fluorobenzamide Following the general procedure-2, the title compound (100 mg) was prepared from intermediate 48 (200 mg, 0.67 mmol) and 2,3-difluoroaniline (216 mg, 0.65 mmol) as a white solid. M.P.: 175-180° C. $^1$H-NMR (δ ppm, DMSO-$d_6$, 400 MHz): 10.6 (s, 1H), 8.09 (d J 9.3, 1H), 8.01 (d, J 8.5, 1H), 7.88 (t, J 7.8, 1H), 7.49-7.41 (m, 1H), 7.39-7.31 (m, 1H), 7.29-7.22 (m, 1H), 6.70 (s, 1H), 1.71-1.62 (m, 1H), 0.99-0.91 (m, 2H), 0.82-0.74 (m, 2H). MS (m/z): 424.23 [M−H]$^-$.

Example 100

4-[5-cyclopropyl-3-(trifluoromethyl)-1H-pyrazol-1-yl]-N-(2,6-difluorophenyl)-3-fluorobenzamide Following the general procedure-2, the title compound (15 mg) was prepared from intermediate 48 (150 mg, 0.55 mmol) and 2,6-difluoroaniline (69 mg, 0.54 mmol) as a white solid. M.P.: 168.2-170.2° C. $^1$H-NMR (δ ppm, DMSO-$d_6$, 400 MHz): 10.46 (s, 1H), 8.09 (d, J 8, 1H), 8.03 (d, J 8.3, 1H), 7.89 (t, J 7.9, 1H), 7.50-7.40 (m, 1H), 7.24 (t, J 8.2, 2H), 6.70 (s, 1H), 1.75-1.65 (m, 1H), 0.98-0.90 (m, 2H), 0.81-0.74 (m, 2H). MS (m/z): 425.79 [M+H]$^+$.

Example 101

N-{6-[5-cyclopropyl-3-(trifluoromethyl)-1H-pyrazol-1-yl]pyridin-3-yl}-4-methyl-1,2,3-thiadiazole-5-carboxamide Following the general procedure-1, title compound (18 mg) was prepared from 4-methyl-1,2,3-thiadiazole-5-carboxylic acid (102 mg, 0.71 mmol) and intermediate 36 (120 mg, 0.45 mmol) as a pale yellow solid. M. P. 170-172° C. $^1$H-NMR (δ ppm, DMSO-$d_6$, 400 MHz): 11.15 (s, 1H), 8.86 (d, J 2.2, 1H), 8.36 (dd, J 2.4, 8.8, 1H), 7.85 (d, J 8.8, 1H), 6.66 (s, 1H), 2.85 (s, 3H), 2.60-2.50 (m, 1H), 1.08-0.98 (m, 2H), 0.82-0.74 (m, 2H). MS (nm/z): 392.79 [M−H−HCl]$^-$.

Example 102

N-{6-[5-cyclopropyl-3-(trifluoromethyl)-1H-pyrazol-1-yl]pyridin-3-yl}-4-methylthiazole-5-carboxamide hydrochloride Following the general procedure-2, N-{6-[5-cyclopropyl-3-(trifluoromethyl)-1H-pyrazol-1-yl]pyridin-3-yl}-4-methylthiazole-5-carboxamide (45 mg) was prepared from 4-methylthiazole-5-carbonyl chloride (132 mg, 0.82 mmol) and intermediate 36 (200 mg, 0.75 mmol) as a white solid and dissolved in THF. Saturated HCl in diethyl ether was added to this solution at 0° C. and stirred for 15 min. Solid that separated out was filtered and dried to give the title compound (69 mg) as a pale-yellow solid. M. P. 180-183° C. $^1$H-NMR (δ ppm, DMSO-$d_6$, 400 MHz): 10.68 (s, 1H), 9.18 (s, 1H), 8.85 (d, J 2.4, 1H), 8.35 (dd, J 2.5, 8.8, 1H), 7.79 (d, J 8.8, 1H), 6.64 (s, 1H), 2.64 (s, 3H), 2.51-2.40 (m, 1H), 1.10-0.95 (m, 2H), 0.81-0.74 (m, 2H). MS (m/z): 394.23 [M+H]$^+$.

Example 103

N-{6-[5-cyclopropyl-3-(trifluoromethyl)-1H-pyrazol-1-yl]pyridin-3-yl}-3,5-dimethylisoxazole-4-carboxamide Following the general procedure-1, the title compound (34 mg) was prepared from 3,5-dimethylisoxazole-4-carboxylic acid (101 mg, 0.71 mmol) and intermediate 36 (120 mg, 0.45 mmol) as a white solid M.P.: 139-142° C. $^1$H-NMR (δ ppm, DMSO-$d_6$, 400 MHz): 10.47 (s, 1H), 8.82 (d, J 2.5, 1H), 8.33 (dd, J 2.5, 8.8, 1H), 7.80 (d, J 8.8, 1H), 6.64 (s, 1H), 2.58 (s, 3H), 2.57-2.50 (m, 1H), 2.49 (s, 3H), 1.00-0.92 (m, 2H), 0.80-0.74 (m, 2H). MS (m/z): 389.67 [M−H]⁻.

Example 104

N-{6-[5-cyclopropyl-3-(trifluoromethyl)-1H-pyrazol-1-yl]pyridin-3-yl}-2-methylbenzamide Following the general procedure-1, the title compound (19 mg) was prepared from o-toluic acid acid (58 mg, 0.43 mmol) and intermediate 36 (80 mg, 0.26 mmol) as a white solid M.P.: 134-138° C. ¹H-NMR (δ ppm, DMSO-d₆, 400 MHz): 10.76 (s, 1H), 8.88 (d, J 2.4, 1H), 8.43 (dd, J 2.4, 8.9, 1H), 7.79 (d, J 8.8, 1H), 7.53 (d, J 7.3, 1H), 7.44-7.40 (m, 1H), 7.34-7.31 (m, 2H), 6.63 (s, 1H), 2.41 (s, 3H), 2.55-2.45 (m, 1H), 1.01-0.92 (m, 2H), 0.81-0.72 (m, 2H). MS (m/z): 384.63 [M−H]⁻.

Example 105

2-chloro-N-{6-[5-cyclopropyl-3-(trifluoromethyl)-1H-pyrazol-1-yl]pyridin-3-yl}benzamide hydrochloride Following the general procedure-2,2-chloro-N-{6-[5-cyclopropyl-3-(trifluoromethyl)-1H-pyrazol-1-yl]pyridin-3-yl}benzamide (65 mg) was prepared from 2-chlorobenzoyl chloride (107 mg, 0.61 mmol) and intermediate 36 (150 mg, 0.56 mmol) and dissolved in THF. Saturated HCl in diethyl ether was added to this solution at 0° C. and stirred for 15 min. Solid that separated out was filtered and dried to give the title compound (52 mg) as a pale-yellow solid. M. P. 145-148° C. ¹H-NMR (δ ppm, DMSO-d₆, 400 MHz): 10.99 (s, 1H), 8.86 (d, J 2, 1H), 8.41 (dd, J 2, 8.7, 1H), 7.81 (d, J 8.8, 1H), 7.66 (d, J 7, 1H), 7.60 (d, J 7.8, 1H), 7.54 (t, J 7.3, 1H), 7.48 (t, J 7.3, 1H), 6.64 (s, 1H), 2.60-2.48 (m, 1H), 1.04-0.92 (m, 2H), 0.82-0.70 (m, 2H). MS (m/z): 405.13 [M−H−HCl]⁻.

Example 106

N-(6-(5-cyclopropyl-3-(trifluoromethyl)-1H-pyrazol-1-yl)pyridin-3-yl)-2-fluorobenzamide Following the general procedure-1, the title compound (110 mg) was prepared from 2-fluorobenzoic acid (112 mg, 0.80 mmol) and intermediate 36 (150 mg, 0.50 mmol) as a white solid M.P.: 102-106° C. ¹H-NMR (δ ppm, DMSO-d₆, 400 MHz): 10.89 (s, 1H), 8.87 (d, J 2.4, 1H), 8.40 (dd, J 2.5, 8.8, 1H), 7.81 (d, J 8.8, 1H), 7.73 (dt, J 1.6, 7.5, 1H), 7.67-7.59 (m, 1H), 7.44-7.34 (m, 2H), 6.64 (s, 1H), 2.58-2.50 (m, 1H), 1.02-0.94 (m, 2H), 0.82-0.74 (m, 2H). MS (m/z): 389.09 [M−H]⁻.

Example 107

N-{6-[5-cyclopropyl-3-(trifluoromethyl)-1H-pyrazol-1-yl]pyridin-3-yl}-2,3-difluorobenzamide Following the general procedure-1, the title compound (22 mg) was prepared from 2,3-difluorobenzoic acid (113 mg, 0.70 mmol) and intermediate 36 (120 mg, 0.45 mmol) as a white solid. M.P.: 151-156° C. ¹H-NMR (δ ppm, DMSO-d₆, 400 MHz): 10.99 (s, 1H), 8.86 (s, 1H), 8.39 (d, J 8.7, 1H), 7.82 (d, J 8.7, 1H), 7.65 (q, J 8.6, 1H), 7.55 (t, J 6.4, 1H), 7.42-7.34 (m, 1H), 6.63 (s, 1H), 2.51-2.40 (m, 1H), 1.02-0.94 (m, 2H), 0.82-0.74 (m, 2H). MS (m/z): 406.94 [M−H]⁻.

Example 108

N-{6-[5-cyclopropyl-3-(trifluoromethyl)-1H-pyrazol-1-yl]pyridin-3-yl}-2,6-difluorobenzamide Following the general procedure-1, the title compound was prepared from 2,6-difluorobenzoic acid (113 mg, 70 mmol) and intermediate 36 (120 mg, 0.45 mmol) as a pale yellow solid. M. P. 157-162° C. ¹H-NMR (δ ppm, DMSO-d₆, 400 MHz): 11.30 (s, 1H), 8.83 (s, 1H), 8.39 (d, J 8.8, 1H), 7.83 (d, J 8.8, 1H), 7.65-7.60 (m, 1H), 7.29 (t, J 8, 2H), 6.64 (s, 1H), 2.58-2.48 (m, 1H), 1.00-0.94 (m, 2H), 0.81-0.75 (m, 2H). MS (m/z): 406.87 [M−H]⁻.

Example 109

N-{6-[5-cyclopropyl-3-(trifluoromethyl)-1H-pyrazol-1-yl]pyridin-3-yl}picolinamide Following the general procedure-1, the title compound (200 mg) was prepared from picolinic acid (146 mg, 1.2 mmol) and intermediate 36 (200 mg, 0.75 mmol) as a white solid M.P.: 159-162° C. ¹H-NMR (δ ppm, DMSO-d₆, 400 MHz): 11.19 (s, 1H), 9.09 (d, J 2.4, 1H), 8.78 (d, J 4, 1H), 8.62 (dd, J 2.6, 8.8, 1H), 8.19 (d, J 7.8, 1H), 8.10 (td, J 1.7, 7.7, 1H), 7.80 (d, J 8.8, 1H), 7.73-7.70 (m, 1H), 6.63 (s, 1H), 2.66-2.58 (m, 1H), 1.06-0.98 (m, 2H), 0.84-0.76 (m, 2H). MS (m/z): 372.09 [M−H]⁻.

Example 110

N-{6-[5-cyclopropyl-3-(trifluoromethyl)-1H-pyrazol-1-yl]pyridin-3-yl}-3-methylpicolinamide Following the general procedure-1, the title compound (140 mg) was prepared from 3-methylpicolinic acid (163 mg, 1.2 mmol) and intermediate 36 (200 mg, 0.75 mmol) as an off-white solid M.P.: 197-199° C. ¹H-NMR (δ ppm, DMSO-d₆, 400 MHz): 11.05 (s, 1H), 9.00 (d, J 2.5, 1H), 8.58-8.53 (m, 2H), 7.84 (d, J 7.8, 1H), 7.79 (d, J 8.8, 1H), 7.57-7.54 (m, 1H), 6.63 (s, 1H), 2.60 (s, 3H), 2.55-2.45 (m, 1H), 1.04-0.94 (m, 2H), 0.81-0.74 (m, 2H). MS (m/z): 385.53 [M−H]⁻.

Example 111

N-{6-[5-cyclopropyl-3-(trifluoromethyl)-1H-pyrazol-1-yl]pyridin-3-yl}nicotinamide hydrochloride Following the general procedure-1, N-{6-[5-cyclopropyl-3-(trifluoromethyl)-1H-pyrazol-1-yl]pyridin-3-yl}nicotinamide (200 mg) was prepared from nicotinic acid (132 mg, 1.2 mmol) and intermediate 36 (290 mg, 0.67 mmol) as a white solid and dissolved in THF. Saturated HCl in diethyl ether was added to this solution at 0° C. and stirred for 15 min. Solid that separated out was filtered and dried to give the title compound (192 mg) as a white solid M.P.: 211-213° C. ¹H-NMR (δ ppm, DMSO-d₆, 400 MHz): 11.11 (s, 1H), 9.27 (d, J 2, 1H), 8.98 (d, J 2, 1H), 8.89-8.86 (m, 1H), 8.59-8.51 (m, 1H), 8.48-8.46 (m, 1H), 7.83 (d, J 8.8, 1H), 7.79-7.73 (m, 1H), 6.65 (s, 1H), 2.58-2.50 (m, 1H), 1.04-0.94 (m, 2H), 0.81-0.74 (m, 2H). MS (m/z): 371.90 [M−H]⁻.

Example 112

N-{6-[5-cyclopropyl-3-(trifluoromethyl)-1H-pyrazol-1-yl]pyridin-3-yl}-2-methyl nicotinamide hydrochloride Following the general procedure-1, N-{6-[5-cyclopropyl-3-(trifluoromethyl)-1H-pyrazol-1-yl]pyridin-3-yl}-2-methylnicotinamide (35 mg) was prepared from 2-methylnicotinic acid (110 mg, 0.80 mmol) and intermediate 36 (150 mg, 0.5 mmol) as a white solid and dissolved in THF. Saturated HCl in diethyl ether was added to this solution at 0° C. and stirred for 15 min. Solid that separated out was filtered and dried to give the title compound (20 mg) as a white solid. M.P.: 241-245° C. $^1$H-NMR (δ ppm, DMSO-d$_6$, 400 MHz): 11.15 (s, 1H), 8.89 (d, J 2.5, 1H), 8.74 (d, J 4.1 1H), 8.42 (dd, J 2.6, 8.8, 1H), 8.32 (d, J 7.7, 1H), 7.83 (d, J 8.8, 1H), 7.72-7.64 (m, 1H), 6.65 (s, 1H), 2.70 (s, 3H), 2.58-2.50 (m, 1H), 1.00-0.95 (m, 2H), 0.81-0.76 (m, 2H). MS (m/z): 385.64 [M–H–HCl]$^-$.

Example 113

N-{6-[5-cyclopropyl-3-(trifluoromethyl)-1H-pyrazol-1-yl]pyridin-3-yl}isonicotinamide hydrochloride Following the general procedure-1, N-{6-[5-cyclopropyl-3-(trifluoromethyl)-1H-pyrazol-1-yl]pyridin-3-yl}isonicotinamide (160 mg) was prepared from isonicotinic acid (132 mg, 1.2 mmol) and intermediate 36 (290 mg, 0.67 mmol) as an off-white solid and dissolved in THF. Saturated HCl in diethyl ether was added to this solution at 0° C. and stirred for 15 min. Solid that separated out was filtered and dried to give the title compound (137 mg) as an yellow solid M.P.: 186-188° C. $^1$H-NMR (δ ppm, DMSO-d$_6$, 400 MHz): 11.23 (s, 1H), 8.99 (d, J 2.5, 1H), 8.94 (d, J 6.2, 2H), 8.47 (dd, J 2.5, 8.8, 1H), 8.14 (d, J 6.2, 2H), 7.85 (d, J 8.8, 1H), 6.65 (s, 1H), 2.60-2.50 (m, 1H), 1.04-0.94 (m, 2H), 0.80-0.73 (m, 2H). MS (m/z): 371.65 [M–H]$^-$.

Example 114

N-{6-[5-cyclopropyl-3-(trifluoromethyl)-1H-pyrazol-1-yl]pyridin-3-yl}-3-fluoroisonicotinamide Following the general procedure-1, the title compound (90 mg) was prepared from 3-fluoroisonicotinic acid (113 mg, 0.80 mmol) and intermediate 36 (150 mg, 0.5 mmol) as a brown solid M.P.: 162-164° C. $^1$H-NMR (δ ppm, DMSO-d$_6$, 400 MHz): 11.16 (s, 1H), 8.86 (d, J 2.5, 1H), 8.80 (d, J 1, 1H), 8.64-8.62 (m, 1H), 8.39 (dd, J 2.6, 8.8, 1H), 7.84 (d, J 8.8, 1H), 7.76 (t, J 5.4, 1H), 6.65 (s, 1H), 2.592.50 (m, 1H), 1.05-0.97 (m, 2H), 0.81-0.74 (m, 2H). MS (m/z): 389.60 [M–H]$^-$.

Example 115

3,5-dichloro-N-{6-[5-cyclopropyl-3-(trifluoromethyl)-1H-pyrazol-1-yl]pyridin-3-yl}isonicotinamide Following the general procedure-2, the title compound (45 mg) was prepared from intermediate 36 (200 mg, 0.75 mmol) and 3,5-dichloroisonicotinic acid (390 mg, 1.56 mmol) as a pale-yellow solid. M.P.: 223-225° C. $^1$H-NMR (δ ppm, DMSO-d$_6$, 400 MHz): 11.49 (s, 1H), 8.84 (s, 2H), 8.80 (d, J 2.6, 1H), 8.37 (dd, J 2.6, 8.8, 1H), 7.86 (d, J 8.8, 1H), 6.65 (s, 1H), 2.60-2.52 (m, 1H), 1.02-0.94 (m, 2H), 0.82-0.74 (m, 2H). MS (m/z): 441.94 [M–H]$^-$.

Example 116

N-{6-[5-cyclopropyl-3-(trifluoromethyl)-1H-pyrazol-1-yl]pyridin-3-yl}-4-methylpyrimidine-5-carboxamide Following the general procedure-1, the title compound (17 mg) was prepared from intermediate 36 (200 mg, 0.75 mmol) and intermediate 53 (123 mg, 0.89 mmol) as an off-white solid. M.P.: 159.2-160.3° C. $^1$H-NMR (δ ppm, DMSO-d$_6$, 400 MHz): 11.08 (s, 1H), 9.17 (s, 1H), 8.96 (s, 1H), 8.86 (s, 1H), 8.45-8.38 (m, 1H), 7.83 (d, J 6.9, 1H), 6.65 (s, 1H), 2.61 (s, 3H), 2.50-2.40 (m, 1H), 1.02-0.90 (m, 2H), 0.86-0.70 (m, 2H). MS (m/z): 386.77 [M–H]$^-$.

Example 117

N-{6-[5-cyclopropyl-3-(trifluoromethyl)-1H-pyrazol-1-yl]pyridin-3-yl}-2-(pyridin-2-yl)acetamide hydrochloride Following the general procedure-1, N-{6-[5-cyclopropyl-3-(trifluoromethyl)-1H-pyrazol-1-yl]pyridin-3-yl}2-(pyridin-2-yl)acetamide (200 mg) was prepared from 2-(pyridin-2-yl)acetic acid (207 mg, 1.2 mmol) and intermediate 36 (200 mg, 0.75 mmol) as an off-white solid and dissolved in THF. Saturated HCl in diethyl ether was added to this solution at 0° C. and stirred for 15 min. Solid that separated out was filtered and dried to give the title compound (210 mg) as an Off-white solid M.P.: 179-181° C. $^1$H-NMR (δ ppm, DMSO-d$_6$, 400 MHz): 11.38 (s, 1H), 8.90 (dd, J 0.8, 5.7, 1H), 8.82 (d, J 2.5, 1H), 8.54 (t, J 6.7, 1H) 8.30 (dd, J 2.6, 8.8, 1H), 8.06 (d, J 8, 1H), 7.96 (t, J 6.7, 1H), 7.77 (d, J 8.8, 1H), 6.63 (s, 1H), 4.41 (s, 2H), 2.50-2.41 (m, 1H), 1.00-0.91 (m, 2H), 0.79-0.72 (m, 2H). MS (m/z): 385.60 [M–H–HCl]$^-$.

Example 118

N-{6-[5-cyclopropyl-3-(trifluoromethyl)-1H-pyrazol-1-yl]pyridin-3-yl}-2-(pyridin-4-yl)acetamide hydrochloride Following the general procedure-1, N-{6-[5-cyclopropyl-3-(trifluoromethyl)-1H-pyrazol-1-yl]pyridin-3-yl}-2-(pyridin-4-yl)acetamide (280 mg) was prepared from 4-(pyridin-4-yl)acetic acid (310 mg, 1.78 mmol) and intermediate 36 (300 mg, 1.12 mmol) as an off-white solid and dissolved in THF. Saturated HCl in diethyl ether was added to this solution at 0° C. and stirred for 15 min. Solid that separated out was filtered and dried to give the title compound (68 mg) as an Off-white solid M.P.: 185.2-188° C. $^1$H-NMR (δ ppm, DMSO-d$_6$, 400 MHz): 11.26 (s, 1H), 8.87 (d, J 6.6, 2H), 8.81 (d, J 2.5, 1H), 8.30 (dd, J 2.6, 8.8, 1H), 8.06 (d, J 6.6, 2H), 7.76 (d, J 8.8, 1H), 6.62 (s, 1H), 4.19 (s, 2H), 2.52-2.42 (s, 1H), 1.00-0.91 (m, 2H), 0.80-0.72 (m, 2H). MS (m/z): 385.53 [M–H–HCl]$^-$.

Example 119

N-{4-[4-chloro-5-cyclopropyl-3-(trifluoromethyl)-1H-pyrazol-1-yl]-3-fluorophenyl}-4-methylpyrimidine-5-carboxamide Step-1: Intermediate 34 (1.83 g, 5.72 mmol) and t-Butylacetoacetate (1.9 ml, 11.4 mmol) were dissolved in xylene (5 ml) and heated to 145° C. f° r 90 mins. Reaction mixture was cooled to rt to obtain a solid. Solid that formed was filtered, washed with petether and dried to obtain N-{4-[4-chloro-5-cyclopropyl-3-(trifluoromethyl)-1H-pyrazol-1-yl]phenyl}-3-oxobutanamide (1.6 g).

Step-2: N-{4-[4-chloro-5-cyclopropyl-3-(trifluoromethyl)-1H-pyrazol-1-yl]phenyl}-3-oxobutanamide (1.6 g, 3.98 mmol) and N,N-Dimethylformamide dimethylacetal (2.6 g, 21.9 mmol) were mixed and stirred at rt for overnight. Workup (AcOEt/H$_2$O) followed by purification on 60-120 mesh silicagel using AcOEt and Peteher (1:1) as eluent afforded N-{4-[4-chloro-5-cyclopropyl-3-(trifluoromethyl)-1H-pyrazol-1-yl]phenyl}-2-[(dimethylamino)methylene]-3-oxobutanamide (1.3 g).

Step-3: N-{4-[4-chloro-5-cyclopropyl-3-(trifluoromethyl)-1H-pyrazol-1-yl]phenyl}-2-[(dimethylamino)methylene]-3-oxobutanamide (1.3 g, 2.8 mmol) and formamidine acetate (354 mg, 3.4 mmol) were dissolved in ethanol and added NaOEt (202 mg, 3.4 mmol). The above mixture was refluxed for 3 h. Ethanol was removed on rotavapour and worked up (H2O/AcOEt) to obtain the crude. Crude was purified by column on 60-120 mesh silica gel using AcOEt and Peteher (35:65) as eluent to obtain the title compound (150 mg) as a pale-yellow solid. M.P.: 183-185° C. $^1$H-NMR (δ ppm, DMSO-d$_6$, 400 MHz): 11.11 (s, 1H), 9.17 (s, 1H), 8.95 (s, 1H), 7.99 (dd, J 1.8, 12.4, 1H), 7.71 (t, J 8.7, 1H), 7.62 (d, J 8.7, 1H), 2.60 (s, 3H), 1.81-1.72 (m, 1H), 0.89-0.81 (m, 2H), 0.74-0.67 (m, 2H). MS (m/z): 405.89 [M+H−Cl]$^+$.

Example 120

1-{6-[3-cyclopropyl-5-(trifluoromethyl)-1H-pyrazol-1-yl]pyridin-3-yl}-3-(4-methylthiazol-5-yl)urea 4-methylthiazole-5-carboxylic acid (300 mg, 2.09 mmol) was dissolved in acetone, water mixture (15 ml and 1.5 ml) and cooled to −5° C. Ethyl choroformate (270 mg, 2.5 mmol) was added slowly to this mixture and stirred at same temperature for 30 mins. At this stage sodium azide (270 mg, 4.2 mmol) was added and stirred for 30 mins at the same temperature. Water was added to the reaction mixture and extracted with Et$_2$CO and ether was removed to obtain the crude. Crude was dissolved in dioxane, intermediate 36 (240 mg, 0.89 mmol) was added and refluxed for 30 mins. Work up (AcOEt:H$_2$O) followed by purification on 60-120 mesh silica gel using EA and Peteher (45:50) as eluent afforded the title compound (200 mg) as a pale yellow solid. M. P.: 244-247° C. $^1$H-NMR (δ ppm, DMSO-d$_6$, 400 MHz): 9.49 (s, 1H), 9.45 (s, 1H), 8.60-8.53 (m, 2H), 8.20 (m, 1H), 7.70 (m, 1H), 6.60 (s, 1H), 2.30 (s, 3H), 1.84-1.74 (m, 1H), 1.06-0.96 (m, 2H), 0.82-0.72 (m, 2H). MS (m/z): 409.06 [M+H]$^+$.

Example 121

6-[5-cyclopropyl-3-(trifluoromethyl)-1H-pyrazol-1-yl]-N-(2,3-difluorophenyl)nicotinamide Following the general procedure-2, the title compound (100 mg) was prepared from intermediate 50 (220 mg, 0.74 mmol) and 2,3-difluoroaniline (100 mg, 0.77 mmol) as a white solid. M.P.: 155-160° C. $^1$H-NMR (δ ppm, DMSO-d$_6$, 400 MHz): 10.66 (s, 1H), 9.10 (d, J 2.2, 1H), 8.6 (dd, J 2.3, 8.6, 1H), 8.00 (d J 8.6, 1H), 7.47-7.44 (m, 1H), 7.35-7.30 (m, 1H), 7.29-7.23 (m, 1H), 6.74 (s, 1H), 2.90-2.72 (m, 1H), 1.10-1.00 (m, 2H), 0.90-0.81 (m, 2H). MS (m/z): 407.22 [M−H]$^-$.

Example 122

6-[5-cyclopropyl-3-(trifluoromethyl)-1H-pyrazol-1-yl]-N-(2,6-difluorophenyl) nicotinamide Following the general procedure-2, the title compound (36 mg) was prepared from intermediate 50 (150 mg, 0.46 mmol) and 2,6-difluoroaniline (61 mg, 0.46 mmol) as a white solid. M.P.: 192-194° C. $^1$H-NMR (δ ppm, DMSO-d$_6$, 400 MHz): 10.52 (s, 1H), 9.11 (d, J 2.1, 1H), 8.58 (dd, J 2.1, 8.6, 1H), 8.02 (d, J 8.4, 1H), 7.50-7.40 (m, 1H), 7.24 (t, J 8.12, 2H), 6.75 (s, 1H), 2.80-2.70 (m, 1H), 1.09-1.00 (m, 2H), 0.88-0.80 (m, 2H).

Example 123

N-{6-[4-chloro-5-cyclopropyl-3-trifluoromethyl-1H-pyrazol-1-yl]pyridin-3-yl}-4-methylthiazole-5-carboxamide Following the general procedure-2, the title compound (21 mg) was prepared from 4-methylthiazole-5-carbonyl chloride (52 mg, 0.36 mmol) and intermediate 37 (100 mg, 0.36 mmol) as a white solid. M.P.: 144-149° C. $^1$H-NMR (δ ppm, DMSO-d$_6$, 400 MHz): 10.68 (s, 1H), 9.17 (s, 1H), 8.87 (s, 1H), 8.37 (d, J 7.32, 1H), 7.77 (d, J 8.2, 1H), 2.65 (s, 3H), 2.21-2.08 (m, 1H), 1.93-1.84 (m, 2H), 1.71-1.60 (m, 2H). MS (m/z): 425.95 [M−H]$^-$.

Example 124

N-{2-[5-cyclopropyl-3-(trifluoromethyl)-1H-pyrazol-1-yl]pyrimidin-5-yl}-2,6-difluorobenzamide Following the general procedure-2, the title compound (31 mg) was prepared from intermediate 38 (150 mg, 0.55 mmol) and 2,6-difluoroaniline (98 mg, 0.46 mmol) as a white solid. M.P.: 279.7-281.2° C. $^1$H-NMR (δ ppm, DMSO-d$_6$, 400 MHz): 11.54 (s, 1H), 9.24 (s, 2H), 7.71-7.62 (m, 1H), 7.31 (t, J 8.1, 2H), 6.67 (s, 1H), 2.60-2.50 (m, 1H), 1.02-0.94 (m, 2H), 0.82-0.74 (m, 2H). MS (n/z): 409.90 [M+H]$^+$.

Example 125

N-{4-[5-(fluoromethyl)-3-(trifluoromethyl)-1H-pyrazol-1-yl]phenyl}-4-methyl thiazole-5-carboxamide Following the general procedure-1, the title compound (110 mg) was prepared from 4-methylthiazole-5-carboxylic acid (165 mg, 1.15 mmol) and intermediate 39 (150 mg, 0.58 mmol) as an off-white solid M.P.: 123.9-125.3° C. $^1$H-NMR (δ ppm, DMSO-d$_6$, 400 MHz): 10.51 (s, 1H), 9.15 (s, 1H), 7.88 (d, J 8.9, 21-), 7.57 (d, J 8.9, 2H), 7.23 (d, J 2.6, 1H), 5.53 (d, J 48.04, 2H), 2.62 (s, 3H). MS (m/z): 382.86 [M−H]$^-$.

Example 126

N-{4-[5-(difluoromethyl)-3-(trifluoromethyl)-1H-pyrazol-1-yl]phenyl}-4-methyl thiazole-5-carboxamide Following the general procedure-1, the title compound (70 mg) was prepared from 4-methylthiazole-5-carboxylic acid (132 mg, 0.9 mmol) and intermediate 40 (150 mg, 0.58 mmol) as a white solid M.P.: 124-126° C. $^1$H-NMR (δ ppm, DMSO-d$_6$, 400 MHz): 10.53 (s, 1H), 9.15 (s, 1H), 7.88 (d, J 8.8, 2H), 7.59 (d, J 8.8, 2H), 7.42 (s, 1H), 7.26 (t, J 52.9, 1H), 2.62 (s, 3H). MS (m/z): 400.58 [M–H]$^-$.

Example 127

3,5-dichloro-N-[4-(3,5-dicyclopropyl-1H-pyrazol-1-yl)-3-fluorophenyl]isonicotinamide Following the general procedure-2, the title compound (21 mg) was prepared from intermediate 28 (500 mg, 1.94 mmol) and 2,6-dichloroisonicotinic acid (380 mg, 1.97 mmol) as a yellow solid. M.P.: 279.7-281.2° C. $^1$H-NMR (δ ppm, DMSO-d$_6$, 400 MHz): 11.37 (s, 1H), 8.83 (s, 2H), 7.81 (dd, J 2, 12.1, 1H), 7.58-7.48 (m, 2H), 5.76 (s, 1H), 1.89-1.80 (m, 1H), 1.50-1.41 (m, 1H), 0.90-0.78 (m, 4H), 0.66-0.54 (m, 4H). MS (m/z): 431.02 [M–H]$^-$ Example 128

N-(2-chloro-6-fluorophenyl)-4-[5-cyclopropyl-3-(trifluoromethyl)-1H-pyrazol-1-yl]-3-fluorobenzamide Following the general procedure-2, the title compound (21 mg) was prepared from intermediate 48 (500 mg, 1.94 mmol) and 2-Chloro-6-fluoroaniline (380 mg, 1.97 mmol) as a white solid. M.P.: 148-152° C. $^1$H-NMR (δ ppm, DMSO-d$_6$, 400 MHz): 10.51 (s, 1H), 8.09 (d, J 10.7, 1H), 8.04 (d, J 8.1, 1H), 7.90 (t, J 7.8, 1H), 7.50-7.35 (m, 3H), 6.70 (s, 1H), 1.73-1.65 (m, 1H), 0.97-0.90 (m, 2H), 0.80-0.73 (m, 2H). MS (m/z): 442.08 [M+H]$^+$.

Example 129

N-{2-[5-cyclopropyl-3-(trifluoromethyl)-1H-pyrazol-1-yl]pyrimidin-5-yl}-4-methyl thiazole-5-carboxamide Following the general procedure-2, the title compound (86 mg) was prepared from intermediate 38 (100 mg, 0.37 mmol) and 4-methylthiazole-5-carbonyl chloride (72 mg, 0.45 mmol) as a white solid, M.P.: 148-152° C. $^1$H-NMR (δ ppm, DMSO-d$_6$, 400 MHz): 10.81 (s, 1H), 9.23 (s, 2H), 9.20 (s, 1H), 6.67 (s, 1H), 2.66 (s, 3H), 2.55-2.46 (m, 1H), 1.06-0.97 (m, 2H), 0.81-0.74 (m, 2H). MS (m/z): 395.04 [M+H]$^+$.

Example 130

N-{4-[5-cyclopropyl-3-(trifluoromethyl)-1H-pyrazol-1-yl]-3,5-difluorophenyl}-4-methylpyrimidine-5-carboxamide Step-1: Intermediate 35 (1 g, 3.3 mmol) and t-Butylacetoacetate (782 mg, 4.94 mmol) were dissolved in xylene (3 ml) and heated to 145° C. for 90 mins. Reaction mixture was cooled to rt to obtain a solid. Solid that formed was filtered, washed with petether and dried to obtain N-{4-[5-cyclopropyl-3-(trifluoromethyl)-1H-pyrazol-1-yl]-3,5-difluorophenyl}-3-oxobutanamide (1.0 g).
Step-2: N-{4-[5-cyclopropyl-3-(trifluoromethyl)-1H-pyrazol-1-yl]-3,5-difluorophenyl}-3-oxobutanamide (1 g, 2.6 mmol) and N,N-Dimethylformamide dimethylacetal (1.7 g, 14.2 mmol) were mixed and stirred at rt for overnight. Workup (AcOEt/H$_2$O) followed by purification on 60-120 mesh silicagel using AcOEt and Peteher (1:1) as eluent afforded N-{4-[5-cyclopropyl-3-(trifluoromethyl)-1H-pyrazol-1-yl]-3,5-difluorophenyl}-2-[(dimethylamino)methylene]-3-oxobutanamide (0.7 g).
Step-3: N-{4-[5-cyclopropyl-3-(trifluoromethyl)-1H-pyrazol-1-yl]-3,5-difluorophenyl}-2-[(dimethylamino)methylene]-3-oxobutanamide (700 mg, 1.6 mmol) and formamidine acetate (282 mg, 2.7 mmol) were dissolved in ethanol and added NaOEt (120 mg, 3.4 mmol). The above mixture was refluxed for 3 hr. Ethanol was removed on rotavapour and worked up (H$_2$O/AcOEt) to obtain the crude. Crude was purified by column on 60-120 mesh silica gel using AcOEt and Petether (35:65) as eluent to obtain the title compound (34 mg) as a pale-yellow solid. M.P.: 147-150° C. $^1$H-NMR (δ ppm, DMSO-d$_6$, 400 MHz): 11.25 (s, 1H), 9.18 (s, 1H), 8.96 (s, 1H), 7.73 (d, J 9.9, 21H), 6.69 (s, 1H), 2.61 (s, 3H), 1.65-1.56 (m, 1H), 0.95-0.86 (m, 2H), 0.80-0.72 (m, 2H). MS (m/z): 424.09 [M+H]$^+$.

Example 131

N-{4-[5-cyclopropyl-3-(trifluoromethyl)-1H-pyrazol-1-yl]-3-fluorophenyl}-1-phenylcyclobutanecarboxamide Following the general procedure-2, the title compound (26 mg) was prepared from intermediate 33 (100 mg, 0.37 mmol) and intermediate 61 (72 mg, 0.45 mmol) as a white solid. M.P.: 72-76° C. $^1$H-NMR (δ ppm, DMSO-d$_6$, 400 MHz): 9.85 (s, 1H), 7.89 (d, J 11.4, 1H), 7.62-7.51 (m, 2H), 7.49-7.43 (m, 2H), 7.36 (t, J 7.8, 2H), 7.28-7.22 (m, 1H), 6.58 (s, 1H), 2.91-2.80 (m, 2H), 1.90-1.78 (m, 2H), 1.60-1.50 (m, 1H), 0.90-0.80 (m, 2H), 0.79-0.68 (m, 2H). 444.18 [M+H]$^+$ Example 132

N-{4-[5-cyclopropyl-3-(trifluoromethyl)-1H-pyrazol-1-yl]-3-fluorophenyl}-4-methyloxazole-5-carboxamide Following the general procedure-2, the title compound (26 mg) was prepared from intermediate 33 (100 mg, 0.37 mmol) and 4-Methyloxazole-5-carboxylic acid (70 mg, 0.55 mmol) as a white solid. M.P.: 148-150° C. $^1$H-NMR (δ ppm, DMSO-d$_6$, 400 MHz): 10.74 (s, 1H), 8.59 (s, 1H), 8.0 (d, J 12.6, 1H), 7.77 (d, J 8.4, 1H), 7.63 (t, J 8.8, 1H), 6.61 (s, 1H), 2.44 (s, 3H), 2.66-2.58 (m, 1H), 0.94-0.84 (m, 2H), 0.80-0.71 (m, 2H). MS (m/z): 395.04 [M+H]$^+$.

Example 133

N-{2-[5-cyclopropyl-3-(trifluoromethyl)-1H-pyrazol-1-yl]pyrimidin-5-yl}-4-methylpyrimidine-5-carboxamide Step-1: Intermediate 38 (1.1 g, 4.08 mmol) and t-Butylacetoacetate (1.29 g, 8.17 mmol) were dissolved in xylene (2.9 ml) and heated to 145° C. for 90 mins. Reaction mixture was cooled to rt to obtain a solid. Solid that formed was filtered, washed with petether and dried to obtain N-{2-[5-cyclopropyl-3-(trifluoromethyl)-1H-pyrazol-1-yl]pyrimidin-5-yl}-3-oxobutanamide (445 mg).
Step-2: N-{2-[5-cyclopropyl-3-(trifluoromethyl)-1H-pyrazol-1-yl]pyrimidin-5-yl}-3-oxobutanamide (445 mg, 1.3 mmol) and N,N-Dimethylformamide dimethylacetal (859 mg, 7.2 mmol) were mixed and stirred at rt for overnight. Workup (AcOEt/H$_2$O) followed by purification on 60-120 mesh silicagel using AcOEt and Petether (1:1) as eluent afforded N-{2-[5-cyclopropyl-3-(trifluoromethyl)-1H-pyrazol-1-yl]pyrimidin-5-yl}-2-[(dimethylamino)methylene]-3-oxobutanamide (0.3 g).

Step-3: N-{2-[5-cyclopropyl-3-(trifluoromethyl)-1H-pyrazol-1-yl]pyrimidin-5-yl}-2-[(dimethylamino)methylene]-3-oxobutanamide (0.3 g, 0.78 mmol) and formamidine acetate (98 mg, 0.94 mmol) were dissolved in ethanol and added NaOEt (60 mg, 0.94 mmol). The above mixture was refluxed for 3 h. Ethanol was removed on rotavapour and worked up (H$_2$O/AcOEt) to obtain the crude. Crude was purified by column on 60-120 mesh silica gel using AcOEt and Petether (1:1) as eluent to obtain the title compound (12 mg) as a brown solid. M.P.: 201-203° C. $^1$H-NMR (δ ppm, DMSO-d$_6$, 400 MHz): 11.29 (s, 1H), 9.26 (s, 2H), 9.19 (s, 1H), 8.99 (s, 1H), 6.68 (s, 1H), 2.64 (s, 3H), 2.55-2.49 (m, 1H), 1.02-0.94 (m, 2H), 0.83-0.75 (m, 2H). MS (m/z): 389.93 [M+H]$^+$.

Example 134

4-[5-cyclopropyl-3-(trifluoromethyl)-1H-pyrazol-1-yl]-3-fluoro-N-(4-methylpyrimidin-5-yl)benzamide Following the general procedure-2, the title compound (17 mg) was prepared from intermediate 48 (120 mg, 0.41 mmol) and 4-methylpyrimidin-5-amine (50 mg, 0.46 mmol) as a white solid. M.P.: 150-152° C. $^1$H-NMR (δ ppm, DMSO-d$_6$, 400 MHz): 10.52 (s, 1H), 8.94 (s, 1H), 8.76 (s, 1H), 8.11 (dd, J 1.6, 10.7, 1H), 8.04 (d, J 8.1, 1H), 7.91 (t, J 7.7, 1H), 6.70 (s, 1H), 2.48 (s, 3H), 1.70-1.62 (m, 1H), 0.95-0.88 (m, 2H), 0.83-0.77 (m, 2H). MS (m/z): 406.03 [M+H]$^+$.

Example 135

N-{4-[3-cyclopropyl-5-(difluoromethyl)-1H-pyrazol-1-yl]-3-fluorophenyl}-2,6-difluorobenzamide and N-{4-[5-cyclopropyl-3-(difluoromethyl)-1H-pyrazol-1-yl]-3-fluorophenyl}-2,6-difluorobenzamide Following the general procedure-2, the title compound (60 mg) was prepared from intermediate 65 (90 mg, 0.36 mmol) and 2,6-difluorobenzoic acid (120 mg, 0.76 mmol) as a white solid. M.P.: 168-171° C. $^1$H-NMR (δ ppm, DMSO-d$_6$, 400 MHz): 11.28 (s, 0.64H), 11.26 (s, 0.36H), 7.92 (d, J 12.4, 0.64H), 7.85 (d, J 12.4, 0.36H), 7.66-7.53 (m, 3H), 7.29 (t, J 8.2, 1.28H), 7.19 (t, J 8.2, 0.72H), 7.00 (t, J 53.3, 0.36H), 6.97 (t, J 53.3, 0.64H), 6.57 (s, 0.36H), 6.38 (s, 0.64H), 2.0-1.94 (m, 0.36H), 1.64-1.56 (m, 0.64H), 0.96-0.86 (m, 2H), 0.75-0.69 (m, 2H). MS (m/z): 408.20 [M+H]+.

BIOLOGICAL ASSAYS

The properties of the compounds of this invention may be confirmed by a number of biological/pharmacological assays. The biological/pharmacological assay which can be been carried out with the compounds according to the invention and/or their pharmaceutically acceptable salts is exemplified below. Similarly the compounds of the present invention may also be tested using other assays, such as cytokine (IL-2, IL-4, IL-5, IL-10, IL-12, TNF alpha, interferon gamma etc.) estimation in Jurkat as well as human PBMCs The compounds of the invention may also be tested in various aminal models to establish the various therapeutic potential of of the compounds of this invention.

1. In-Vitro CRAC Channel Inhibition Assays

1A. In-Vitro CRAC Channel Inhibition Assay in Jurkat Cells

Inhibition of CRAC channels was determined following thapsigargin (Sigma, Cat # T9033) induced endoplasmic calcium release in Jurkat cells. (see Yasurio Yonetoky et. al Bio. & Med Chem. 14 (2006) 4750-4760). Cells were centrifuged and re-suspended in equal volumes of Ca$^{2+}$ and Mg$^{2+}$ free Hanks buffer and Fluo-8 NW dye (ABD Bioquest, Inc., Sunnyvale, Calif.) loading solution at 2×10$^5$ cells/100 μl/well in 96-well black plate. Plate is incubated at 37° C./5% CO$_2$ for 30 min followed by further 15 min incubation at room temperature. Test compounds (DMSO stocks diluted in Ca$^{2+}$ and Mg$^{2+}$ free Hanks buffer) at desired concentrations were added to the wells and incubated for 15 min. Thapsigargin (1 μM final concentration) was added to the wells and incubated for 15 min to inhibit the Sarco-endoplasmic reticulum Ca$^{2+}$ ATPase pump thereby depleting endoplasmic calcium and raising cytosolic calcium concentrations. Store-operated calcium entry was initiated by adding extracellular Ca$^{2+}$ to a final concentration of 1.8 mM. Fluorescence was monitored over 5 min on a plate reader (BMG Labtech., Germany) with excitation at 485 nm and an emission wavelength at 520 nm. Data were analyzed using GraphPad Prism. IC$_{50}$ for each compound was determined based on the percent inhibition of thapsigargin-induced calcium influx into cells. The results are as provided in Table 1A.

TABLE 1A

| Compound | % inhibition (1 uM) | IC50 (nM) |
|---|---|---|
| Example 1 | 99 | 62.44 |
| Example 2 | 100 | 206.7 |
| Example 3 | 72.16 | — |
| Example 4 | 100 | 256.1 |
| Example 5 | 48.52 | — |
| Example 6 | 41.31 | — |
| Example 7 | 98.98 | 36.35 |
| Example 8 | 100 | — |
| Example 9 | 98.6 | — |
| Example 10 | 49.47 | — |
| Example 11 | 71.86 | — |
| Example 12 | 90.8 | — |
| Example 13 | 37.20 | — |
| Example 14 | 25.94 | — |
| Example 15 | 94.00 | 141.3 |
| Example 16 | 92.85 | 243.9 |
| Example 17 | 87.50 | 129.6 |
| Example 18 | 82.81 | — |
| Example 19 | 73.52 | 456.6 |
| Example 20 | 70.2 | — |
| Example 21 | 78.41 | — |
| Example 22 | 73.44 | 968.1 |
| Example 23 | 53.75 | — |
| Example 24 | 38.0 | — |
| Example 25 | 28.97 | — |
| Example 26 | 42.97 | — |
| Example 27 | 91.16 | — |
| Example 28 | 100 | 60.31 |
| Example 29 | 100 | — |
| Example 30 | 35.12 | — |
| Example 31 | 76.97 | — |
| Example 32 | 63.62 | — |
| Example 33 | 93.11 | 145.1 |
| Example 34 | 21.51 | — |
| Example 35 | 100 | 184.6 |
| Example 36 | 68.18 | 223.5 |
| Example 37 | 82.24 | 181.1 |
| Example 38 | 52.71 | — |
| Example 39 | 41.26 | 851.4 |

TABLE 1A-continued

| Compound | % inhibition (1 uM) | IC50 (nM) |
|---|---|---|
| Example 40 | 12.62 | — |
| Example 41 | 0 | — |
| Example 42 | 26.19 | — |
| Example 43 | 9.34 | — |
| Example 44 | 63.44 | — |
| Example 45 | 72.26 | 436.1 |
| Example 46 | 0.26 | — |
| Example 47 | 10.38 | — |
| Example 48 | 12.34 | — |
| Example 49 | 100 | 65.49 |
| Example 50 | 29.77 | — |
| Example 51 | 0 | — |
| Example 52 | 100 | 183.6 |
| Example 53 | 99.42 | 72.03 |
| Example 54 | 0 | — |
| Example 55 | 100 | — |
| Example 56 | 100 | 63.17 |
| Example 57 | 83.77 | 124.5 |
| Example 58 | 40.53 | — |
| Example 59 | 0.57 | — |
| Example 60 | 83.73 | 119.7 |
| Example 61 | 100 | — |
| Example 62 | 100 | — |
| Example 63 | 39.07 | — |
| Example 64 | 100 | — |
| Example 65 | 97.89 | — |
| Example 66 | 100 | 254.7 |
| Example 67 | 100 | 20.37 |
| Example 68 | 61.47 | — |
| Example 69 | 74.57 | — |
| Example 70 | 68.9 | — |
| Example 71 | 100 | 604.3 |
| Example 72 | 100 | 48.22 |
| Example 73 | 67.98 | — |
| Example 74 | 100 | 48.02 |
| Example 75 | 0 | — |
| Example 76 | 92.31 | 269.0 |
| Example 77 | 44.02 | — |
| Example 78 | 100 | 34.11 |
| Example 79 | 100 | 123.8 |
| Example 80 | 81.63 | 194 |
| Example 81 | 56.06 | — |
| Example 82 | 100 | 35.72 |
| Example 83 | 100 | 48.17 |
| Example 84 | 100 | 20.79 |
| Example 85 | 76.61 | — |
| Example 86 | 86.64 | 147.2 |
| Example 87 | 91.57 | 32.59 |
| Example 88 | 100 | 98.58 |
| Example 89 | 100 | 205.7 |
| Example 90 | 100 | 232.0 |
| Example 91 | 100 | 159.1 |
| Example 92 | 95.79 | 159.3 |
| Example 93 | 90 | 81.25 |
| Example 94 | 45.44 | — |
| Example 95 | 100 | — |
| Example 96 | 18 | — |
| Example 97 | 97.01 | 600.3 |
| Example 98 | 85.63 | — |
| Example 99 | 56.18 | — |
| Example 100 | 86.73 | 99.71 |
| Example 101 | 93.01 | 149.6 |
| Example 102 | 34.90 | — |
| Example 103 | 19.35 | — |
| Example 104 | 100 | 22.96 |
| Example 105 | 71.23 | — |
| Example 106 | 100 | 60.0 |
| Example 107 | 96.96 | 70.32 |
| Example 108 | 96.16 | 50.58 |
| Example 109 | 6.18 | — |
| Example 110 | 78.40 | — |
| Example 111 | 100 | 47.21 |
| Example 112 | 36.44 | — |
| Example 113 | 100 | 62.56 |
| Example 114 | 88.65 | 37.58 |
| Example 115 | 51.28 | — |
| Example 116 | 15.37 | — |
| Example 117 | 0 | — |
| Example 118 | 20.95 | — |
| Example 119 | 40.49 | — |
| Example 120 | 0 | — |
| Example 121 | 23.12 | — |
| Example 122 | 100 | 72.11 |
| Example 123 | 31.0 | — |
| Example 124 | 86.16 | 295.4 |
| Example 125 | 100 | 373.4 |
| Example 126 | 100 | 52.62 |
| Example 127 | 66.27 | — |
| Example 128 | 100 | — |
| Example 129 | 28.28 | — |
| Example 130 | 5.31 | — |
| Example 131 | 0 | — |
| Example 132 | 85.15 | — |
| Example 133 | 5.62 | — |
| Example 134 | 18.59 | — |
| Example 135 | 100 | — |

1B. In-Vitro CRAC Channel Inhibition Assay in NCI-H460 Cancer Cell Line

Inhibition of CRAC channels was determined following thapsigargin (Sigma, Cat # T9033) induced endoplasmic calcium release in NCI-H460 cells (National Centre For Cell Science (NCCS), Pune).

Cells (30,000 per well) were plated overnight in complete RPMI medium. Medium was substituted with $Ca^{2+}$ and $Mg^{2+}$ free Hanks buffer and Fluo-8 NW dye (ABD Bioquest, Inc., Sunnyvale, Calif.) loading solution in 96-well black plate. Plate was incubated at 37° C./5% $CO_2$ for 30 min followed by further 15 min incubation at room temperature. Test compounds (DMSO stocks diluted in $Ca^{2+}$ and $Mg^{2+}$ free Hanks buffer) at desired concentrations were added to the wells and incubated for 15 min. Thapsigargin (1 µM final concentration) was added to the wells and incubated for 15 min to inhibit the Sarco-endoplasmic reticulum $Ca^{2+}$ ATPase pump thereby depleting endoplasmic calcium and raising cytosolic calcium concentrations. Store-operated calcium entry was initiated by adding extracellular $Ca^{2+}$ to a final concentration of 2.5 mM. Fluorescence was monitored over 30 min on a plate reader (BMG Labtech., Germany) with excitation at 485 nm and an emission wavelength at 520 nm. Data were analyzed using GraphPad Prism. $IC_{50}$ for each compound was determined based on the percent inhibition of Thapsigargin-induced calcium influx into cells. The results are as provided in Table 2.

1C. In-Vitro Cell Proliferation Assay in NCI-H460 Cancer Cell Line (Anticancer Activity)

Growth inhibition assays were carried out using 10% FBS supplemented media. Cells were seeded at a concentration of 5000 cells/well in a 96-well plate. Test compound at a concentration range from 0.01 to 10000 nM were added after 24 h. Growth was assessed using the 3-[4,5-dimethylthiazol-2-yl]-2,5-diphenyltetrazolium bromide (MTT) dye reduction test at 0 h (prior to the addition of the test compound) and 48 h after the addition of test compound. Absorbance was read on a Fluostar Optima (BMG Labtech, Germany) at a wave length of 450 nm. Data were analysed using Graph-Pad Prism. IC-50 for each compound was determined based on the % inhibition due to the test compound compared to the control. The results are as provided in Table 2.

For methods of cell proliferation assay, see, for example, Mosmann. T., *Journal of Immunological Methods*, 65 (1-2), 55-63, (1983).

TABLE 2

| Compound | NCI-H460 Cell Ca assay | | NCI-H460 Cell line assay | |
|---|---|---|---|---|
| | % inhibition @ 1 µM | IC 50 nM | % inhibition @ 10 µM | G1 50 nM |
| Example 1 | 93.18 | — | 31 | — |
| Example 2 | 100 | — | — | 197.3 |
| Example 6 | 85.96 | — | 35 | — |
| Example 9 | 86.85 | — | 14 | — |
| Example 21 | — | — | 41 | — |
| Example 52 | 78.23 | — | 34 | — |
| Example 53 | 84.58 | — | 22 | — |
| Example 55 | 100 | — | — | 613.4 |
| Example 90 | — | — | 90.73 | 304.9 |
| Example 91 | — | — | 92.71 | 1365 |
| Example 92 | — | — | 100 | — |

2. In Vitro Inhibition of Cytokine Release in Jurkat Cells, Human Whole Blood and Peripheral Blood Mononuclear Cells (PBMC).

Inhibition of cytokine IL-2, IL-4, IL-5 and TNF α was determined as described below.

a. Inhibition of IL-2 in Jurkat cells: Cells were incubated with desired concentrations of the inhibitor for 15 min. Cytokine release was induced by the addition of Concanavalin A (25 µg/ml)+Phorbol Myristate Acetate (50 ng/ml) for IL-2 & TNFα or with Phytohemagglutinin (5 µg/ml) for IL-4 & IL-5 and incubated at 37° C. in an atmosphere containing 95% $CO_2$. Supernatant was collected after 20 h (IL-2 & TNFα) or 48 h (IL-4 & IL-5) for estimation of cytokines by ELISA. Data were analysed using GraphPad Prism, $IC_{50}$ values for each compound were determined based on the percent inhibition due to the test compound compared to the control.

b. Inhibition of cytokine release in Human Whole Blood (HWB): Freshly collected HWB was diluted with RPMI medium (1:4.5) and added to a 96-well plate. Wells were incubated with desired concentrations of the inhibitor for 15 min. Cytokine release was induced by the addition of Concanavalin A (25 µg/ml)+Phorbol Myristate Acetate (50 ng/ml) for IL-2 & TNF or with Phytohemagglutinin (5 µg/ml) for IL-4 & IL-5 and incubated at 37° C. in an atmosphere containing 95% $CO_2$. Supernatant was collected after 20 h (IL-2 & TNFα) or 48 h (IL-4 & IL-5) for estimation of cytokines by ELISA. Data were analysed using GraphPad Prism. $IC_{50}$ values for each compound were determined based on the percent inhibition due to the test compound compared to the control.

c. Inhibition of cytokine release in PBMC: PBMC from freshly collected HWB were isolated by density gradient using Histopaque and seeded in a 96-well plate. Cells were incubated with desired concentrations of the inhibitor for 15 min. Cytokine release was induced by the addition of Concanavalin A (25 µg/ml)+Phorbol Myristate Acetate (50 ng/ml) for IL-2 & TNF or with Phytohemagglutinin (5 µg/ml) for IL-4 & IL-5 and incubated at 37° C. in an atmosphere containing 95% $CO_2$. Supernatant was collected after 20 h (IL-2 & TNFα) or 48 h (IL-4 & IL-5) for estimation of cytokines by ELISA. Data were analysed using GraphPad Prism. $IC_{50}$ values for each compound were determined based on the percent inhibition due to the test compound compared to the control. The results are as provided in Table 3.

TABLE 3

| | IC 50 Values in nM | | | | | | | | |
|---|---|---|---|---|---|---|---|---|---|
| | Jurkat | Human Whole Blood | | | | PBMC | | | |
| Compound | IL-2 | IL-2 | TNFα | IL-5 | IL-4 | IL-2 | TNFα | IL-5 | IL-4 |
| Prednisolone | 35.48 | 77.25 | — | — | — | 3.72 | — | — | — |
| Example 1 | — | 338.5 | 1078 | — | — | — | — | — | — |
| Example 28 | — | 600.4 | — | 46.28 | — | 54.27 | — | 197.5 | — |
| Example 49 | — | 198.6 | — | — | — | — | — | — | — |
| Example 53 | — | 273.7 | 125.4 | 61.83 | — | 21.33 | 121.1 | 146.2 | 79.92 |
| Example 56 | — | 78.44 | — | — | — | — | — | — | — |
| Example 78 | — | 34.71 | — | — | — | 148.7 | — | — | — |
| Example 82 | — | 38.25 | — | — | — | 24.61 | — | — | — |
| Example 83 | 57.90 | 132.4 | 546.1 | — | — | 15.69 | 86.82 | — | 352.5 |
| Example 88 | — | 229.3 | — | — | 260.2 | — | — | — | — |
| Example 93 | 140.40 | 65.10 | 147.9 | 172.9 | 141.8 | 52.90 | 66.80 | 139.6 | 264.2 |
| Example 100 | — | 77.81 | — | 56.42 | 256 | 31.42 | — | — | — |
| Example 104 | 57.46 | 96.09 | 581.8 | — | — | 66.66 | 21.08 | — | — |
| Example 106 | 60.47 | 83.59 | — | — | — | 11.50 | 104.6 | — | — |
| Example 108 | — | 138 | 38.41 | 19.79 | 142.7 | 17.5 | 16.5 | 20.65 | 55.83 |
| Example 111 | — | 82.76 | — | — | — | — | — | — | — |
| Example 143 | — | 480.4 | — | — | — | — | — | — | — |
| Example 144 | 60.80 | 243.4 | 338.4 | — | 654.6 | 141.6 | 53.23 | — | 2338 |
| Example 156 | — | 131.1 | — | — | — | 39.0 | — | — | — |

Example I: Evaluation of Usefulness of CRAC Channel Modulators in Various Anti-Inflammatory and Autoimmune Disorders Using In-Vivo Animal Models i. Concanavalin (Con) A induced Hepatitis in Female Balb/C mice: Con A is often used to prepare experimental animals with high levels of cytotoxic T-lymphocytes, because these cells are involved in the development of viral infections in humans. In this model, animals were administered test compounds orally 1 hour prior to intravenous administration of Con A. Blood samples were collected after 24 hours for determination of Serum glutamic oxaloacetic transaminase (SGOT) and Serum glutamic pyruvic transaminase (SGPT) in serum.

Results indicated >85% reduction in serum SGOT & SGPT upon administration of the test compound (example 69) at 10 mg/kg b.wt.

ii. TNCB induced contact hypersensitivity in female Balb/c mice: Contact hypersensitivity is a simple in vivo assay of cell-mediated immune function. In this procedure, exposure of epidermal cells to exogenous haptens results in a delayed type hypersensitive reaction that can be measured and quantified. Briefly, 7% TNCB solution was applied to the abdominal region of 8 week old Balb/c mice. Ear thickness was measured 7 days after TNCB sensitization. Compounds were administered orally followed by an application of 1% TNCB to inside and outside of ear pinnae. Ear thickness was measured 24 h after TNCB challenge Data demonstrated >70% reduction in ear inflammation upon administration of the test compound (example 69) at 10 mg/kg b.wt.

iii. Foot paw Delayed Type Hypersensitivity in male Balb/c mice: DTH swelling responses can be used to follow the activity of immunosuppressive molecules and/or suppressor T cells in vivo. Intradermal antigen (methylated BSA) injections were given to mice (at base of tail) on day 0 and day 7. Compounds were administered once daily from day 0 to day 10 Methylated BSA was injected into the right hind footpad of animals on day 10. Weight difference induced by antigen was determined by weighing the right and left hind paws 24 h after injection of methylated BSA (day 11).

Daily treatment of test compound (example 69) at 10 mg/kg resulted in >40% reduction in antigen-induced paw inflammation in mice.

iv. OVA-Induced Asthma in Guinea Pigs: Pulmonary eosinophilia and airway remodelling in conjunction with altered neural control of airway tone and airway epithelial desquamation contributes to Airway Hyper-responsiveness (AHR) in asthma. For determination of eosinophil reduction, animals were sensitized with OVA on d0, d7, and d14 followed by another round (0.1% w/v) through inhalation on d19 & d20. Compounds were administered orally 1 h before OVA challenge (0.3%). BAL fluid was collected on d22 for differential count and cytokine estimation. For determination of change in respiratory parameters, animals were subjected to whole body plethysmography immediately after ova challenge. Results indicated >70% reduction in blood eosinophils along with a concurrent improvement in respiration upon administration of the test compound (Example 69) at 10 mg/kg b.wt dose.

v. Collagen-induced arthritis in male DBA/1 Ola HSD mice: Collagen induced arthritis in rodent models have been widely used to illustrate and understand the development of the disease besides serving as a surrogate for validation of therapeutic targets for human rheumatoid arthritis. Mice were anesthetized with Isoflurane and given 150 μl of Bovine Type II collagen in Freund's complete adjuvant injections (day 0 and day 21). Treatment was initiated on study day 0 and continued once daily, every day (po, qd). Starting on day 18, clinical scores were given daily for each of the paws (right front, left front, right rear, left rear) and continued till the day of sacrifice (day 34). Daily administration of the test compound (Example 69) at 10 mg/kg b.wt alleviated arthritic symptoms, disease progression, and incidence by 30% compared to the control animals.

Other in-vivo models wherein the effect of CRAC channel modulators in various Anti-inflammatory and Autoimmune disorders can be tested include Chronic Experimental Autoimmune Encephalomyelitis in C57/B16J mice: Experimental Autoimmune Encephalomyelitis (EAE) is an inflammatory disease of the central nervous system and widely used as an animal model of Multiple Sclerosis. Animals are administered pertussis toxin intravenously and myelin oligodendrocyte glycoprotein (MOG) subcutaneously on day 0. Treatment is initiated at day 0 and continued till sacrifice. Development of EAE is observed between day 9 to day 42.

At the end of the treatment period, animals are sacrificed for histopathological analysis as well as cytokine estimation in plasma.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described in the specification and the claims.

All publications and patent and/or patent applications cited in this application are herein incorporated by reference to the same extent as if each individual publication or patent application was specifically and individually indicated to be incorporated herein by reference.

We claim:

1. A method of treating an autoimmune disorder comprising the step of administering to a subject in need thereof an effective amount of a compound of formula

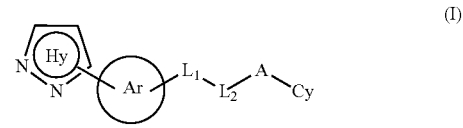

(I)

or a pharmaceutically acceptable salt thereof, wherein
Ring Hy represents

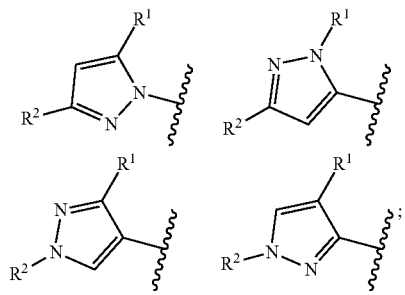

optionally substituted with R'";
$R^1$ and $R^2$ are the same or different and are independently selected from $CH_3$, $CH_2F$, $CHF_2$, $CF_3$, substituted or unsubstituted $C_{(3-5)}$cycloalkyl, $CH_2$—$OR^a$, $CH_2$—$NR^aR^b$, CN and COOH with the proviso that:
a) both $R^1$ and $R^2$ at the same time do not represent $CF_3$,
b) both $R^1$ and $R^2$ at the same time do not represent $CH_3$,
c) when $R^1$ is $CF_3$ then $R^2$ is not $CH_3$; and
d) when $R^1$ is $CH_3$ then $R^2$ is not $CF_3$;
Ring Ar represents:

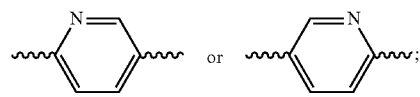

$L_1$ and $L_2$ together represent NH—C(=O)—;
A is absent;
R'" is selected from hydrogen, hydroxy, cyano, halogen, —$OR^a$, —$COOR^a$, —$S(=O)_q$—$R^a$, —$NR^aR^b$, C(=X)—R$^a$, substituted or unsubstituted C$_{(1-6)}$ alkyl group, substituted or unsubstituted C$_{(1-6)}$ alkenyl, substituted or unsubstituted C$_{(1-6)}$ alkynyl, and substituted or unsubstituted C$_{(3-5)}$cycloalkyl;

each occurrence of X is independently selected from O, S and —NR$^a$;

Cy is selected from monocyclic substituted or unsubstituted cycloalkyl group, monocyclic substituted or unsubstituted aryl; and substituted or unsubstituted pyridyl;

each occurrence of R$^a$ and R$^b$ are the same or different and are independently selected from hydrogen, nitro, hydroxy, cyano, halogen, —OR$^c$, —S(=O)$_q$—R$^c$, —NR$^c$R$^d$, —C(=Y)—R$^c$, —CR$^c$R$^d$—C(=Y)—R$^c$, —CR$^c$R$^d$—Y—CR$^c$R$^d$—, —C(=Y)—NR$^c$R$^d$—, —NRR$^d$—C(=Y)—NR$^c$R$^d$—, —S(=O)$_q$—NR$^c$R$^d$—, —NR$^c$R$^d$—S(=O)$_q$—NR$^c$R$^d$—, —NR$^c$R$^d$—NR$^c$R$^d$—, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted heterocylyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when R$^a$ and R$^b$ are directly bound to the same atom, they may be joined to form a substituted or unsubstituted saturated or unsaturated 3-10 member ring, which may optionally include one or more heteroatoms which may be the same or different and are selected from O, NR$^c$ and S;

each occurrence of R$^c$ and R$^d$ may be same or different and are independently selected from hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted heterocyclic group, substituted or unsubstituted heterocyclylalkyl, or when two R$^c$ and/or R$^d$ substitutents are directly bound to the same atom, they may be joined to form a substituted or unsubstituted saturated or unsaturated 3-10 member ring, which may optionally include one or more heteroatoms which are the same or different and are selected from O, NH and S;

each occurrence of Y is selected from O, S and —NR$^a$; and each occurrence of q independently represents 0, 1 or 2;

wherein the autoimmune disorder is chronic obstructive pulmonary disease, inflammatory bowel disease, allergic rhinitis, multiple sclerosis, psoriasis, Crohn's disease, colitis, ulcerative colitis, arthritis, bone diseases associated with increased bone resorption, or chronic obstructive airway disease.

2. The method of claim 1, wherein the autoimmune disorder is multiple sclerosis, chronic obstructive pulmonary disease, chronic obstructive airway disease, or psoriasis.

3. The method of claim 1, wherein the subject is a human subject.

4. The method of claim 2, wherein the subject is a human subject.

5. A method of modulating store-operated calcium (SOC) channel activity comprising contacting the SOC channel complex, or portion thereof, with a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

6. A method of modulating calcium release activated calcium channel (CRAC) activity in a mammal comprising administering to the mammal a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

7. A method of inhibiting store-operated calcium entry (SOCE) activation of nuclear factor of activated T cells (NFAT) in a mammal comprising administering to the mammal a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

8. A method of decreasing cytokine release by inhibiting the SOCE activation of NFAT in a mammal comprising administering to the mammal a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

9. A method of inhibiting immune cell activation comprising administering to an immune cell a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

10. A method of inhibiting T-cell and/or B-cell proliferation in response to an antigen, comprising administering to a T-cell and/or B-cell cell a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

11. A method of inhibiting cytokine production in a cell comprising administering to the cell a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

12. The method of claim 11, wherein the cytokine is selected from IL-2, IL-4, IL-5, IL-13, GM-CSF, IFN-γ, TNFα, and combinations thereof.

13. A method of modulating an ion channel in a cell, wherein the ion channel is involved in immune cell activation, comprising administering to the cell a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

14. The method of claim 13, wherein the ion channel is a Ca$^{2+}$-release-activated Ca$^{2+}$ channel (CRAC).

15. A method of reducing an inflammation in a subject in need thereof comprising administering to the subject an effective amount of a compound N-{6-[5-cyclopropyl-3-(trifluoromethyl)-1H-pyrazol-1-yl]pyridin-3-yl}-3-fluoroisonicotinamide or a pharmaceutically acceptable salt thereof.

16. A method of treating an autoimmune disorder comprising the step of administering to a subject in need thereof an effective amount of a compound N-{6-[5-cyclopropyl-3-(trifluoromethyl)-1H-pyrazol-1-yl]pyridin-3-yl}-3-fluoroisonicotinamide or a pharmaceutically acceptable salt thereof, wherein the autoimmune disorder is chronic obstructive pulmonary disease, inflammatory bowel disease, allergic rhinitis, asthma, multiple sclerosis, psoriasis, Crohn's disease, colitis, ulcerative colitis, arthritis, bone diseases associated with increased bone resorption, or chronic obstructive airway disease.

17. The method of claim 16, wherein the autoimmune disorder is multiple sclerosis, asthma, chronic obstructive pulmonary disease, chronic obstructive airway disease, or psoriasis.

18. The method of claim 16, wherein the subject is a human subject.

19. The method of claim 17, wherein the subject is a human subject.

* * * * *